(12) United States Patent
Londesbrough et al.

(10) Patent No.: US 11,634,377 B2
(45) Date of Patent: Apr. 25, 2023

(54) FENFLURAMINE COMPOSITIONS AND METHODS OF PREPARING THE SAME

(71) Applicant: ZOGENIX INTERNATIONAL LIMITED, Berkshire (GB)

(72) Inventors: Derek J. Londesbrough, Sunderland (GB); Marc W. Andersen, Raleigh, NC (US)

(73) Assignee: ZOGENIX INTERNATIONAL LIMITED, Berkshire (GB)

( * ) Notice: Subject to any disclaimer, the term of this patent is extended or adjusted under 35 U.S.C. 154(b) by 0 days.

(21) Appl. No.: 17/159,367

(22) Filed: Jan. 27, 2021

(65) Prior Publication Data

US 2021/0147335 A1 May 20, 2021

Related U.S. Application Data

(63) Continuation of application No. 16/431,391, filed on Jun. 4, 2019, now Pat. No. 10,947,183, which is a (Continued)

(51) Int. Cl.
*C07C 209/28* (2006.01)
*C07C 51/43* (2006.01)
(Continued)

(52) U.S. Cl.
CPC ............ *C07C 209/28* (2013.01); *C07C 45/72* (2013.01); *C07C 45/80* (2013.01); *C07C 51/08* (2013.01);
(Continued)

(58) Field of Classification Search
None
See application file for complete search history.

(56) References Cited

U.S. PATENT DOCUMENTS

| 3,117,160 A | 1/1964 | Holland |
| 3,198,833 A | 8/1965 | Beregi |

(Continued)

FOREIGN PATENT DOCUMENTS

| CN | 1425167 | 6/2003 |
| CN | 103025301 | 4/2013 |

(Continued)

OTHER PUBLICATIONS

Anonymous, "Health Technology Briefing: Fenfluramine hydrochloride for treatment of seizures associated with Lennox-Gastaut syndrome" NIHR Innovation Observatory (May 2019) 8 pages.
(Continued)

*Primary Examiner* — Clinton A Brooks
(74) *Attorney, Agent, or Firm* — Bret E. Field; Bozicevic, Field & Francis LLP

(57) ABSTRACT

Methods of preparing a fenfluramine active pharmaceutical ingredient are provided. Aspects of the method include (a) hydrolyzing a 2-(3-(trifluoromethyl)phenyl)acetonitrile composition to produce a 2-(3-(trifluoromethyl)phenyl)acetic acid composition; (b) reacting the 2-(3-(trifluoromethyl)phenyl)acetic acid composition with acetic anhydride and a catalyst to produce a 1-(3-(trifluoromethyl)phenyl)propan-2-one composition; and
(c) reductively aminating the 1-(3-(trifluoromethyl)phenyl) propan-2-one composition with ethylamine using a borohydride reducing agent to produce a fenfluramine composition. Also provided are compositions and pharmaceutical ingredients prepared according to the subject methods including a pharmaceutically acceptable salt of fenfluramine and having less than 0.2% by weight in total of trifluoromethyl regioisomers.

16 Claims, 5 Drawing Sheets

(1)

Related U.S. Application Data continuation of application No. 15/385,525, filed on Dec. 20, 2016, now Pat. No. 10,351,509.

(60) Provisional application No. 62/271,172, filed on Dec. 22, 2015.

(51) Int. Cl.
  *C07C 51/08* (2006.01)
  *C07C 45/80* (2006.01)
  *C07C 45/72* (2006.01)
  *C07C 209/84* (2006.01)

(52) U.S. Cl.
  CPC ............ *C07C 51/43* (2013.01); *C07C 209/84* (2013.01); *C07B 2200/13* (2013.01)

(56) References Cited

U.S. PATENT DOCUMENTS

| | | |
|---|---|---|
| 3,198,834 A * | 8/1965 | Schmitt ............... A61K 31/135 564/219 |
| 3,759,979 A | 9/1973 | Beregi et al. |
| 4,309,445 A | 1/1982 | Wurtman |
| 4,452,815 A | 6/1984 | Wurtman |
| 4,824,987 A | 4/1989 | Kleeman |
| 4,857,533 A | 8/1989 | Ward et al. |
| 5,587,398 A | 12/1996 | Elmaleh et al. |
| 5,808,156 A | 9/1998 | Cannata et al. |
| 5,811,586 A | 9/1998 | Cannata et al. |
| 5,834,477 A | 11/1998 | Mioduszewski |
| 5,985,880 A | 11/1999 | Chang |
| 6,045,501 A | 4/2000 | Elsayed et al. |
| 6,315,720 B1 | 11/2001 | Williams et al. |
| 6,561,976 B2 | 5/2003 | Elsayed et al. |
| 6,561,977 B2 | 5/2003 | Williams et al. |
| 6,599,901 B1 | 7/2003 | Flohr |
| 6,755,784 B2 | 6/2004 | Williams et al. |
| 6,869,399 B2 | 3/2005 | Williams et al. |
| 6,908,432 B2 | 6/2005 | Elsayed et al. |
| 7,141,018 B2 | 11/2006 | Williams et al. |
| 7,585,493 B2 | 9/2009 | Hale |
| 7,668,730 B2 | 2/2010 | Reardan et al. |
| 7,765,106 B2 | 7/2010 | Reardan et al. |
| 7,765,107 B2 | 7/2010 | Reardan et al. |
| 7,797,171 B2 | 9/2010 | Reardan et al. |
| 7,874,984 B2 | 1/2011 | Elsayed et al. |
| 7,895,059 B2 | 2/2011 | Reardan et al. |
| 7,959,566 B2 | 6/2011 | Williams et al. |
| 8,204,763 B2 | 6/2012 | Elsayed et al. |
| 8,263,650 B2 | 9/2012 | Cook et al. |
| 8,315,886 B2 | 11/2012 | Williams et al. |
| 8,386,274 B1 | 2/2013 | Pinsonneault |
| 8,457,988 B1 | 6/2013 | Reardan et al. |
| 8,589,182 B1 | 11/2013 | Reardan et al. |
| 8,589,188 B2 | 11/2013 | Elsayed et al. |
| 8,626,531 B2 | 1/2014 | Williams et al. |
| 8,731,963 B1 | 5/2014 | Reardan et al. |
| 9,125,900 B2 | 9/2015 | Meyer |
| 9,549,909 B2 | 1/2017 | Ceulemens |
| 9,603,814 B2 | 3/2017 | Ceulemens |
| 9,603,815 B2 | 3/2017 | Ceulemens |
| 9,610,260 B2 | 4/2017 | Ceulemens |
| 10,351,509 B2 | 7/2019 | Londesbrough |
| 10,351,510 B2 | 7/2019 | Londesbrough |
| 10,452,815 B2 | 10/2019 | Stewart et al. |
| 10,478,441 B2 | 11/2019 | Ceulemens |
| 10,478,442 B2 | 11/2019 | Ceulemens |
| 10,517,841 B1 | 12/2019 | Galer et al. |
| 10,603,290 B2 | 3/2020 | Farr |
| 10,682,317 B2 | 6/2020 | Abu-Izza |
| 10,947,183 B2 | 3/2021 | Londesbrough et al. |
| 10,950,331 B2 | 3/2021 | Stewart et al. |
| 10,952,976 B2 | 3/2021 | Galer |
| 11,040,018 B2 | 6/2021 | Farr |
| 11,352,882 B2 | 5/2022 | Farr |
| 2002/0038310 A1 | 3/2002 | Reitberg |
| 2002/0098175 A1 | 7/2002 | Zohoungbogbo |
| 2003/0007934 A1 | 1/2003 | Rabinowitz et al. |
| 2003/0118654 A1 | 5/2003 | Santos et al. |
| 2004/0249212 A1 | 12/2004 | Smallridge et al. |
| 2005/0182103 A1 | 8/2005 | Finke et al. |
| 2005/0260610 A1 | 11/2005 | Kurtz et al. |
| 2006/0121066 A1 | 6/2006 | Jaeger et al. |
| 2006/0270611 A1 | 11/2006 | Dries et al. |
| 2008/0004904 A1 | 1/2008 | Tran |
| 2008/0103179 A1 | 5/2008 | Tam |
| 2008/0243584 A1 | 10/2008 | Srinivasan |
| 2008/0261962 A1 | 10/2008 | Greer |
| 2009/0171697 A1 | 7/2009 | Glauser |
| 2010/0088778 A1 | 4/2010 | Mulley |
| 2010/0298181 A1 | 11/2010 | Hanada et al. |
| 2011/0092535 A1 | 4/2011 | Barnes et al. |
| 2011/0212171 A1 | 9/2011 | Venkatesh et al. |
| 2011/0230473 A1 | 9/2011 | Gordon et al. |
| 2012/0065999 A1 | 3/2012 | Takatoku |
| 2012/0107396 A1 | 5/2012 | Khan |
| 2012/0115958 A1 | 5/2012 | Mariotti et al. |
| 2012/0157392 A1 | 6/2012 | Martin et al. |
| 2012/0270848 A1 | 10/2012 | Mannion |
| 2012/0303388 A1 | 11/2012 | Vishnubhatla |
| 2013/0218586 A1 | 8/2013 | Huser |
| 2013/0296398 A1 | 11/2013 | Whalley |
| 2014/0030343 A1 | 1/2014 | Lamson |
| 2014/0142140 A1 | 5/2014 | Bird |
| 2014/0162942 A1 | 6/2014 | Ghosal |
| 2014/0329908 A1 | 11/2014 | Ceulemens et al. |
| 2014/0343044 A1 | 11/2014 | Ceulemens |
| 2014/0343162 A1 | 11/2014 | Ceulemens et al. |
| 2014/0348966 A1 | 11/2014 | Balemba |
| 2015/0080377 A1 | 3/2015 | Dhanoa |
| 2015/0291597 A1 | 10/2015 | Mannion |
| 2015/0310187 A1 | 10/2015 | Rabinowitz |
| 2015/0359755 A1 | 12/2015 | Guy et al. |
| 2016/0136114 A1 | 5/2016 | Ceulemens et al. |
| 2016/0228454 A1 | 8/2016 | Zhang et al. |
| 2016/0249863 A1 | 9/2016 | Ando |
| 2016/0279159 A1 | 9/2016 | Hirano et al. |
| 2017/0020885 A1 | 1/2017 | Hsu |
| 2017/0056344 A1 | 3/2017 | Farr et al. |
| 2017/0071940 A1 | 3/2017 | Olaleye et al. |
| 2017/0071949 A1 | 3/2017 | De Witte et al. |
| 2017/0151194 A1 | 6/2017 | Ceulemens |
| 2017/0151214 A1 | 6/2017 | Ceulemens et al. |
| 2017/0151257 A1 | 6/2017 | Ceulemens |
| 2017/0151259 A1 | 6/2017 | Ceulemens |
| 2017/0174613 A1 | 6/2017 | Londesbrough et al. |
| 2017/0174614 A1 | 6/2017 | Farr et al. |
| 2017/0348303 A1 | 12/2017 | Bosse |
| 2018/0028499 A1 | 2/2018 | Baraban et al. |
| 2018/0055789 A1 | 3/2018 | Farr |
| 2018/0092864 A1 | 4/2018 | Martin et al. |
| 2018/0141953 A1 | 5/2018 | Dax |
| 2018/0148403 A1 | 5/2018 | Londesbrough et al. |
| 2018/0215701 A1 | 8/2018 | Carroll et al. |
| 2018/0271821 A1 | 9/2018 | Gold |
| 2018/0325909 A1 | 11/2018 | DeWitte |
| 2019/0083425 A1 | 3/2019 | Farr |
| 2019/0091173 A1 | 3/2019 | Farfel |
| 2019/0091174 A1 | 3/2019 | Galer |
| 2019/0091175 A1 | 3/2019 | Morrison |
| 2019/0091176 A1 | 3/2019 | Galer |
| 2019/0091177 A1 | 3/2019 | Galer |
| 2019/0091179 A1 | 3/2019 | Morrison |
| 2019/0125697 A1 | 5/2019 | Farfel |
| 2019/0247333 A1 | 8/2019 | Farfel |
| 2019/0380979 A1 | 12/2019 | Galer |
| 2020/0030260 A1 | 1/2020 | Sherrington et al. |
| 2020/0030341 A1 | 1/2020 | Ceulemens |
| 2020/0170965 A1 | 6/2020 | Boyd |
| 2020/0261380 A1 | 8/2020 | Abu-Izza |
| 2020/0276136 A1 | 9/2020 | Galer |
| 2020/0297665 A1 | 9/2020 | Martin |
| 2020/0306210 A1 | 10/2020 | Morrison |
| 2020/0330406 A1 | 10/2020 | Galer |

(56) References Cited

U.S. PATENT DOCUMENTS

| | | |
|---|---|---|
| 2021/0113495 A1 | 4/2021 | Boyd |
| 2021/0121479 A1 | 4/2021 | Ceulemens |
| 2021/0158920 A1 | 5/2021 | Stewart et al. |
| 2021/0267916 A1 | 9/2021 | Farr |
| 2021/0299064 A1 | 9/2021 | Morrison |
| 2021/0330610 A1 | 10/2021 | Martin |
| 2021/0393550 A1 | 12/2021 | Farr |
| 2021/0401776 A1 | 12/2021 | Martin |
| 2022/0008389 A1 | 1/2022 | Galer |
| 2022/0016053 A1 | 1/2022 | Galer |
| 2022/0096514 A1 | 3/2022 | Quan |
| 2022/0125743 A1 | 4/2022 | Farr |
| 2022/0133652 A1 | 5/2022 | Millet |
| 2022/0160727 A1 | 5/2022 | Ceulemens |
| 2022/0193082 A1 | 6/2022 | DeWitte et al. |
| 2022/0226262 A1 | 7/2022 | Boyd et al. |

FOREIGN PATENT DOCUMENTS

| | | |
|---|---|---|
| CN | 103886415 | 6/2014 |
| CN | 111971035 | 11/2020 |
| DE | 2150399 | 4/1973 |
| EP | 0 441 160 | 8/1991 |
| EP | 0920864 | 9/1999 |
| EP | 1 399 015 | 1/2010 |
| EP | 2 399 513 | 12/2011 |
| EP | 3170807 | 5/2017 |
| GB | 1413078 | 7/1973 |
| GB | 1399015 | 6/1975 |
| GB | 1413070 | 11/1975 |
| HU | 204497 | 1/1992 |
| JP | A S64-066116 | 3/1989 |
| JP | H05-310564 A | 11/1993 |
| JP | A-2008-536545 | 9/2008 |
| JP | A-2009-525977 | 7/2009 |
| JP | A 2010-520162 | 6/2010 |
| JP | A-2011-221623 | 11/2011 |
| JP | A-2011-529923 | 12/2011 |
| JP | A-2012-511969 | 5/2012 |
| JP | A-2012-520130 | 9/2012 |
| JP | A-2012-208669 | 10/2012 |
| JP | A-2013-536857 | 9/2013 |
| JP | A-2013-248329 | 12/2013 |
| JP | 2016 216438 A | 12/2016 |
| RU | 2317104 | 2/2008 |
| RU | 103209 | 3/2011 |
| RU | 2503448 | 1/2014 |
| RU | 2571501 | 12/2015 |
| UA | 2531282 | 4/2016 |
| WO | WO 95/04713 | 2/1995 |
| WO | WO 95/32962 | 12/1995 |
| WO | WO 01/86506 | 11/2001 |
| WO | WO 2003/026591 | 4/2003 |
| WO | WO 2005/004865 | 1/2005 |
| WO | WO 2006/100676 | 9/2006 |
| WO | WO 2007/034476 | 3/2007 |
| WO | WO 2007/073503 | 6/2007 |
| WO | WO 2007/079181 | 7/2007 |
| WO | WO 2007/092469 | 8/2007 |
| WO | WO 2008/025148 | 3/2008 |
| WO | WO 2008/104524 | 9/2008 |
| WO | WO 2009/087351 | 7/2009 |
| WO | WO 2010/015029 | 2/2010 |
| WO | WO 2010/020585 | 2/2010 |
| WO | WO 2010/025931 | 3/2010 |
| WO | WO 2010/075115 | 7/2010 |
| WO | WO 2010/104841 | 9/2010 |
| WO | WO 2010/121022 | 10/2010 |
| WO | WO 2011/112606 | 9/2011 |
| WO | WO 2011/146850 | 11/2011 |
| WO | WO 2012/030927 | 3/2012 |
| WO | WO 2013/096878 | 6/2013 |
| WO | WO 2013/122897 | 8/2013 |
| WO | WO 03/077847 | 9/2013 |
| WO | WO 2014/177676 | 11/2014 |
| WO | WO 2015/026849 | 2/2015 |
| WO | WO 2015/066344 | 5/2015 |
| WO | WO 2015/193668 | 12/2015 |
| WO | WO 2016/051271 | 4/2016 |
| WO | WO 2016/138138 | 9/2016 |
| WO | WO 2016/205671 | 12/2016 |
| WO | WO 2017/035267 | 3/2017 |
| WO | WO 2017/112702 | 6/2017 |
| WO | WO 2017/122701 | 6/2017 |
| WO | WO 2018/037306 | 3/2018 |
| WO | WO 2018/060732 | 4/2018 |
| WO | WO 2018/206924 | 11/2018 |
| WO | WO 2019/067405 | 4/2019 |
| WO | WO 2019/067413 | 4/2019 |
| WO | WO 2019/067419 | 4/2019 |
| WO | WO 2019/204593 | 10/2019 |
| WO | WO 2019/216919 | 11/2019 |
| WO | WO 2019/241005 | 12/2019 |
| WO | WO 2020/014075 | 1/2020 |
| WO | WO 2020/105005 | 5/2020 |
| WO | WO 2020/112460 | 6/2020 |
| WO | WO 2020/176276 | 9/2020 |
| WO | WO 2021/156437 | 8/2021 |
| WO | WO 2022/013425 | 1/2022 |
| WO | WO 2022/069489 | 4/2022 |

OTHER PUBLICATIONS

Anonymous "Zogenix Announces Positive Top-Line Results from Global Pivotal Phase 3 Trial of FINTEPLA for the treatment of Lennox-Gastaut Syndrome" Bio Space (Feb. 6, 2020) pp. 1-12.

Baker, M. "Zogenix Completes Enrollment in Phase 3 Trial of FINTELPLA in Lennox-Gastaut Syndrome" (Jul. 8, 2019) 2 pages.

Experimental Chemistry (Continued), Part 2, Separation and Purification, (Maruzen, Co., Ltd.), Jan. 25, 1967, pp. 159-162 and 184-193.

Hawkins et al., "Synthesis of [14C] Fenfluramine and [14C]-S780" Journal of Labelled Compounds (1974) 10(4):63-670.

Hirayama, Noriaki, Organic Compound Crystallization Handbook: Principles and Know-How (Maruzen, Co., Ltd.), Jul. 25, 2008, pp. 57-84.

Ji et al., "Study of Fenfluramine Synthesis Route" Journal of Shenyang College of Pharmacy (Apr. 1994) 11(2):116-118.

Lewis et al., "Biosynthesis of Canescin, a Metabolite of *Aspergillus malignus*: Incorporation of Methionine, Acetate, Succinate, and Isocoumarin Precursors, Labelled with Deuterium and Carbon-13" J. Chem. Soc. Perkin Trans I (1988) pp. 747-754.

Notification issued by the Director of Pharmaceutical and Medical Safety Bureau, Ministry of Health and Welfare, Guidelines for Residual Solvents in Pharmaceuticals, PMSB/ELD Notification No. 307, 1998, pp. 1-11.

Oguni et al., "Treatment and Long-Term Prognosis of Myoclonic-Astatic Epilepsy of Early Childhood" Neuropediatrics (2002) 33(3):122-32.

Su et al, "The Synthesis of 2-Amino-1-Penylpropanes" Chemical Journal of Chinese Universities (1988) 9(2):134-139.

Van Der Steldt et al., "The Effect of Alkyl Substitution in Drugs" Arzneimittelforschung—Drug Research (1965) 15:1251-1253.

Werbel et al., "Synthesis, Antimalarial Activity, and Quantitative Structure-Activity Relationships of Tebuquine and a Series of Related 5-[(7-Chloro-4-quinolinyl)amino]-3[(alkylamino)methyl][1,1'-biphenyl]-2-ols and N omega-Oxides" J. Med. Chem. (1986) 29:924-939.

ONFI Prescribing Information. Lundbeck, Deerfield, Reference ID: 4028780 [online], Dec. 2016, [retrieved on Jun. 22, 2021], <URL: https://www.accessdata.fda.gov/drugsatfda_docs/label/2016/203993s005lbl.pdf>.

Study NCT02926898 on Date: May 1, 2017 (v6), ClinicalTrials.gov archive[online], May 1, 2017, [retrieved on Jun. 22, 2021], <URL: https://clinicaltrials.gov/ct2/history/NCT02926898>.

Zaccara et al., "Interactions between antiepileptic drugs, and between antiepileptic drugs and other drugs" Seminar in Epileptology (2014) 16(4):409-432.

(56) References Cited

OTHER PUBLICATIONS

Klein et al., "Cannabidiol potentiates Delta$^9$-tetrahydrocannabinol (THC) behavioural effects and alters THC pharmacokinetics during acute and chronic treatment in adolescent rats" Psychopharmacology (2011) 218:443-457.
Registry(STN) [online], Jun. 7, 2015, [Retrieval Date: Sep. 28, 2020], CAS Registry No. 1775169-27-1.
Slick et al., "Frequency of Scale Elevations and Factor Structure of the Behavior Rating Inventory of Executive Function (Brief) in Children and Adolescents with Intractable Epilepsy" Child Neuropsychology (2006) 12:181-189.
Kelley et al., "Doose syndrome (myoclonic-astatic epilepsy): 40 years of progress" Developmental Medicine & Child Neurology (2010) 52(11):988-993.
McTague et al., "The genetic landscape of the epileptic encephalopathies of infancy and childhood" Lancet Neurol. (2016) 15:304-316.
Anandam, R., Affiliations Indian Journal of Pediatrics (Jan. 1, 2000) 67 (1 Suppl):S88-91 (Abstract Only).
Anonymous "Selective Serotonin reuptake Inhibitor—Wikipedia" Internet https://en.wikipedia.org/wiki/Selective_serotonin_reuptake_inhibitor (Feb. 1, 2020 (retrived on Feb. 4, 2020)).
Aras et al., "The European patient with Dravet Syndrome: Results from a parent-reported survey on antiepileptic drug use in the European population with Dravet Syndrome" Epilepsy & Behavior (2015) 44:104-109.
F Brenot et al., "Primary Pulmonary Hypertension and Fenfluramine Use.", Heart, vol. 70, No. 6, Dec. 1, 1993 (Dec. 1, 1993), pp. 537-541.
Brunklaus et al., "Prognostic, clinical and demographic features in SCN1A mutation-positive Dravet syndrome" Brain, 2012, p. 1-8.
Brunklaus et al., "Dravet syndrome—From epileptic encephalopathy to channelopathy" Epilepsia (May 16, 2014) 55(7):979-984.
Buchanan, Gordon F. et al., Serotonin neurones have anticonvulsant effects and reduce seizure-induced mortality, The Journal of Physiology, 2014, vol. 592, Issue 19, p. 4395-4410.
Carvalho et al., "d-Amphetamine Interaction with Glutathione in Freshly Isolated Rat Hepatocytes" Chemical Research in Toxicology (Jan. 1996) 9(6):1031-1036.
C. B. Catarino et al. "Dravet Syndrome as epileptic encephalopathy: Evidence from long-term course and neuropathology", Brain, vol. 134, No. 10 (Jun. 29, 2011) pp. 2982-3010.
Ceulemans et al., "Poster presented at the 69$^{th}$ Annual Meeting of the American Epilepsy Society" (Dec. 2015) Philadelphia.
Ceulemans B., "Successful Use of Fenfluramine as Add-On Treatment in Dravet Syndrome" Epilepsia, 52(Suppl. 6):4-22 (2011).
Ceulemans et al., "Five-year extended follow-up status of 10 patients with Dravet syndrome treated with fenfluramine" Epilepsia (May 20, 2016) 57(7):e129-e134.
Clinical Trials ClinicalTrials.gov Identifier: NCT02224560 (Jul. 27, 2018).
Curzon et al., "Appetite suppression by commonly used drugs depends on 5-HT receptors but not on 5-HT availability" Tips (1997) 18:21-25.
Devinsky et al., "Trial of Cannabidiol for Drug-Resistant Seizures in the Dravet Syndrome" The New Engalnd Journal of Medicine (May 25, 2017) 376(21):2011-2020.
C. Doege et al., "Myoclonic-astatic epilepsy: Doose-Syndrum 2014: Doose syndrome 2014", Zeitschrift FR Epileptologie, (Mar. 20, 2014).
Döring et al. "Thirty Years of Orphan Drug Legislation and the Development of Drugs to Treat Rare Seizure Conditions: A Cross Sectional Analysis" PLOS One, pp. 1-15 (Aug. 24, 2016).
Dravet, Charlotte, "The core Dravet syndrome phenotype" Epilepsia, 52(Supp. 2):3-9 (2011).
Faingold et al., "Prevention of seizure-induced sudden death in a chronic SUDEP model by semichronic administration of a selective serotonin reuptake inhibitor" Epilepsy & Behavior (2011) 22:186-190.
Favale et al., "The anticonvulsant effect of citalopram as indirect evidence of serotonergic impairment in human epileptogenesis" Seizure (2003) 12:316-319.
File History of U.S. Pat. No. 9,549,909 issued on Jan. 24, 2018 (571 pp).
File History of U.S. Pat. No. 9,603,815 issued on Mar. 28, 2017 (385 pp).
File History of U.S. Pat. No. 9,603,814 issued on Mar. 28, 2017 (466 pp).
File History of U.S. Pat. No. 9,610,260 issued on Apr. 4, 2017 (371 pp).
File History of U.S. Pat. No. 10,478,441 issued on Nov. 19, 2019 (761 pp).
File History of U.S. Pat. No. 10,478,442 issued on Nov. 19, 2019 (980 pp).
File History of U.S. Appl. No. 14/447,369, filed Jul. 30, 2014 (now abandoned) (285 pp.).
File History of U.S. Appl. No. 15/429,650, filed Feb. 10, 2017 (now abandoned) (267 pp).
File History of U.S. Appl. No. 15/429,641, filed Feb. 10, 2017 (now abandoned) (285 pp).
File History of U.S. Appl. No. 15/429,506, filed Feb. 10, 2017 (now abandoned) (641 pp).
File History of U.S. Appl. No. 16/596,166, filed Oct. 8, 2019 (now abandoned) (123 pp).
File History of U.S. Appl. No. 16/869,284, filed May 7, 2020 (now abandoned) (42 pp).
File History of U.S. Appl. No. 16/909,055, filed Jun. 12, 2020 (pending) (85 pp).
File History of U.S. Pat. No. 10,351,509 issued Jul. 16, 2019 (226 pp).
File History of U.S. Pat. No. 10,351,510 issued Jul. 16, 2019 (244 pp).
File History of U.S. Pat. No. 10,947,183 issued Mar. 16, 2021 (293 pp).
Franco-Perez, Javier "The Selective Serotonin Reuptake Inhibitors: Antidepressants with Anticonvulsant Effects?" Ann Deoress Anxiety (2014) 1(5):1025 (2 pages).
Gastaut et al., "Compulsive respiratory sterotypies in children with autistic features: Polygraphic recording and treatment with fenfluramine" Journal of Autism and Developmental Disorders, (Sep. 1, 1987) 17(3):391-406.
Gharedaghi et al., "The role of different serotonin receptor subtypes in seizure susceptibility" Exp. Brain Res (2014) 232:347-367.
Gioia et al., "Confirmatory Factor Analysis of the Behavior Rating Inventory of Executive Function (BRIEF) in a Clinical Sample" Child Neuropsychology (2002) 8(4):249-57.
Habibi et al., "The Impact of Psychoactive Drugs on Seizures and Antiepileptic Drugs" Current Neurology and Neuroscience Reports (Jun. 17, 2016) 16(8):1-10.
Haritos et al., "Metabolism of dexfenfluramine in human liver microsomes and by recombinant enzymes: Role of CYP2D6 and 1A2" Pharmcogenetics (Oct. 1998) 8(5):423-432.
Harvard Health Publishing, Harvard Medical School Generalized Seizures (Grand Mal Seizures) (Apr. 2014) pp. 1-5 (https://www.health.hearvard.edu/diseases-and-conditions/generalized-seizures-grand-mal-se . . . ).
Hazai et al., "Reduction of toxic metabolite formation of acetaminophen" Biochemical and Biophysical Research Communications (Mar. 8, 2002) 291(4):1089-1094.
Hegadoren et al., "Interactions of iprindole with fenfluramine metabolism in rat brain and liver" Journal of Psychiatry & Neuroscience (Mar. 1991) pp. 5-11.
Inoue et al., "Stiripentol open study in Japanese patients with Dravet Syndrome" Epilepsia, 50(11):2362-2368 (2009).
Isaac, Methvin, Serotonergic 5-HT2C Receptors as a Potential Therapeutic Target for the Design Antiepileptic Drugs, Current Topics in Medicinal Chemistry, 2005, vol. 5, Issue 1, p. 59-67.
Katholieke Universiteit Leuven, University Hospital Antwerp: "Interim results of a fenfluramine open-label extension study", European Patent Register (May 25, 2017).
Klein, M. T. and Teitler, M. , Distribution of 5-ht1E receptors in the mammalian brain and cerebral vasculature: an immunohistochemi-

(56) References Cited

OTHER PUBLICATIONS cal and pharmacological study, British Journal of Pharmacology, Jun. 2012, vol. 166, No. 4, p. 1290-1302.

Lagae et al. "A pilot, open-label study of the effectiveness and tolerability of low-dose ZX008 (fenfluramine HCl) in Lennox-Gastaut syndrome" Epilepsia (2018) 59: 1881-1888.

Leit, Silvana et al., Design and synthesis of tryptamine-based 5HT2C agonists for the treatment of certain CNS disorders, Division of Medicinal Chemistry Scientific Abstracts for the 240th National ACS Meeting and Exposition, Jul. 28, 2010, MEDI367.

LeJeune et al., "Psychometric Support for an Abbreviated Version of the Behavior Rating Inventory of Executive Function (BRIEF) Parent Form" Child Neuropsychology (2010 16:182-201.

Lopez-Meraz et al., "5-$HT_{1A}$ receptor agonist modify epileptic seizures in three experimental models in rats" Neuropharmacology (2005) 49:367-375.

Manzke et al., "5-HT4(a) receptors avert opiod-induced breathing depression without loss of analgesia" Science (Jul. 11, 2003) 301:226-229.

Martin, et al., "An Examination of the Mechanism of Action of Fenfluramine in Dravet Syndrome: A Look Beyond Serotonin" Presented as part of the Zogenix Scientific Exhibit During the $70^{th}$ Annual Meeting of the American Epilepsy Society, Houston, Texas (Dec. 2-6, 2016).

Mudigoudar et al., "Emerging Antiepileptic Drugs for Severe Pediatric Epilepsies" Seminars in Pediatric Neurology (Jun. 2016) 23(2):167-179.

Naithani et al., "The Conventional Antiepileptic Drug Use When Compared to a Combination Therapy Regime in a Teaching Hospital in India" International Journal of Pharma and Bio Sciences (2012) 3(1):B-191-B-197.

NCT02682927 (Sep. 3, 2016, 10 pages) Accessed from https://www.clinicaltrials.gov/ct2/history/NCT02682927?V_=View#StudyPageTop on Mar. 18, 2019.

Nozulak et al., "(+)-cis-4,5,7a,8,9,10,11,11a-Octahydro-7H-10-methylindolo[1,7-bc][2,6]-naphthridine: A 5-$HT_{2C/2B}$ Receptor Antagonist with Low 5-$HT_{2A}$ Receptor Affinity" J. Med. Chem. (1995) 38:28-33.

O'Neill et al., "GR46611 potentiates 5-$HT_{1A}$ receptor-mediated locomotor activity in the guinea pig" European Journal of Pharmacology (1999) 370:85-92.

Pirincci et al., "The Effects of Fefluramine on Blood and Tissue Seratonin (5-Hydroxytryptamine) Levels in Rats" Turk J Vet Anim Sci (2005) 29:857-863.

Pittala, Valeria et al., 5-HT7 Receptor Ligands: Recent Developments and Potential Therapeutic Applications, Mini-Reviews in Medicinal Chemistry, 2007, vol. 7, Issue 9, p. 945-960.

Jake Remaly: "Fenfluramine Reduces Convulsive Seizure Frequency in Dravet Syndrome. Epilepsy Resource Center", Jan. 1, 2018 (Jan. 1, 2018).

Rho, Jong M. "Basic Science Behind the Catastrophic Epilepsies" Epilepsia (2004) 45(Suppl.5):5-11.

Rothman et al., "Serotonergic drugs and valvular heart disease" Expert Opinion on Drug Safety (May 2009) 8(3):317-329.

Russo et al., "Agonistic Properties of Cannabidiol at 5-HT1a Receptors" Neurochemical Research (2005) 30(8):1037-1043.

Schoonjans, An-Sofie "Low-dose fenfluramine in the treatment of neurologic disorders: experience in Dravet syndrome" Therapeutic Advances in Neurological Disorders (Jan. 1, 2015) pp. 328-338.

Schoonjans et al. "Low-dose fenfluramine significantly reduces seizure frequency in Dravet syndrome: a prospective study of a new cohort of patients", European Journal of Neurology, vol. 24, No. 2, (Oct. 28, 2016), pp. 309-314.

An-Sofie Schoonjans et al: "Cardiovascular Safety of Low-Dose Fenfluramine in Dravet Syndrome: A Review of its Benefit-Risk Profile in a New Patient Population", Current Medical Research and Opinion, vol. 33, No. 10, Jul. 31, 2017 (Jul. 31, 2017), pp. 1773-1781.

Selmer et al., "SCN1A mutation screening in adult patients with Lenox-Gastaut syndrome features" Epilepsy & Behavior (Nov. 1, 2009) 16(3):555-57.

Sharma et al. Indian Journal of Pharmacology, 1996, 28(1), 1-10.

Sourbron et al., "Serotonergic Modulation as Effective Treatment for Dravet Syndrome in Zebrafish Mutant Model" ACS Chemical Neuroscience (Feb. 17, 2016) 7(5):588-598.

Sullivan et al. "Effext of ZX008 (fenfluramine HCl oral solution) on total seizures in Dravet syndrome" Neurology: Official Journal of the American Academy of Neurology, 2018, 90(24):e2187-e2811.

Van Rijckevorsel, Kenou, "Treatment of Lennox-Gastaut syndrome: overview and recent findings" Neuropsychiatric Disease and Treatment, 4(6):1001-1019 (2008).

Vickers et al., "Oral Administration of the 5-HT2C receptor agonist, mCPP, reduces body weight gain in rats over 28 days as a result of maintained hypophagia" Psychopharmacology (May 2003), 167 (3): 274-280.

Viola et al., "The Behavior Rating Inventory of Executive Function (BRIEF) to Identify Pediatric Acute Lymphoblastic Leukemia (ALL) Survivors At Risk for Neurocognitive Impairment" Journal of Pediatric Hematology/Oncology (Apr. 1, 2017) 39(3):174-178.

Wallace et al., "Pharmacotherapy for Dravet Syndrome" Paediatr. Drugs, 18(3):197-208 (Jun. 2016).

Wirrell et al., "Stiripentol in Dravet syndrome: Results of a retrospective U.S. study" Epilepsia (2013) 54(9):1595-1604.

Wirrell et al., "Stiripentol in Dravet Syndrome: Is it Worth It?" Epilepsy Currents, 14(1):22-23 (Jan./Feb. 2014).

Wirrell et al., "Treatment of Dravet Syndrome" Can. J. Neurol. Sci., 43(Suppl. 3):S13-18 (Jun. 2016).

Wirrell et al., "Optimizing the Diagnosis and Management of Dravet Syndrome: Recommendations From a North American Consensus Panel" Pediatric Neurology (Mar. 2017) 68:18-34.

Wurtman et al., "Fenfluramine and other serotoninergic drugs depress food intake and carbohydrate consumption while sparing protein consumption" Current Medical Research and Opinion (1979) 6(1 Supp):28-33.

Yamaori et al., "Potent inhibition of human cytochrome P450 3A isoforms by cannabidiol: Role of phenolic hydroxyl groups in the resorcinol moiety" Life Sciences (2011) 88:730-736.

Yoshida et al. (2017), "Impact of Physiologically Based Pharmacokinetic Models on Regulatory Reviews and Product Labels: Frequent Utilization in the Field of Oncology" in Clinical Pharmacology and Therapeutics 2017; 101(5): 597-602.

Zhang et al., *A Physiological-based Pharmacokinetic (PBPK) Modeling Approach to Quantifying Drug-Drug Interactions: Applications to the Development of Fenfluramine (ZX008) for Treatment of Seizures in Dravet Syndrome (DS).* Presented at the 2016 American Conference for Pharmacokinetics.

Zhang et al., A Physiological-based Pharmacokinetic (PBPK) Modeling Approach to Quantifying Drug-Drug Interactions: Applications to the Development of Fenfluramine (ZX008) for Treatment of Seizures in Dravet Syndrome (DS). Published in Abstracts accepted for American Conference on Pharmacometrics 2016 (ACoP7).

Zhang et al., "Pharmacological Characterization of an Antisense Knockdown Zebrafish Model of Dravet Syndrome: Inhibition of Epileptic Seizures by the Serotonin Agonist Fenfluramine" PLOS One (May 12, 2015) 10(5)::16-17 (Abstract).

Zhuang et al. (2016), "PBPK modeling and simulation in drug research and development" in Acta Pharmaceutica Sinica B 2016;6(5):430-440.

Zogenix "Corporate Update Nasdaq: ZGNX" (Jun. 1, 2016) Retrieved from the Internet: URL:http://www.jefferies.com/CMSFiles/Jefferies.com/files/Conferences/060716/Presentations/Zogenix%20Inc.pdf [retrieved on Feb. 21, 2018].

Aicardi et al., "Treatment of Self-Induced Photosensitive Epilepsy with Fenfluramine" New England Journal of Medicine (1985) 313:1419.

Aicardi et al., "Syncopal Attacks Compulsively Self-induced by Valsalva's Maneuver Associated with Typical Absence Seizures" Archives of Neurology (1988) 45:923-925.

(56) References Cited

OTHER PUBLICATIONS

Anonymous, "MacReportMedia—Brabant Pharma Reports Two-Year Follow-up Data From a 19-year Observational Study Using Low-Dose Fenfluramine for the Treatment of Dravet Syndrome", Nov. 25, 2013 (Nov. 25, 2013).

Anonymous, "Determination That PONDIMIN (Fenfluramine Hydrochloride) Tablets, 20 Milligrams and 60 Milligrams, and PONDEREX (Fenfluramine Hydrychloride) Capsules, 20 Milligrams Were Withdrawn From Sale For Reasons of Safety or Effectiveness" Federal Register (Sep. 29, 2015) pp. 58490-58491.

Arzimanoglou, Alexis, "Dravet syndrome: From electroclinical characteristics to molecular biology" Epilepsia (2009) 50(Suppl 8):3-9.

Bird et al., "Combination of pharmaceutical compositions for treatment of neurological disorders" STN International (Columbus, Ohio) HCAPLUS database, Accession No. 2013:83254 (2013).

Boel and Casaer et al., "Add-on Therapy of Fenfluramine in Intractable Self-Induced Epilepsy" Neuropaediatrics (1996) 27(4):171-173.

Boel and Casaer et al., "Fenfluramine as a Potential Antiepileptic Drug" Epilepsia (2002) 43(2):205-206.

Ceulemans, "Overall management of patients with Dravet syndrome" Developmental Medicine & Child Neurology (2011) 53:19-23.

Ceulemans et al., "Successful use of fenfluramine as an add-on treatment for Dravet syndrome" Epilepsia (2012) 53(7):1131-1139.

Ceulemans B. et al., "Successful use of Fenflurarmine as add-on treatment in Dravet syndrome: a two year prospective follow up", European Journal of Paediatric Neurology (Sep. 1, 2013) vol. 17:01101866.

Chiron et. al., "The pharmacologic treatment of Dravet syndrome" Epilepsia (2011) 52(Suppl 2):72-75.

Clemens, Bela, "Dopamine agonist treatment of self-induced pattern-sensitive epilepsy. A case report" Epilepsy Research (1988) 2:340-343.

Coma et al, "New combination therapies for treating neurological dissorders" STN International (Columbus, Ohio) HCAPLUS database, Accession No. 2013:682383 (2013).

Cozzi et al., "Indan Analogs of Fenfluramine and Norfenfluramine Have Reduced Neurtoxic Potential" Pharmacology Biochemistry and Behavior (1998) 59(3):709-715.

Dimpfel et al., "Hesperidin and hesperetin for the treatment of epilepsy migraine, schizophrenia, depression, and drug abuse" STN International (Columbus, Ohio) HCAPLUS database, Accession No. 2006:1205690 (2006).

Gentsch et al., "Laboratory Research Fenfluramine Blocks Low-Mg2'-Induced Epileptiform Activity in Rat Entorhinal Cortex" Epilepsia (Jan. 1, 2000), pp. 925-928.

Gross et al., "The influence of the sparteine/debrisoquine genetic polymorphism on the disposition of dexfenfluramine" Br J Clin Pharmacol (1996) 41:311-317.

Kaiser et al., "Synthesis and Anorectic Activity o Some 1-Benzylcyclopropylamines" Journal of Medicinal Chemistry, American Chemical Society, US (1970) 13(5):820-826.

Lambert et al., "Inductive Enhancement of Aryl Participation" Journal of the American Chemical Society (Apr. 27, 1977) 99(9):3059-67.

Meador K J., "Seizure reduction with fluoxetin in an adult woman with Dravet syndrome", Epilepsy & Behavior Case Reports, Elsevier BV, NL (Jan. 1, 2014) 2(1):54-56.

Mulley et al., "SCN1A Mutations and Epilepsy" Human Mutation (2005) 25:535-542.

Patani et al.;, "Bioisosterism: A Rational Approach to Drug Design" Chem. Rev. (1996) 96:3147-3176.

Porra et al., "Determination of Fenfluramine Enantiomers in Pharmaceutical Formulations by Capillary Zone Electrophoresis" Chromatographia (Oct. 1995) 41(7/8):383-388.

Remington, "The Science and Practice of Pharmacy", Nineteenth Edition (1995), pp. 710-712.

Rothman et al., "(+)-Fenfluramine and Its Major Metabolite, (+)-Norfenfluramine, Are Potent Substrates for Norepinephrine Transporters" The Journal of Pharmacology and Experimental Therapeutics (2003) 305(3)1191-1199.

Tran et al., "Dakin-West Synthesis of β-Aryl Ketones" J. Org. Chem. (2006) 71:6640-6642.

Bagdy et al., "Serotonin and epilepsy," J. Neurochem., 100:857-73 (2007).

Ceulemans et al., "Clinical Correlations of Mutations in the SCN1A Gene: From Febrile Seizures to Severe Myoclonic Epilepsy in Infancy" Pediatr. Neurol. 30(4):236-43 (2004).

Coleman et al., "Monitoring for adverse drug reactions," Br. J. Clin. Pharmacol., 61(4):371-78 (2006).

"Diacomit: EPAR—Scientific Discussion," European Medicines Agency ("EPAR Diacomit") https://www/ema/europa.eu/en/documents/scientific-discussion/diacomit-epar-scientific-discussion_en.pdf, published 2009.

Ferretti et al., "Direct High-performance liquid chromatograph resolution on a chiral column of dexfenfluramine and its impurities, in bulk raw drug and pharmaceutical formulations" J. Chromatogr. A. 731:340-45 (1996).

Gordon et al., "A SARS-CoV-2 protection interaction map reveals targets for drug repurposing" Nature (Apr. 30, 2020) 583(7816:459-468.

Haute Autorité de Santé (HAS), French National Authority for Health, issued an opinion on Diacomit ("HAS Opinion") https://www.has-sante.fr/upload/dox/application/pdf/2010-01/diacomit_ct_4347.pdf (Jun. 6, 2007).

Heisler et al., "Epilepsy and Obesity in Serotonin 5-HT$_{2C}$ Receptor Mutant Mice," Ann. NY Acad. Sci. 861:74-78 (1998).

International Conference On Harmonisation Of Technical Requirements for Registration of Pharmaceuticals for Human Use,"ICH Harmonised Tripartite Guidline: Impurities in New Drug Substances," Q3A(R2) (2006).

Jingyu et al., "Study on Synthesis of Amphetamine Compounds" Chem J. of Chinese Univ., 9(2), 12 pages (1988).

Martin et al., "Fenfluramine acts as a positive modulator of sigma-1 receptors" Epilepsy and Behavior, Academic Press, San Diego, CA, US (Mar. 10, 2020) 105:1-9.

Mathews et al., "Effect of D-Fenfluramine on the Lymphocyte Response of HIV$_+$ Humans" International Journal of Immunopharmacology (Jan. 1, 1998) 20:751-763.

Olson et al., "Cyclin-Dependent Kinase-Like 5 Deficiency Disorder: Clinical Review" Pediatric Neurology (2019) 97:18-25.

Public Law 110-85, 110th Congress ("FDA Amendments Act of 2007") published 2007.

Scala et al., "CDKL5/STK9 is mutated in Rett syndrome variant with infantile spasms" J Med Genet (2005) 42:103-107.

Vela, Jose Miguel "Repurposing Sigma-1 Receptor Ligands for COVID-19 Therapy?" Frontiers in Pharmacology (Nov. 9, 2020) 11:1-23.

Wee et al., "Risk for Valvular Heart Disease among Users of Fenfluramine and Dexfenfluramine Who Underwent Echocardiography before Use of Medication," Annals of Internal Medicine, 129(11):870-874 (1998).

Droogmans et al., "Role of echocardiography in tox heart vavulopathy" European Journal of Echocardiography, 10:467-476 (2009).

Garone et al., "Deoxypyrimidine monophosphate bypass therapy for thymidine kinase 2 deficiency" EMBO Molecular Medicine Aug. 1, 2014) 6(8):1016-1027.

LoPinto-Khoury et al., "Antiepileptic Drugs and Markers of Vascular Risk" Curr Treat Options Neurol (Jul. 2010) 12(4):300-308.

Pottkamper et al., "The postictal state—What do we know?" Epilepsia (2020) 61(6):1045-1061.

Remi et al., "Clinical features of the postictal state: Correlation with seizure variables" Epilepsy & Behavior (2010) 91(2):114-117.

Subota et al., "Signs and Symptoms of the postictal period in epilepsy: A systematic review and meta-analysis" Epilepsy & Behavior (2019) 94:243-251.

Thurman et al., "Sudden expected death in epilepsy: Assessing the public health burden" Epilepsia (2014) 55(10):1479-1485.

(56) References Cited

OTHER PUBLICATIONS

Tupal et al., "Serotonin 5-HT$_4$ receptors play a critical role in the action of fenfluramine to block seizure-induced sudden death in a mouse model of SUDEP" Epilepsy Research (2021) 177:1-7.
Vivero et al., "A close look at fenfluramine and dexfenfluramine" The Journal of Emergency Medicine (1998) 16(2):197-205.
Archer et al., "Primary Pulmonary Hypertension, A Vascular Biology and Translational Research "Work in Progress"" Clinical Cardiology: New Frontiers, Circulation, 102:2781-2791 (Nov. 28, 2000).
Echocardiogram, Echocardiogram Test for Pulmonary Arterial Hypertension PAH (https:///pulmonaryhypertensionm.com/echocardiogram/) pp. 1-5 (Jan. 4, 2012).
FDA-approved Treatments for Pulmonary Hypertension, Vera Moulton Wall Center for Pulmonary Vascular Diseases, Stanford (https://med.stanford.edu/wallcenter/patient-resources/fda.html) pp. 1-8 (Jan. 19, 2017).
Gardner, Amanda "Living Your Best With Pulmonary Hypertension" WebMD, pp. 1-5 (Jan. 2, 2019).
Khan et al., "Epileptic Encephalopathies: An Overview" Epilepsy Research and Treatment, vol. 2012, pp. 1-8 (Sep. 12, 2012).
Mari et al., "CDKL5 belongs to the same molecular pathway of MeCP2 and it is responsible for the early-onset seizure variant of Rett syndrome" Human Molecular Genetics (2005) 14(14):1935-1946.
Pulmonary Hypertension and Edema, (pulmonaryhypertensionnews.com/pulmonary-hypertension-and-edema/) pp. 1-3 (Nov. 9, 2015).
Scheffer et al., "ILAE classification of the epilepsies: Position paper of the ILAE Commission for Classification and Terminology" Epilepsia (2017) 58)4):512-521.
Specchio et al., "International League Against Epilepsy classification and definition of epilepsy syndromes with onset in childhood: Position paper by the ILAE Task Force on Nosology and Definitions" Epilepsia (Mar. 17, 2022) 00:1-45.
Weir et al., "Anorexic Agents Aminorex, Fenfluramine, and Dexfenfluramine Inhibit Potassium Current in Rat Pulmonary Vascular Smooth Muscle and Cause Pulmonary Vasoconstriction" American Heart Association, Circulation, 94(9):2216-2220 (Nov. 1996).
Zuberi et al., "Commentary: A New Classification is Born" International League Against Epilepsy (2017) pp. 511.
Aylward et al., "Screening and Assessment Tools" Developmental-Behavioral Pediatrics Evidence and Practice (2008) 123-201.
Berge et al., "Pharmaceutical Salts" J. Pharm Sci (1977) 68(1):1-19.
Busner et al., "Global Impressions Scale: Applying a Research Tool in Clinical Practice" Psychiatry (2007) 29-37.
Ceulemans B., "Successful Use of Fenfluramine as Add-On Treatment in Dravet Syndrome" Epilepsia, 52(Suppl. 6):4-22 (2011) (Abstract Only).

De Jonghe et al., "Molecular genetics of Dravet syndrome" Developmental Medicine & Child Neurology (2011) 53 (Supp 2):7-10.
Dravet. Charlotte, "Dravet Syndrome History" Developmental Medicine & Child Neurology (2011) 53 (Suppl. 2):1-6.
"Guideline on clinical investigation of medicinal products in the treatment of epileptic disorders" European Medicines Agency (Jul. 22, 2010) pp. 1-17.
Marini et al., "The genetics of Dravet Syndrome" Epilepsia (2011) 52(Suppl. 2):24-29.
Mayer et al., "Refractory Status Epilepticus" Archives of Neurology, American Medial Association, Chicago, IL, US (Feb. 1, 2022) 59(2):205-210.
Patino et al., "A Functional Null Mutation of SCN1B in a Patient with Dravet Syndrome" J. Neurosci. (2009) 29(34):10764-10778.
Rawson et al., "Bacterial and Funcal Coinfection in Individuals with Coronavirus: A Rapid Review to Support COVID-19 Antimicrobial Prescribing" Clinical Infection Diseases (2020) 71:2459-2468.
Shorvon et al., "The treatment of super-refractory status epilepticus: a critical review of available therapies and a clinical treatment protocol" Brain (Oct. 1, 2011) 134(10)2802-2818.
Singh et al., "A Role of SCN9A in Human Epilepsies, As a Cause of Febrile Seizures and As a Potential Modifier of Dravet Syndrome" PLoS Genetics (2009) 5(9):9-12 (pp. 1-14).
Wikipedia "Marburg acute multiple sclerosis" (Dec. 26, 2020), retrieved on Oct. 9, 2022.
Asatryan, Babken "Challenges in Decoding Sudden Unexpected Death in Epilepsy: The Intersection Between Heart and Brain in Epilepsy" Journal of the American Heart Association (2021) 10(23):e023571, pp. 1-4.
BNF 39—British National Formulary (Mar. 2000) p. 197.
Caraballo et al., "Ketogenic diet in patients with Lennox-Gastaut syndrome" Seizure (2014) 23:751-755.
Cross et al., "Expert Opinion on the Management of Lennox-Gastaut Syndrome: Treatment Algorithms and Practical Considerations" Frontiers in Neurology (Sep. 29, 2017) 8(505):1-18.
Fisher et al., "Definition of the postictal state: When does it start and End?" Epilepsy & Behavior (2010) 19(2):100-104.
Grosso et al., "Dexfenfluramine effective in drug-resistant temporal lobe epilepsy" Neurology, Lippincott Williams & Wilkins, Philadelphia, US (Sep. 25, 2001) 57(6):1139-1140.
Hay et al., "Clinical development success rates for investigational drugs" Nature Biotechnology (Jan. 2014) 32(1):40-51.
Knupp et al., "Efficacy and Safety of Fenfluramine for the Treatment of Seizures Associated with Lennox-Gastaut Syndrome" JAMA Neurology (Jun. 2022) 79(6):554-564.
MIMS—Monthly Index of Medical Specialties (Sep. 1997) pp. 240-241.
Samanta, Debopam "Changing Landscape of Dravet Syndrome Management: An Overview" Neuropediatrics (2020) 51(2):135-145.

\* cited by examiner

FENFLURAMINE COMPOSITIONS AND METHODS OF PREPARING THE SAME

INTRODUCTION

Fenfluramine is an amphetamine drug that was once widely prescribed as an appetite suppressant to treat obesity. Fenfluramine is devoid of the psychomotor stimulant and abuse potential of D-amphetamine and interacts with the 5-hydroxytryptamine (serotonin, 5-HT) receptors to release 5-HT from neurons. Fenfluramine has been investigated as having anticonvulsive activity in the treatment of Dravet Syndrome, or severe myoclonic epilepsy in infancy, a rare and malignant epileptic syndrome. This type of epilepsy has an early onset in previously healthy children.

Anorectic treatment with fenfluramine has been associated with the development of cardiac valvulopathy and pulmonary hypertension, including the condition cardiac fibrosis which led to the withdrawal of fenfluramine from world-wide markets. Interaction of fenfluramine's major metabolite norfenfluramine with the 5-HT2B receptor is associated with heart valve hypertrophy. In the treatment of epilepsy, the known cardiovascular risks of fenfluramine are weighed against beneficial anticonvulsive activity.

SUMMARY

The present disclosure provides methods of preparing a fenfluramine active pharmaceutical ingredient. Aspects of the subject methods include hydrolyzing a 2-(3-(trifluoromethyl)phenyl)acetonitrile composition to produce a 2-(3-(trifluoromethyl)phenyl)acetic acid composition; reacting the 2-(3-(trifluoromethyl)phenyl)acetic acid composition with acetic anhydride and a catalyst to produce a 1-(3-(trifluoromethyl)phenyl)propan-2-one composition; and reductively aminating the 1-(3-(trifluoromethyl)phenyl)propan-2-one composition with ethylamine using a borohydride reducing agent to produce a fenfluramine composition.

Also provided are fenfluramine compositions and pharmaceutical ingredients produced according to the subject methods that include a reduced amount of one or more minor components such as impurities or reaction side products. In some cases, the compositions include a pharmaceutically acceptable salt of fenfluramine having less than 0.2% by weight in total of trifluoromethyl regioisomers. Also provided are pharmaceutical compositions including the subject fenfluramine compositions.

These and other objects, advantages, and features of the invention will become apparent to those persons skilled in the art upon reading the details of the metabolism-resistant fenfluramine analogs and methods of using the same as more fully described below.

BRIEF DESCRIPTION OF THE DRAWINGS

The present disclosure is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

DEFINITIONS

Figure 1:
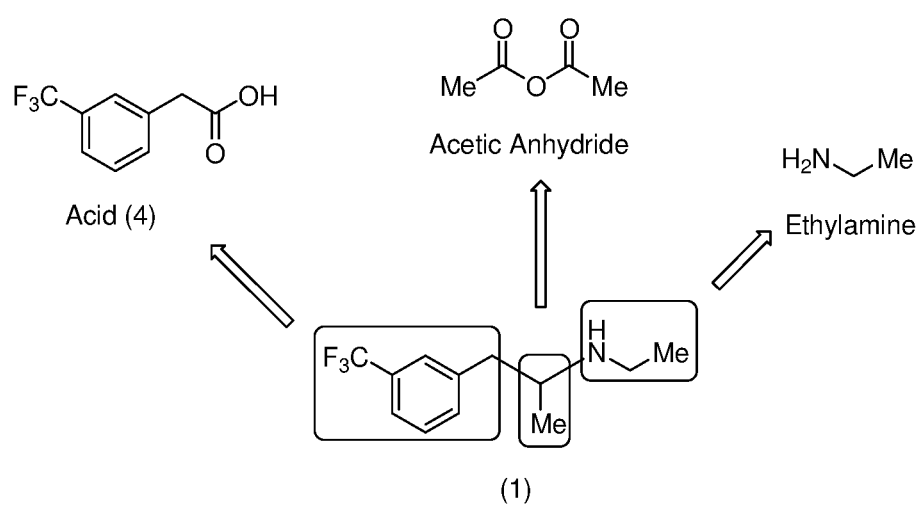
FIG. 1 illustrates the contributions of various precursor materials to the structure of fenfluramine (1) in an exemplary retrosynthetic analysis to acid (4).

As used herein, the term "subject" refers to a mammal. Exemplary mammals include, but are not limited to, humans, domestic animals (e.g., a dog, cat, or the like), farm animals (e.g., a cow, a sheep, a pig, a horse, or the like) or laboratory animals (e.g., a monkey, a rat, a mouse, a rabbit, a guinea pig, or the like). In certain embodiments, the subject is human. "Patient" refers to human and non-human subjects, especially mammalian subjects.

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. As used herein, the terms "treating," "treatment," "therapeutic," or "therapy" do not necessarily mean total cure or abolition of the disease or condition. Any alleviation of any undesired signs or symptoms of a disease or condition, to any extent can be considered treatment and/or therapy. Furthermore, treatment may include acts that may worsen the patient's overall feeling of well-being or appearance. "Treatment," as used herein, covers any treatment of a disease in a mammal, in some cases in a human, and includes: (a) preventing the disease or medical condition from occurring, such as, prophylactic treatment of a subject; (b) ameliorating the disease or medical condition, such as, eliminating or causing regression of the disease or medical condition in a patient; (c) suppressing the disease or medical condition, for example by, slowing or arresting the development of the disease or medical condition in a patient; or (d) alleviating a symptom of the disease or medical condition in a patient.

As used herein, the term pKa refers to the negative logarithm (p) of the acid dissociation constant (Ka) of an acid, and is equal to the pH value at which equal concentrations of the acid and its conjugate base form are present in solution.

The term "salt" refers to an ionic compound that result from the neutralization reaction of an acid and a base, and is composed of at least one cation (positively charged ion) and at least one anion (negative ion). In some embodiments, a salt is electrically neutral (without a net charge). Where applicable, the salt is a pharmaceutically acceptable salt, although this is not required for salts of intermediate compounds that are not intended for administration to a patient. By way of example, salts of the present compounds include those wherein the basic compound is protonated by an inorganic or organic acid to form a conjugate acid cation, with the conjugate base of the inorganic or organic acid as the anionic component of the salt. Salts of interest include, but are not limited to, hydrochloride salts. It is understood that for any of the structures depicted herein, such structures may also include any convenient salt forms.

The term "pharmaceutically acceptable" means approved by a regulatory agency of the Federal or a state government or listed in the U.S. Pharmacopeia or other generally recognized pharmacopeia for use in mammals, such as humans.

The term "pharmaceutically acceptable salt" means a salt which is acceptable for administration to a patient, such as a mammal (salts with counterions having acceptable mammalian safety for a given dosage regime). Such salts can be derived from pharmaceutically acceptable inorganic or organic bases and from pharmaceutically acceptable inorganic or organic acids. "Pharmaceutically acceptable salt" refers to pharmaceutically acceptable salts of a compound, which salts are derived from a variety of organic and inorganic counter ions well known in the art and include, by way of example only, sodium, and the like; and when the molecule contains a basic functionality, salts of organic or inorganic acids, such as hydrochloride, and the like. Pharmaceutically acceptable salts of interest include, but are not limited to, hydrochloride salts.

The term "active pharmaceutical ingredient" (API) refers to a substance or mixture of substances intended to be used in the manufacture of a drug product and that, when used in the production of a drug, becomes an active ingredient in the drug product. Such substances are intended to furnish pharmacological activity or other direct effect in the diagnosis, cure, mitigation, treatment or prevention of disease or to affect the structure and function of the body.

"Solvate" refers to a complex formed by combination of solvent molecules with molecules or ions of the solute. The solvent can be an organic compound, an inorganic compound, or a mixture of both. Some examples of solvents include, but are not limited to, methanol, N,N-dimethylformamide, tetrahydrofuran, dimethylsulfoxide, and water. When the solvent is water, the solvate formed is a hydrate.

"Stereoisomer" and "stereoisomers" refer to compounds that have same atomic connectivity but different atomic arrangement in space. Stereoisomers include cis-trans isomers, E and Z isomers, enantiomers, and diastereomers.

"Tautomer" refers to alternate forms of a molecule that differ only in electronic bonding of atoms and/or in the position of a proton, such as enol-keto and imine-enamine tautomers, or the tautomeric forms of heteroaryl groups containing a —N=C(H)—NH— ring atom arrangement, such as pyrazoles, imidazoles, benzimidazoles, triazoles, and tetrazoles. A person of ordinary skill in the art would recognize that other tautomeric arrangements of the groups described herein are possible.

It will be appreciated that the term "or a salt or solvate or stereoisomer thereof" is intended to include all permutations of salts, solvates and stereoisomers, such as a solvate of a pharmaceutically acceptable salt of a stereoisomer of subject compound. It is understood that the term "or a salt thereof" is intended to include all permutations of salts. It is understood that the term "or a pharmaceutically acceptable salt thereof" is intended to include all permutations of salts. It is understood that the term "or a solvate thereof" is intended to include all permutations of solvates. It is understood that the term "or a stereoisomer thereof" is intended to include all permutations of stereoisomers. It is understood that the term "or a tautomer thereof" is intended to include all permutations of tautomers. Thus for example it follows that it is intended to include a solvate of a pharmaceutically acceptable salt of a tautomer of a stereoisomer of subject compound.

"Pharmaceutically effective amount" and "therapeutically effective amount" refer to an amount of a compound sufficient to treat a specified disorder or disease or one or more of its symptoms and/or to prevent the occurrence of the disease or disorder. In reference to tumorigenic proliferative disorders, a pharmaceutically or therapeutically effective amount comprises an amount sufficient to, among other things, cause the tumor to shrink or decrease the growth rate of the tumor.

The term "vehicle" refers to a diluent, adjuvant, excipient, or carrier with which a compound of the invention is formulated for administration to a mammal.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supercedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a compound" includes a plurality of such compounds and reference to "the method" includes reference to one or more methods and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Before the present compounds and methods are described, it is to be understood that this invention is not limited to particular compounds and methods described, as such may, of course, vary. It is also to be understood that the terminology used herein is for the purpose of describing particular embodiments only, and is not intended to be limiting, since the scope of the present invention will be limited only by the appended claims.

DETAILED DESCRIPTION

As summarized above, the present disclosure provides methods of preparing a fenfluramine active pharmaceutical ingredient. Aspects of the present disclosure include fenfluramine compositions and pharmaceutical ingredients produced according to the subject methods where particular undesirable minor components of interest are substantially eliminated from the composition. The subject methods provide for a combination of steps to produce a crude composition that achieves a desirable minimum threshold for undesirable minor components, such as difficult to purify regioisomers, reaction side products and reagents. Active pharmaceutical ingredients for pharmaceutical formulations are prepared via controlled and reproducible methods to achieve highly pure compositions of active agent which provide high levels of safety, efficacy and quality in the resulting pharmaceutical formulations. In some cases, impurities or undesirable minor components in pharmaceutical compositions can cause drug product instability, loss of potency and toxicity. The substantial elimination of such minor components from the subject fenfluramine compositions provides a composition that is suitable for use in pharmaceutical compositions as the active pharmaceutical ingredient (API). The subject compositions can be produced efficiently with a reduced need for purification, eliminating purification steps or improving the outcome of method steps such as those steps involving removal of difficult to remove regioisomers of fenfluramine.

The term "composition", when used in the context of the subject methods, describes a material that is a starting material or a product of one or more steps of the subject methods and which can contain a mixture of components. The composition can be referred to by its predominant or target component, e.g., a fenfluramine composition. In general terms, a composition can include, in addition to a predominant target component, a mixture of other components, such as target isomers (e.g., a stereoisomer or regioisomer), impurities, reaction side products, starting materials, carry-over components from previous steps, reagents, solvents, and the like. As used herein, the term "crude composition" refers to the material produced in the performance of a chemical reaction procedure which has not been subjected to additional purification steps, e.g., separate post-reaction procedure steps, such as chromatography or recrystallization steps. In the preparation of a crude composition, the material can be subjected to simple steps, e.g., such as aqueous washes, solvent extractions and/or filtrations, which are considered an integral part of the reaction procedure, because such steps are commonly used to terminate a chemical reaction and/or to "work-up" a reaction product. Such reaction workup steps are not considered to be additional purification steps, as described above, but are merely part of the preparation of a crude composition.

Methods of Preparation of Fenfluramine Compositions

Aspects of the subject methods include preparation of a fenfluramine composition from a 1-(3-(trifluoromethyl)phenyl)-propan-2-one precursor composition via reductive amination (Scheme 1).

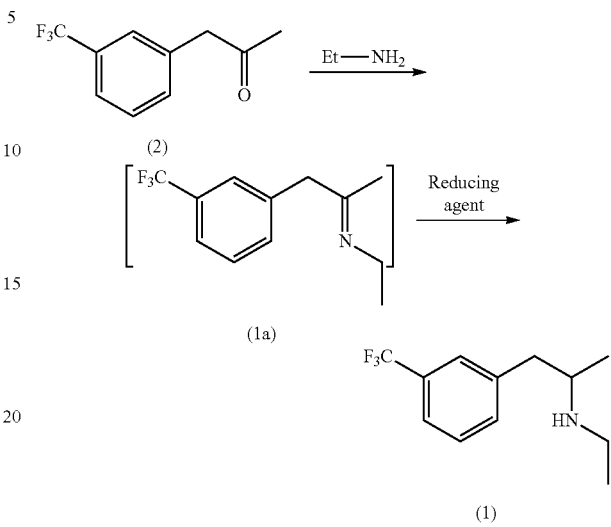

Scheme 1: Preparation of fenfluramine (1) from 1-(3-(trifluoromethyl)phenyl)-propan-2-one (2) via reductive amination.

Any convenient methods of reductive amination may be utilized to convert the ketone (2) to fenfluramine (1) via an imine intermediate (1a), e.g., via a Schiff base formed between ethylamine (e.g., Et-NH$_2$) and the ketone (2). Methods and reagents of interest include, but are not limited to, those methods and reagents described by Abdel-Magid et al. ("Reductive Amination of Aldehydes and Ketones with Sodium Triacetoxyborohydride. Studies on Direct and Indirect Reductive Amination Procedures", J. Org. Chem., 1996, 61 (11), pp 3849-3862. In some embodiments, the reductive amination reaction is performed under conditions that comprise contacting the 1-(3-(trifluoromethyl)phenyl)propan-2-one composition with a solution of 70% by weight of ethylamine/water and about 2.25 equivalents or more of sodium triacetoxyborohydride dissolved in methanol as solvent. In certain cases, the reaction (e.g., scheme 1) is performed at an industrial scale (e.g., as described herein). In certain instances, the yield of the reaction (e.g., scheme 1) is 80% or more, such as 85% or more, 90% or more, 95% or more, 98% or more or 99% or more.

Any convenient reducing agents can be used in the reductive amination step of the subject methods, e.g., to reduce the Schiff base intermediate to the secondary amine product, fenfluramine. In some instances, the reducing agent is a borohydride reducing agent. As used herein, the term "borohydride reducing agent" is meant to include any reducing agent that includes a BH$^-$ group, such as any convenient borohydride, cyanoborohydride or triacetoxyborohydride reducing agent having the formula MBR$_3$H, where each R is independently H, alkyl, cyano or acetoxy and M is a metal such as Na, Li or K. In some instances, the reducing agent is a cyanoborohydride reducing agent. In some instances, the reducing agent is a triacetoxyborohydride reducing agent. In some cases, the reducing agent is selected from sodium borohydride, sodium cyanoborohydride, sodium triacetoxyborohydride, lithium triethylborohydride, nickel borohydride, potassium borohydride and calcium borohydride. In certain instances the borohydride reducing agent is sodium triacetoxyborohydride (STAB; Na(CH$_3$COO)$_3$BH).

The 1-(3-(trifluoromethyl)phenyl)-propan-2-one (2) composition can be prepared from any convenient precursor composition. In some instances, the 1-(3-(trifluoromethyl)phenyl)-propan-2-one (2) composition is prepared from 2-(3-(trifluoromethyl)phenyl)acetic acid (4), e.g., according to Scheme 2 via a Daikin-West reaction. As such, aspects of the subject methods include reacting the 2-(3-(trifluoromethyl)phenyl)acetic acid composition with acetic anhydride and a catalyst to produce a 1-(3-(trifluoromethyl)phenyl)propan-2-one composition.

Scheme 2: Preparation of ketone (2) from acid (4) via a Daikin-West reaction.

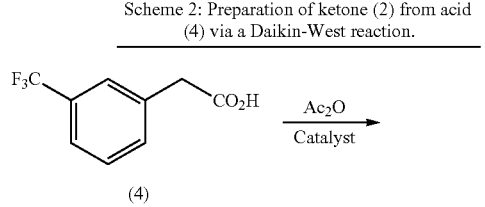

(4)

(2)

The Daikin-west reaction provides for the conversion of an enolizable carboxylic acid to a corresponding methyl ketone by reaction with an acetylation agent (e.g., acetic anhydride and a catalyst). In some cases, the catalyst is a nucleophilic catalyst. Any convenient nucleophilic catalyst can be used in junction with acetic anhydride in the preparation of ketone (2) via Scheme 2. In some embodiments, the catalyst is N-methylimidazole (i.e., 1-methylimidazole). The catalyst and the acetic anhydride may combine to form an acetylating agent in situ. It is understood that a variety of other acetylating agents and precursor reagents for producing an acetylation agent in situ may be utilized in the reaction step. In some cases, the method step includes addition of a pre-formed acetylating agent directly to the acid (4). Methods and reagents of interest that find use in the preparation of ketone (2) include, but are not limited to, those described by Buchanan in "The Dakin-West reaction", Chem. Soc. Rev., 1988, 17, 91-109. In some embodiments, the reaction is performed under conditions that include contacting the 2-(3-(trifluoromethyl)phenyl)acetic acid composition with about 0.5 equivalents of 1-methylimidazole and about 5 equivalents or more of acetic anhydride, optionally in a solvent. In certain instances, the yield of the reaction (e.g., scheme 2) is 80% or more, such as 85% or more, 90% or more, 95% or more, 98% or more or 99% or more.

The ketone (2) can be optionally purified before use in the step outlined in Scheme 1 using any convenient method. In some cases, the ketone (2) is purified via formation of a bisulfite adduct. As used here, the terms "bisulfite adduct" and "bisulfite addition compound" are used interchangeably to refer to the product of addition of a bisulfite ion to a ketone compound. The bisulfite adduct of ketone (2) can be a solid which provides for a more facile removal of impurities from the adduct composition than is possible from the corresponding parent ketone composition.

Scheme 3: Purification of ketone (2) via formation of a ketone bisulfite adduct (3).

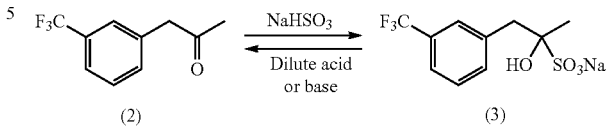

(2)  (3)

Aspects of the subject methods include a combination of the individual steps described herein, e.g., a combination of steps as step forth in Scheme 4. Before or after any of the steps described an optional additional purification step (e.g., crystallization step) may be performed. In some embodiments, the method includes reacting a 2-(3-(trifluoromethyl)phenyl)acetic acid composition with acetic anhydride and a catalyst to produce a 1-(3-(trifluoromethyl)phenyl)propan-2-one composition; and reductively aminating the 1-(3-(trifluoromethyl)phenyl)propan-2-one composition with ethylamine using a borohydride reducing agent to produce a fenfluramine composition.

Scheme 4: Preparation of fenflurtamine (1) from acid (4) via ketone (2)

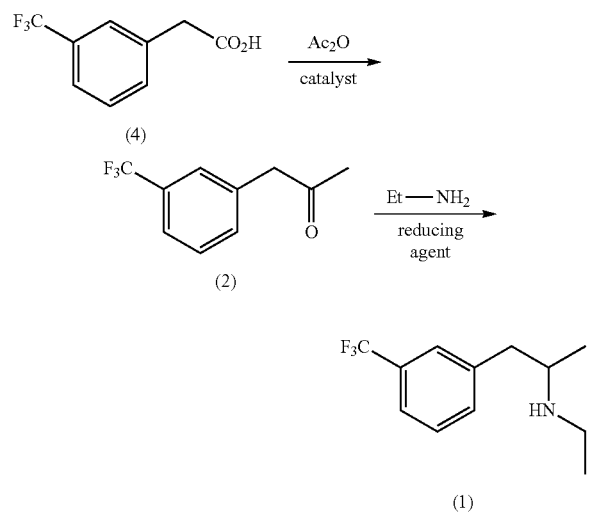

(4)

(2)

(1)

The 2-(3-(trifluoromethyl)phenyl)acetic acid (4) composition can be prepared from any convenient precursor composition. In some instances, the 2-(3-(trifluoromethyl)phenyl)acetic acid composition is prepared from a 2-(3-(trifluoromethyl)phenyl)acetonitrile composition, e.g., according to the reaction of Scheme 5. As such, aspects of the subject method includes hydrolyzing a 2-(3-(trifluoromethyl)phenyl)acetonitrile (5) composition to produce a 2-(3-(trifluoromethyl)phenyl)acetic acid (4) composition.

Scheme 5: Hydrolysis of nitrile (5) to acid (4).

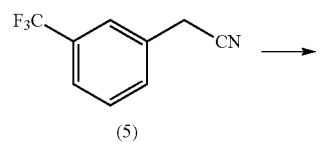

(5)

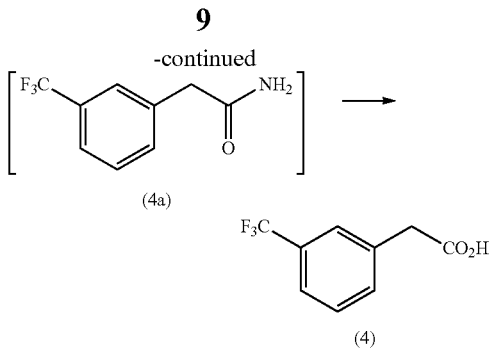

Hydrolysis of the nitrile (5) to the acid (4) can be achieved using any convenient methods. In some cases, the hydrolysis of the nitrile (5) is achieved via acid-catalyzed hydrolysis. In certain instances, the hydrolysis of the nitrile (5) is achieved via base-catalyzed hydrolysis. Hydrolysis may proceed via an amide intermediate (4a) under aqueous acidic conditions. In some embodiments of the method, hydrolysis of the nitrile (5) to the acid (4) is performed under aqueous acidic conditions. In certain instances, the yield of the reaction (e.g., scheme 5) is 80% or more, such as 85% or more, 90% or more, 95% or more, 98% or more or 99% or more.

In some cases, the method includes hydrolyzing a 2-(3-(trifluoromethyl)phenyl)acetonitrile (5) composition to produce a 2-(3-(trifluoromethyl)phenyl)acetic acid (4) composition; and reacting a 2-(3-(trifluoromethyl)phenyl)acetic acid (4) composition with acetic anhydride and a catalyst to produce a 1-(3-(trifluoromethyl)phenyl)propan-2-one (2) composition (see e.g., Scheme 6).

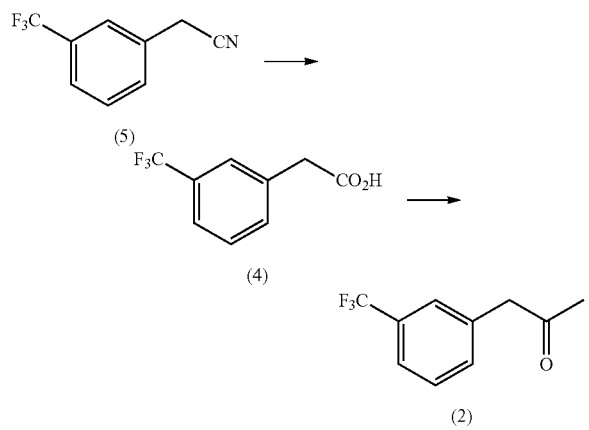

Aspects of the subject methods include a combination of the steps described herein e.g., a combination of steps as described in Scheme 7. Before or after any of the steps described, an optional additional purification step (e.g., crystallization step) may be performed. In some embodiments, the method includes hydrolyzing a 2-(3-(trifluoromethyl)phenyl)acetonitrile (5) composition to produce a 2-(3-(trifluoromethyl)phenyl)acetic acid (4) composition; reacting the 2-(3-(trifluoromethyl)phenyl)acetic acid (4) composition with acetic anhydride and a catalyst to produce a 1-(3-(trifluoromethyl)phenyl)propan-2-one (2) composition; and reductively aminating the 1-(3-(trifluoromethyl)phenyl)propan-2-one (2) composition with ethylamine using a borohydride reducing agent to produce a fenfluramine (1) composition.

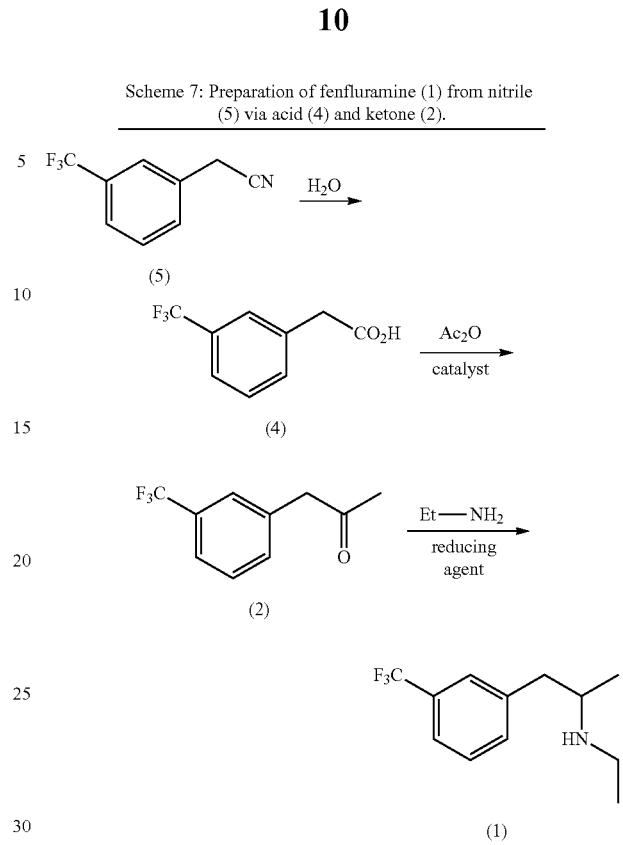

In some embodiments of the method, the fenfluramine composition (e.g., a crude fenfluramine composition) that is produced has the following profile: 80% or more by weight of fenfluramine or a salt thereof, such as 90% or more, 95% or more, 96% or more, 97% or more, 98% or more, 99% or more, 99.5% or more, or even more by weight of the fenfluramine or salt thereof; 1% or less by weight of 2-fenfluramine regioisomer or a salt thereof, such as 0.5% or less, 0.2% or less, or 0.1% or less, 0.05% or less, 0.01% or less, or even less by weight of 2-fenfluramine regioisomer or a salt thereof; 1% or less by weight of 4-fenfluramine regioisomer or a salt thereof, such as 0.5% or less, 0.2% or less, or 0.1% or less, 0.05% or less, 0.01% or less, or even less by weight of 4-fenfluramine regioisomer or a salt thereof; and 10% or less by weight of fenfluramine reduced alcohol side product, such as 5% or less, 2% or less, or 1% or less, 0.5% or less, 0.1% or less by weight of fenfluramine reduced alcohol side product.

In some embodiments, the method is a method of preparing fenfluramine free base. As such, the fenfluramine composition can include fenfluramine free base. Fenfluramine free base that is prepared according to the subject methods may be converted to any convenient salt form, e.g., a salt of the conjugate acid of the secondary amino group of fenfluramine (fenfluramine.H$^+$X$^-$), using a variety of methods. The formation of a fenfluramine salt can be performed as part of the reductive amination step of Scheme 1 (e.g., in situ), or salt formation can be performed in an optional subsequent step. In some cases, the salt form is a pharmaceutically acceptable salt of fenfluramine. Salts of interest include, but are not limited to, a hydrochloride salt. In certain instances, the pharmaceutically acceptable salt form of fenfluramine is a hydrochloride salt.

Scheme 8: Preparation of a salt of fenfluramine.

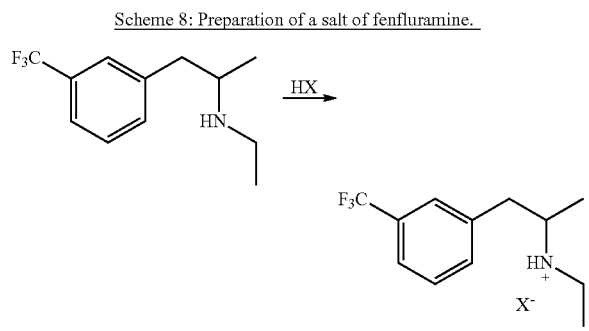

The subject methods provide for substantial elimination of one or more undesirable minor components from the crude fenfluramine composition or fenfluramine salt composition, such that final additional purification steps can be achieved easily with high efficiency and/or high yield to produce a high quality active pharmaceutical composition.

One or more additional purification steps may be performed on the crude fenfluramine composition (e.g., that includes a free base or a salt form of fenfluramine) prepared according to the subject methods. In certain instances, the purification step includes crystallization of fenfluramine or the salt form of fenfluramine from the crude composition. The crystalline fenfluramine salt form can have a desirable polymorphism, high crystallinity, water solubility and/or stability. In some cases, the subject methods provide for a crystalline fenfluramine hydrochloride salt that is a single polymorph that is free-flowing, non-hygroscopic and having a high melting temperature.

In some embodiments of the method, the composition produced comprises a pharmaceutically acceptable salt of fenfluramine and has following purity profile: 90% or more of the pharmaceutically acceptable salt of fenfluramine, such as 95% or more, 96% or more, 97% or more, 98% or more, 99% or more, 99.5% or more, 99.8% or more, 99.9% or more, or even more by weight of the pharmaceutically acceptable salt of fenfluramine; 1% or less by weight of 2-fenfluramine; 1% or less by weight of 2-fenfluramine regioisomer or a salt thereof, such as 0.5% or less, 0.2% or less, or 0.1% or less, 0.05% or less, 0.01% or less, or even less by weight of 2-fenfluramine regioisomer or a salt thereof; 1% or less by weight of 4-fenfluramine regioisomer or a salt thereof, such as 0.5% or less, 0.2% or less, or 0.1% or less, 0.05% or less, 0.01% or less, or even less by weight of 4-fenfluramine regioisomer or a salt thereof; and 5% or less by weight of fenfluramine reduced alcohol side product, such as 3% or less, 2% or less, or 1% or less, 0.5% or less, 0.1% or less by weight of fenfluramine reduced alcohol side product. In certain embodiments, the composition produced according to the subject methods is a fenfluramine active pharmaceutical ingredient comprising a pharmaceutically acceptable salt of fenfluramine and having 0.2% or less by weight in total of trifluoromethyl regioisomers, such as 0.1% or less, 0.05% or less, 0.03% or less, 0.01% or less, or even less by weight of trifluoromethyl regioisomers. In certain embodiments, the fenfluramine active pharmaceutical ingredient has a purity profile comprising: at least 90% (e.g., at least 95%, at least 96%, at least 97%, at least 98%, at least 99%, at least 99.5%, at least 99.8%, at least 99.9%, or more) by weight of a pharmaceutically acceptable salt of fenfluramine; less than 0.2% by weight (e.g., less than 0.1%, less than 0.05%, less than 0.03%, less than 0.01% by weight) of 2-fenfluramine; less than 0.2% by weight (e.g., less than 0.1%, less than 0.05%, less than 0.03%, less than 0.01% by weight) of 4-fenfluramine; and less than 1% by weight (e.g., less than 0.5%, less than 0.3%, less than 0.1%, less than 0.05% by weight) of fenfluramine alcohol.

The subject methods provide for the preparation of a racemic mixture of enantiomers of fenfluramine. The enantiomers of fenfluramine may be referred to as: dexfenfluramine (i.e., (S)-N-ethyl-1-[3-(trifluoromethyl)phenyl]-propan-2-amine, (+)-fenfluramine or (S)-fenfluramine); and levofenfluramine (i.e., (2R)—N-ethyl-1-[3-(trifluoromethyl)phenyl]-2-propanamine, (−)-fenfluramine or (R)-fenfluramine). The fenfluramine enantiomers or salts thereof can be separated from each other using any convenient methods. Methods of interest for separation and purification of fenfluramine enantiomers include, but are not limited to, chiral resolution by crystallization and chiral column chromatography. As such, in some embodiments, the method further includes performing a chiral separation of a racemic fenfluramine composition, or a salt thereof, to produce a non-racemic fenfluramine composition comprising a predominant stereoisomer of fenfluramine. By non-racemic is meant a composition having an enantiomeric excess of at least 50%, such as at least 60%, at least 70%, at least 80%, at least 90%, at least 95% or at least 99% of one stereoisomer, e.g., a predominant stereoisomer. As used herein, the term "predominant stereoisomer" is meant to encompass a composition including only one stereoisomer or a composition that includes stereoisomer mixtures.

In some cases, the active pharmaceutical ingredient composition is a non-racemic composition including (S)-fenfluramine or a pharmaceutically acceptable salt thereof as the predominant stereoisomer. In some cases, the active pharmaceutical ingredient composition is a non-racemic composition including (R)-fenfluramine or a pharmaceutically acceptable salt thereof as the predominant stereoisomer. In some cases, the non-racemic composition that is produced includes only one stereoisomer.

Minor Components

As summarized above, the compositions of the subject methods, e.g., starting material compositions, intermediate compositions and final fenfluramine compositions may provide for the substantial elimination of one or more minor components, which is achieved by the subject methods to produce compositions that find use as an active pharmaceutical ingredient (API), or precursor thereof, for pharmaceutical compositions. The subject methods provide for the substantial elimination of undesirable minor components is a variety of ways. As used herein, by "substantially eliminate" is meant the achievement of a desirable minimum threshold for a minor component of interest, such that the minor component, if present, is present at a level at or below the threshold. As used herein, the term "substantially devoid" refers to a composition where a minor component of interest is either not present or is present at a level at or below the minimum threshold. The desirable minimum threshold for a minor component of interest may vary according to the nature of the component and whether the composition in an intermediate composition or a fenfluramine composition of interest. In some instances, the desirable minimum threshold of a minor component of interest that is achieved is 10% by weight or less, such as 5% or less, 4% or less, or 3% or less, 2% or less, 1% or less 0.5% or less, 0.4% or less, 0.3% or less, 0.2% or less, 0.15% or less 0.1% or less, 0.09% or less, 0.08% or less, 0.07% or less, 0.06% or less, 0.05% or less, 0.03% or less, or 0.01% or less. In certain instances, the minor component of interest is completely eliminated from the compositions of interest, i.e., the composition is devoid of the minor component (e.g., is not detected or is below the detectable limit of the component).

In some cases, the particular combination of steps utilized in the subject method works to eliminate a minor component of interest. In certain instances, purification of an intermediate composition, e.g., via crystallization, achieves substantial elimination of a minor component that would be difficult to remove if the minor component, e.g., a regioisomer, was carried forward to a later step in the synthesis. In certain instances, the performance of a particular method step provides for a selectivity of reaction, whereby a minor component of interest is not transformed by the reaction conditions as the major component is, and thus may be more easily removed, e.g., as a regioisomer of the starting material rather than the product of a reaction or particular method step. In some cases, the particular combination of steps utilized in the subject methods avoids the use of one or more chemical reagents, solvents and/or reactants that is required via conventional methods and which are lead to undesirable minor components in the product compositions. Minor components of interest which may be substantially eliminated include but are not limited to, product isomers, side products, aldehydes, ketones, peroxides, metals (e.g., heavy metal and metal catalysts), nitrate/nitrite, trace solvents, and organic acids. Various minor components and details of their substantial elimination from the subject compositions are now described in greater below. Minor components of interest that may be substantially eliminated according to the subject methods include any impurities, by-products, starting materials and minor components described herein, including but not limited to, acetate impurity, dimer impurity, Acetamide impurity, 1-((3-trifluoromethyl)phenyl)acetone, fenfluramine regioisomers, Fenfluramine Alcohol, N-(3-(trifluoromethyl)-benzyl)ethanamine, norfenfluramine and any one of the impurities of Table 7.

Regioisomers

In some instances, a regioisomer of fenfluramine, or a precursor thereof, can be present as a minor component of any one of the subject compositions that find use in the subject methods. Fenfluramine and synthetic precursors thereof can include a 3-trifluoromethyl substituted phenyl group. As used here, the terms, "trifluoromethyl regioisomer" and "trifluoromethyl-phenyl regioisomer" are used interchangeably to refer to an isomer(s) of fenfluramine, or any one of the synthetic precursors described herein, where the trifluoromethyl substituent is located at either the 2-position or the 4-position of the substituted phenyl ring rather than at the 3-position corresponding to fenfluramine. As such, the terms "2-trifluoromethyl regioisomer" and "4-trifluoromethyl regioisomer" can be used herein to describe particular minor components of any intermediate composition or final composition that finds use in the subject methods.

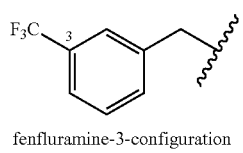

fenfluramine-3-configuration

-continued

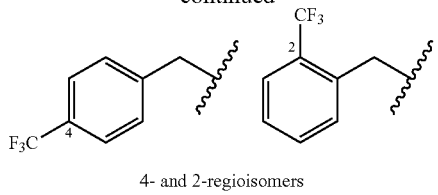

4- and 2-regioisomers

The 2-(3-(trifluoromethyl)phenyl)acetonitrile composition starting material of the subject methods can include regioisomers. In some cases, the regioisomers derive from the method of preparation of the 2-(3-(trifluoromethyl)phenyl)acetonitrile from trifluoromethyl benzene. In some instances, the 2-(3-(trifluoromethyl)phenyl)acetonitrile composition comprises at least 0.2% by weight, such as at least 0.3%, at least 0.4%, at least 0.5%, at least 1.0%, at least 1.5%, at least 2%, at least 3%, at least 4%, at least 5%, at least 10%, or even more by weight of trifluoromethyl-phenyl regioisomers (e.g., a combined total of 2-(2-(trifluoromethyl)phenyl)acetonitrile and 2-(4-(trifluoromethyl)phenyl)acetonitrile). In some instances, the 2-(3-(trifluoromethyl)phenyl)acetonitrile composition comprises at least 0.2% by weight, such as at least 0.3%, at least 0.4%, at least 0.5%, at least 1.0%, at least 1.5%, at least 2%, at least 3%, at least 4%, at least 5%, at least 10%, or even more by weight of 2-(4-(trifluoromethyl)phenyl)acetonitrile). In some instances, the 2-(3-(trifluoromethyl)phenyl)acetonitrile composition comprises at least 0.2% by weight, such as at least 0.3%, at least 0.4%, at least 0.5%, at least 1.0%, at least 1.5%, at least 2%, at least 3%, at least 4%, at least 5%, at least 10%, or even more by weight of 2-(2-(trifluoromethyl)phenyl)acetonitrile). In certain instances, the 2-(3-(trifluoromethyl)phenyl)acetonitrile composition includes minor regioisomer components that are carried over to the next composition, e.g., a 2-(3-(trifluoromethyl)phenyl)acetic acid composition. As such, the 2-(3-(trifluoromethyl)phenyl)acetic acid composition produced as an intermediate in the subject method can also include regioisomers (e.g., 2-(2-(trifluoromethyl)phenyl)acetic acid and 2-(4-(trifluoromethyl)phenyl)acetic acid) at the same levels as are described herein for the 2-(3-(trifluoromethyl)phenyl)acetonitrile composition starting material.

The subject methods provide for removal of 2- and/or 4-regioisomers as minor components of an intermediate composition in various ways. In some embodiments, the method includes purifying the 2-(3-(trifluoromethyl)phenyl)acetic acid composition to produce a composition substantially devoid of one or both of the trifluoromethyl-phenyl regioisomers. In certain instances, the composition is also substantially devoid of benzaldehyde that is present in the acetonitrile starting material. In certain instances, the composition is also substantially devoid of trifluoromethyl-benzaldehyde that is present in the acetonitrile starting material. In certain instances, purifying the 2-(3-(trifluoromethyl)phenyl)acetic acid composition to remove a portion or all of the minor regioisomer components can be achieved via crystallization of the 2-(3-(trifluoromethyl)phenyl)acetic acid. As used herein, the term "substantially devoid of a trifluoromethyl-phenyl regioisomer" means less than 0.5% by weight, such as less than 0.4%, less than 0.3%, less than 0.2%, less than 0.1%, less than 0.09%, less than 0.08%, less than 0.07%, less than 0.06%, less than 0.05%, less than 0.03%, or even less. Any convenient methods of crystallization or recrystallization can be utilized in the subject methods.

After purification, e.g., crystallization, of the 2-(3-(trifluoromethyl)phenyl)acetic acid composition, the composition can include less than 0.5% by weight, such as less than 0.4%, less than 0.3%, less than 0.2%, less than 0.1%, less than 0.09%, less than 0.08%, less than 0.07%, less than 0.06%, less than 0.05%, less than 0.03%, or even less of 2-(2-(trifluoromethyl)phenyl)acetic acid. After purification, e.g., crystallization, of the 2-(3-(trifluoromethyl)phenyl)acetic acid composition, the composition can include less than 0.5% by weight, such as less than 0.4%, less than 0.3%, less than 0.2%, less than 0.1%, less than 0.09%, less than 0.08%, less than 0.07%, less than 0.06%, less than 0.05%, less than 0.03%, or even less of 2-(4-(trifluoromethyl)phenyl)acetic acid. After purification, e.g., crystallization, of the 2-(3-(trifluoromethyl)phenyl)acetic acid composition, the composition can include less than 0.5% by weight, such as less than 0.4%, less than 0.3%, less than 0.2%, less than 0.1%, less than 0.09%, less than 0.08%, less than 0.07%, less than 0.06%, less than 0.05%, less than 0.03%, or even less of benzaldehyde.

In some embodiments, the method includes reacting the 2-(3-(trifluoromethyl)phenyl)acetic acid composition with acetic anhydride and a catalyst to produce a 1-(3-(trifluoromethyl)phenyl)propan-2-one composition, where the 2-(3-(trifluoromethyl)phenyl)acetic acid is selectively converted to the ketone in the presence of unreacted 2-(2-(trifluoromethyl)phenyl)acetic acid. The subject method provides for facile removal of 2-regioisomer that is present because this regioisomer is not carried through the reaction at the same rate as the target 3-trifluoromethyl compound. In some cases, the method further comprises removing unreacted 2-(2-(trifluoromethyl)phenyl)acetic acid regioisomer from the 1-(3-(trifluoromethyl)phenyl)propan-2-one composition. As such, in some instances, the crude 1-(3-(trifluoromethyl)phenyl)propan-2-one composition is substantially devoid (e.g., includes less than 0.5% by weight, such as less than 0.4%, less than 0.3%, less than 0.2%, less than 0.1%, less than 0.09%, less than 0.08%, less than 0.07%, less than 0.06%, less than 0.05%, less than 0.03%, or even less) of 2-regioisomer of the ketone product.

Removal of regioisomer minor components present in the acetonitrile starting material may be achieved in stages during performance of the synthetic method. In some embodiments, a first portion of the regioisomer minor components present in the starting material are removed from the 2-(3-(trifluoromethyl)phenyl)acetic acid composition, e.g., via crystallization. In certain instance, a second portion of the regioisomer minor components present that are carried through intermediate compositions of the subject method are removed via selective reaction of the 2-(3-(trifluoromethyl)phenyl)acetic acid, e.g., as described herein. In certain instances, a third portion of the regioisomer minor components present that are carried through intermediate compositions of the subject method are removed via purification of a fenfluramine composition.

Benzaldehyde and Trifluorobenzaldehyde

Depending on the method of preparation of the 2-(3-(trifluoromethyl)phenyl)acetonitrile, the starting material composition can include benzaldehyde or trifluorobenzaldehyde as a minor component. It is undesirable to have such a minor component present in a pharmaceutical active ingredient. In some instances, the 2-(3-(trifluoromethyl)phenyl)acetonitrile composition comprises at least 0.2% by weight, such as at least 0.3%, at least 0.4%, at least 0.5%, at least 1.0%, at least 2%, at least 5%, at least 10%, or even more by weight of benzaldehyde or trifluorobenzaldehyde as a minor component. In some instances, any benzaldehyde or trifluorobenzaldehyde that is present as a minor component is substantially removed during purification, e.g., crystallization, of the 2-(3-(trifluoromethyl)phenyl)acetic acid from the composition as described herein. In certain instances, benzaldehyde is not present in the 2-(3-(trifluoromethyl)phenyl)-acetonitrile starting material composition due to its method of preparation.

Method of Preparation of Ketone (2)

Figure 4:
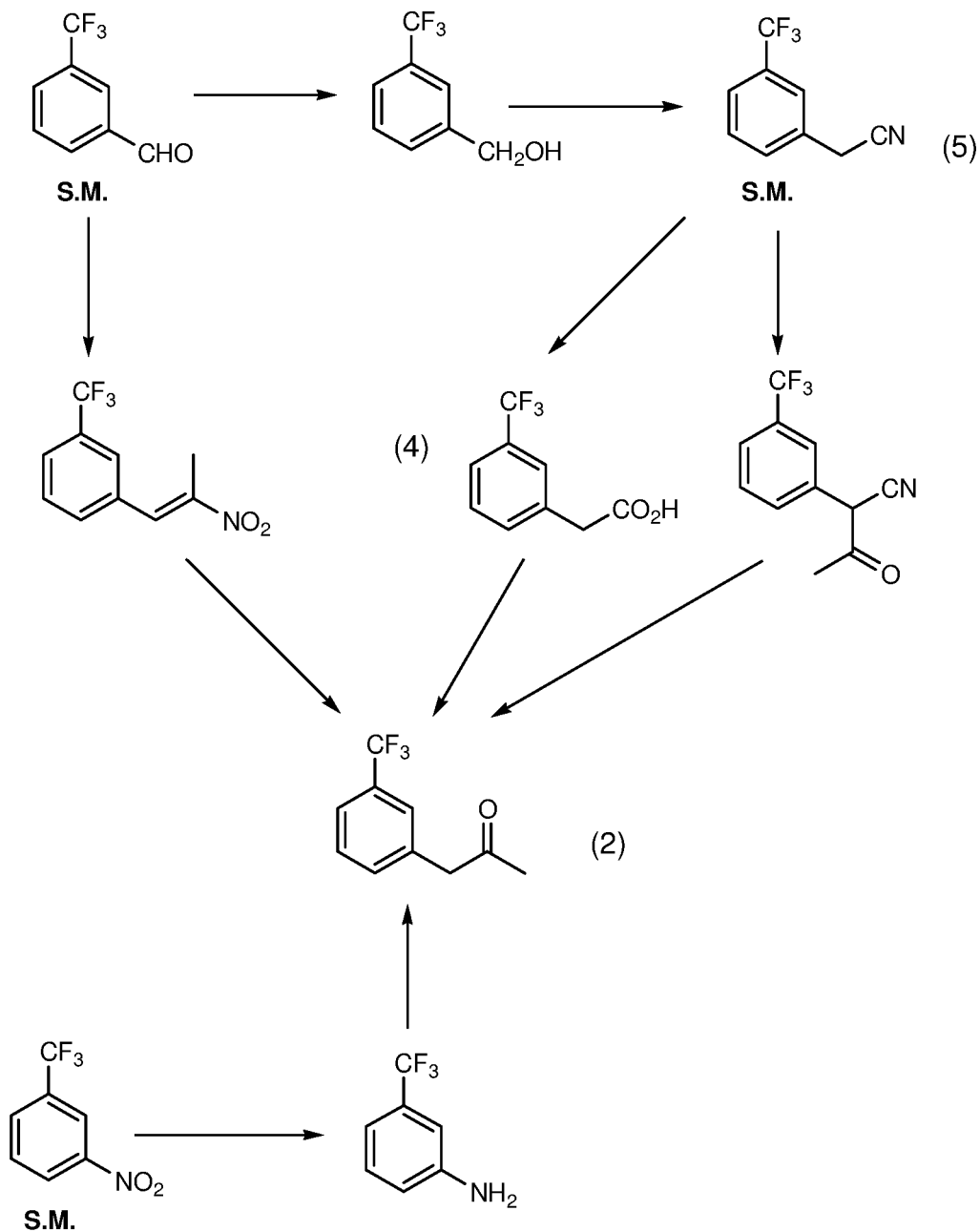
FIG. 4 illustrates a variety of synthetic pathways for preparation of ketone (2). An exemplary method that finds use in the subject methods is preparation of ketone (2) from nitrile (5) via acid (4).

The subject methods can include a particular combination of steps for preparation of the ketone (2) that provide for one or more advantages over other possible methods. FIG. 4 illustrates a variety of synthetic pathways that could be used for preparation of ketone (2). In certain cases, the particular method that finds use in the subject methods is preparation of ketone (2) from nitrile (5) via acid (4).

In the subject methods, minor components (e.g., acetate and dimer impurities) formed during the Dakin-West reaction (e.g., as described in Scheme 2) can be subsequently substantially eliminated. In certain cases, these minor components are removed using a distillation procedure. In certain instances, these minor components are removed via a procedure including isolation of the product ketone (2) as the bisulfite salt (e.g., as described herein). The acetate and dimer impurities are shown below.

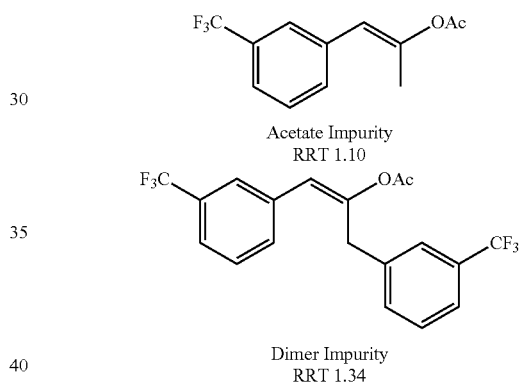

Acetate Impurity
RRT 1.10

Dimer Impurity
RRT 1.34

In some instances, use of the bisulfite isolation procedure improves the purity of the ketone by a factor of at least 30% (e.g., at least 40%, at least 50%, or more) by removing these and other impurities. In some embodiments, the subject methods provide for substantial elimination of the acetate impurity from the ketone (2) composition. In some embodiments, the subject methods provide for substantial elimination of the dimer impurity from the ketone (2) composition.

Figure 5:
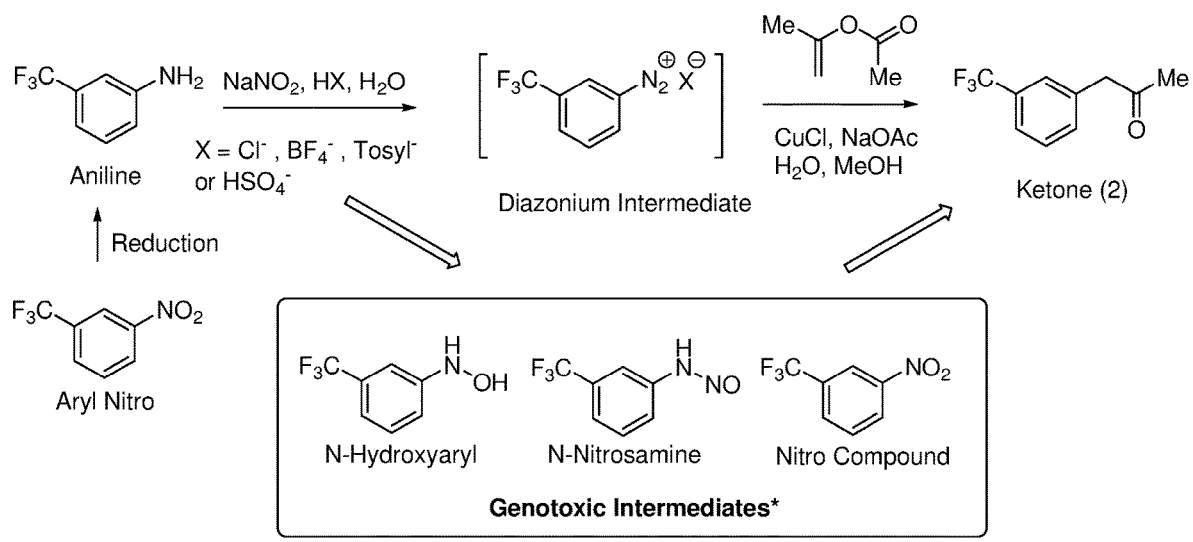
FIG. 5 illustrates a route to prepare ketone (2) from an Aryl Nitro starting material via a diazonium intermediate. The diazonium route has a disadvantage due to the potential formation of genotoxic intermediates shown as boxed compounds (e.g., N-hydroxyaryl, N-nitrosamine and Nitro compound).

FIG. 5 illustrates a diazonium route to prepare ketone (2) from an Aryl Nitro starting material. The diazonium route has a disadvantage due to the potential formation of genotoxic intermediates shown as boxed compounds (e.g., N-hydroxyaryl, N-nitrosamine and Nitro compound). In some cases, removal of such impurities and/or demonstrating their absence is costly and time consuming and sometimes difficult to achieve technically. Aspects of the subject methods include a synthetic route that substantially eliminates the undesirable minor components that are possible via the route shown in FIG. 5, thereby circumventing the potential for such toxic and/or undesirable compounds to be present in the subject compositions.

In some cases, the subject methods provide for elimination of isomer (e.g., a regioisomer) by-products of the 3-trifluoroaniline starting material described in FIG. 5. Such by-products can be present in 3-trifluoroaniline compositions, carried through synthetic steps, and be difficult to substantially eliminate from downstream compositions. In some instances of the subject methods, crystallization of the Acid (4) resulting from hydrolysis of the nitrile (5) provides crystalline Acid (4) which provides for a facile removal of such isomers early in synthesis. Removing impurities and/or undesirable isomers early in a synthesis can be preferred, especially if such impurities are carried through to final product compositions, as purification of a final product at the end of a synthesis is more costly (e.g., in losses of valuable product) and impacts cost of goods more greatly than removing such minor components early in synthesis before raw materials are invested along the process.

Eliminated Toxic Reagents

The subject methods include a particular synthetic pathway and combination of chemical reactions (e.g., as described above) that provides for the elimination of certain undesirable reagents and/or solvents (e.g., Class 1 or Class 2 solvents that have known or they have strongly suspected carcinogenic activity and/or are environmental hazards). Class 1 and 2 solvents of interest which can be eliminated from the fenfluramine composition by practicing the subject methods include, but are not limited to, any solvent listed on the International Conference on Harmonization (ICH) Q3C list and guidance for Industry (February 2012, Revision 2, US Dept. HHS), such as acetonitrile, benzene and substituted benzenes, carbon tetrachloride, chloroform, cyclohexane, 1,2-dichloroethane, 1,1-dichloroethane, 1,2-dimethoxyethane, DMF, 1,4-dioxane, methanol, methylbutyl ketone, N-methylpyrrolidinone, pyridine, toluene, 1,1,1-trichloroethane, 1,1,2-trichloroethene, and xylene. The subject methods also provide for the elimination of a variety of undesirable and/or toxic reagents from the fenfluramine composition that is produced by practicing the subject methods. For example, by including a reductive amination step according to the method depicted in Scheme 1, alternative synthetic pathways that require use of potentially toxic metal catalysts are avoided. By eliminating the use of such reagents and/or solvents from the synthetic pathway of the subject methods, potentially toxic minor components are eliminated from the fenfluramine composition. As such, the subject fenfluramine composition can be referred to as being substantially devoid of the minor component of interest. In some instances, one or more potential heavy metal components such as Pb, As, Cd, Hg, Pb, Co, Mo, Se and V are substantially eliminated. In certain instances, one or more Class 1 solvents are substantially eliminated (e.g., below an acceptable threshold limit as adopted under ICH Q3C). In certain instances, benzene solvent is substantially eliminated, e.g., below a concentration limit of 2 ppm. In certain instances, carbon tetrachloride solvent is substantially eliminated, e.g., below a concentration limit of 4 ppm. In certain instances, 1,2-dichloroethane solvent is substantially eliminated, e.g., below a concentration limit of 5 ppm. In certain instances, 1,2-dichloroethane solvent is substantially eliminated, e.g., below a concentration limit of 8 ppm. In certain instances, 1,1,1-trichloroethane solvent is substantially eliminated, e.g., below a concentration limit of 1500 ppm. A minor component can be considered completely eliminated from the subject compositions when the fenfluramine is produced via a method where the minor component is not used in any synthetic step or present in a starting material.

Fenfluramine Alcohol

As used herein, the terms "fenfluramine alcohol" and "reduced alcohol side product" are used interchangeable to refer to the product of ketone reduction to alcohol that can occur in the reductive amination step of Scheme 1, depicted below.

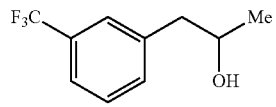 [SMILES: CC(O)Cc1cccc(C(F)(F)F)c1]

The subject methods provide for substantial elimination of fenfluramine alcohol from the subject compositions. In some instances, the crude fenfluramine composition has less than 10% by weight of the reduced alcohol side product, such as less than 9%, less than 8%, less than 7%, less than 6%, less than 5%, less than 4%, less than 3%, less than 2%, less than 1%, less than 0.9%, less than 0.8%, less than 0.7%, less than 0.6%, less than 0.5%, less than 0.4%, less than 0.3%, less than 0.2%, less than 0.1%, less than 0.05% or even less. In some instances, the crude fenfluramine composition has 10% or less by weight of the reduced alcohol side product, such as 9% or less, 8% or less, 7% or less, 6% or less, 5% or less, 4% or less, 3% or less, 2% or less, 1% or less, 0.9% or less, 0.8% or less, 0.7% or less, 0.6% or less, 0.5% or less, 0.2% or less, 0.1% or less, 0.05% or less, or even less.

Norfenfluramine

Norfenfluramine is a potential impurity of compositions that include fenfluramine. The subject methods provide for substantial elimination of norfenfluramine from the subject compositions. In some instances, the crude fenfluramine composition has less than 10% by weight of norfenfluramine, such as less than 9%, less than 8%, less than 7%, less than 6%, less than 5%, less than 4%, less than 3%, less than 2%, less than 1%, less than 0.9%, less than 0.8%, less than 0.7%, less than 0.6%, less than 0.5%, less than 0.4%, less than 0.3%, less than 0.2%, less than 0.1%, less than 0.05% or even less. In some instances, the crude fenfluramine composition includes has 10% or less by weight of norfenfluramine, such as 9% or less, 8% or less, 7% or less, 6% or less, 5% or less, 4% or less, 3% or less, 2% or less, 1% or less, 0.9% or less, 0.8% or less, 0.7% or less, 0.6% or less, 0.5% or less, 0.4% or less, 0.3% or less, 0.2% or less, 0.1% or less, 0.05% or less, or even less.

Methods of Use

Fenfluramine and the fenfluramine compositions described herein may be employed in a variety of methods. Aspects of the present disclosure include a method that includes administering to a subject in need thereof a therapeutically effective amount of a fenfluramine pharmaceutical composition (e.g., as described herein) to treat or prevent a disease or condition of interest. By "therapeutically effective amount" is meant the concentration of a compound that is sufficient to elicit the desired biological effect (e.g., treatment or prevention of epilepsy). Diseases and conditions of interest include, but are not limited to, epilepsy, a neurological related diseases, obesity and obesity related diseases.

In some embodiments, the subject method includes administering to a subject a subject composition to treat a neurological related disease. Neurological related diseases of interest include, but are not limited to, epilepsy, and Dravet syndrome. In certain embodiments, the subject is human. In certain instances, the subject suffers from Dravet syndrome. In certain embodiments, the compound is administered as a pharmaceutical preparation.

Thus, according to a still further aspect of the present disclosure, there is provided a method of stimulating one or more 5-HT receptors in the brain of a patient by administering an effective dose of a fenfluramine composition to said patient, said one or more 5-HT receptors being selected from one or more of $5\text{-}HT_1$, $5\text{-}HT_{1A}$, $5\text{-}HT_{1B}$, $5\text{-}HT_{1C}$, $5\text{-}HT_{1D}$, $5\text{-}HT_{1E}$, $5\text{-}HT_{1F}$, $5\text{-}HT_2$, $5\text{-}HT_{2A}$, $5\text{-}HT_{2B}$, $5\text{-}HT_{2C}$, $5\text{-}HT_3$, $5\text{-}HT_4$, $5\text{-}HT_5$, $5\text{-}HT_{5A}$, $5\text{-}HT_{5B}$, $5\text{-}HT_6$, and $5\text{-}HT_7$ amongst others. In some instances, the 5-HT receptor is $5\text{-}HT_{2B}$. In certain embodiments of this aspect of the invention, the patient has been diagnosed with Dravet Syndrome. In some instances, the method is a method of treating Dravet Syndrome that includes of stimulating one or more 5-HT receptors in the brain of a patient by administering an effective dose of a fenfluramine composition to said patient, said one or more 5-HT receptors being selected from one or more of $5\text{-}HT_{1D}$, $5\text{-}HT_{2A}$ and $5\text{-}HT_{2C}$, among others.

There are a number of genetic mutations that are indicative of Dravet Syndrome. Mutations in the SCN1A (such as partial or total deletion mutations, truncating mutations and/or missense mutations e.g. in the voltage or pore regions S4 to S6), SCN1B (such as the region encoding the sodium channel ß1 subunit), SCN2A, SCN3A, SCN8A, SCN9A, GABRG2 (such as the region encoding the γ2 subunit), GABRD (such as the region encoding the δ subunit) and/or PCDH19 genes have been linked to Dravet Syndrome.

Thus, according to a further aspect of the present invention, there is provided a method of treating a patient that exhibits a mutation in one, some or all of the above genes by administering to that patient an effective dose of a fenfluramine comp. In certain embodiments of this aspect of the invention, the patient has been diagnosed with Dravet Syndrome.

In embodiments of the invention, any effective dose of the fenfluramine composition can be employed. However, surprisingly low doses of fenfluramine compositions are found by the inventors to be efficacious, particularly for inhibiting or eliminating seizures in epilepsy patients. Thus, in some cases, in a preferred embodiment of the invention, a daily dose of less than about 10 mg/kg/day such as, less than about 9 mg/kg/day, less than about 8 mg/kg/day, less than about 7 mg/kg/day, less than about 6 mg/kg/day, less than about 5 mg/kg/day, less than about 4 mg/kg/day, less than about 3 mg/kg/day, less than about 2 mg/kg/day, less than about 1 mg/kg/day, such as about 1.0 mg/kg/day, about 0.9 mg/kg/day, about 0.8 mg/kg/day, about 0.7 mg/kg/day, about 0.6 mg/kg/day, about 0.5 mg/kg/day, about 0.45 mg/kg/day, about 0.4 mg/kg/day, about 0.3 mg/kg/day, about 0.25 mg/kg/day or about 0.2 mg/kg/day to about 0.1 mg/kg/day, about 0.05 mg/kg/day, or about 0.01 mg/kg/day is employed. Put differently, a preferred dose is less than about 10 mg/kg/day to about 0.01 mg/kg/day. In some cases, the dose is less than about 5 mg/kg/day to about 0.1 mg/kg/day, such as less than about 5 mg/kg/day to about 0.5, mg/kg/day, less than about 4 mg/kg/day to about 0.5 mg/kg/day, less than about 3 mg/kg/day to about 0.5 mg/kg/day, less than about 2 mg/kg/day to about 0.5 mg/kg/day, or less than about 1.7 mg/kg/day to about 0.9 mg/kg/day.

As indicated above the dosing is based on the weight of the patient. However, for convenience the dosing amounts may be preset such as in the amount of 1 mg, 2.5 mg, 5 mg, 10 mg, 15 mg, 20 mg, 30 mg, 40 mg, or 50 mg. In certain instances, the dosing amount may be preset such as in the amount of about 0.25 mg to about 5 mg, such as about 0.5 mg, about 0.75 mg, about 1.0 mg, about 1.25 mg, about 1.5 mg, about 1.75 mg, about 2.0 mg, about 2.25 mg, about 2.5 mg, about 2.75 mg, about 3.0 mg, about 3.25 mg, about 3.5 mg, about 3.75 mg, about 4.0 mg, about 4.25 mg, about 4.5 mg, about 4.75 mg, or about 5.0 mg. The dosing amounts described herein may be administered one or more times daily to provide for a daily dosing amount, such as once daily, twice daily, three times daily, or four or more times daily, etc. In certain embodiments, the dosing amount is a daily dose of 30 mg or less, such as 30 mg, about 29 mg, about 28 mg, about 27 mg, about 26 mg, about 25 mg, about 24 mg, about 23 mg, about 22 mg, about 21 mg, about 20 mg, about 19 mg, about 18 mg, about 17 mg, about 16 mg, about 15 mg, about 14 mg, about 13 mg, about 12 mg, about 11 mg, about 10 mg, about 9 mg, about 8 mg, about 7 mg, about 6 mg, about 5 mg, about 4 mg, about 3 mg, about 2 mg, or about 1 mg. In general the smallest dose which is effective should be used for the particular patient. In some cases, the dose is generally well below the dosing used in weight loss.

Administration of the subject pharmaceutical compositions may be systemic or local. In certain embodiments, administration to a mammal will result in systemic release of fenfluramine (for example, into the bloodstream). Methods of administration may include enteral routes, such as oral, buccal, sublingual, and rectal; topical administration, such as transdermal and intradermal; and parenteral administration. Suitable parenteral routes include injection via a hypodermic needle or catheter, for example, intravenous, intramuscular, subcutaneous, intradermal, intraperitoneal, intraarterial, intraventricular, intrathecal, and intracameral injection and non-injection routes, such as intravaginal rectal, or nasal administration. In certain embodiments, the compositions of the present disclosure are administered orally. In certain embodiments, it may be desirable to administer one or more compounds of the invention locally to the area in need of treatment. This may be achieved, for example, by local infusion during, topical application, by injection, by means of a catheter, by means of a suppository, or by means of an implant, said implant being of a porous, non-porous, or gelatinous material, including membranes, such as sialastic membranes, or fibers.

The dose of fenfluramine administered in the methods of the present invention can be formulated in any pharmaceutically acceptable dosage form including, but not limited to oral dosage forms such as tablets including orally disintegrating tablets, capsules, lozenges, oral solutions or syrups, oral emulsions, oral gels, oral films, buccal liquids, powder e.g. for suspension, and the like; injectable dosage forms; transdermal dosage forms such as transdermal patches, ointments, creams; inhaled dosage forms; and/or nasally, rectally, vaginally administered dosage forms. Such dosage forms can be formulated for once a day administration, or for multiple daily administrations (e.g. 2, 3 or 4 times a day administration).

In some embodiments, the subject method includes administering to a subject an appetite suppressing amount of the subject compound to treat obesity. Any of the methods of administration and dosage forms of the subject compositions may be utilized in treating obesity.

Combination therapy includes administration of a single pharmaceutical dosage formulation which contains the subject composition and one or more additional agents; as well as administration of the subject composition and one or more additional agent(s) in its own separate pharmaceutical dosage formulation. For example, a subject composition and an additional agent active with appetite suppressing activity (e.g., phentermine or topiramate) can be administered to the patient together in a single dosage composition such as a combined formulation, or each agent can be administered in a separate dosage formulation. Where separate dosage formulations are used, the subject composition and one or more additional agents can be administered concurrently, or at separately staggered times, e.g., sequentially.

In some embodiments, the subject method is an in vitro method that includes contacting a sample with a subject composition. The protocols that may be employed in these methods are numerous, and include but are not limited to, serotonin release assays from neuronal cells, cell-free assays, binding assays (e.g., 5HT2B receptor binding assays); cellular assays in which a cellular phenotype is measured, e.g., gene expression assays; and assays that involve a particular animal model for a condition of interest (e.g., Dravet syndrome).

Pharmaceutical Preparations

Also provided are pharmaceutical preparations that include fenfluramine active pharmaceutical ingredient compositions prepared according to the subject methods. Pharmaceutical preparations are compositions that include a compound (either alone or in the presence of one or more additional active agents) present in a pharmaceutically acceptable vehicle. In some embodiments, the pharmaceutical composition includes a fenfluramine composition (e.g., as described herein) formulated in a pharmaceutically acceptable excipient.

The choice of excipient will be determined in part by the particular compound, as well as by the particular method used to administer the composition. Accordingly, there is a wide variety of suitable formulations of the pharmaceutical composition of the present invention.

The dosage form of fenfluramine employed in the methods of the present invention can be prepared by combining the fenfluramine composition with one or more pharmaceutically acceptable diluents, carriers, adjuvants, and the like in a manner known to those skilled in the art of pharmaceutical formulation.

The subject compositions can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

In some embodiments, formulations suitable for oral administration can include (a) liquid solutions, such as an effective amount of the compound dissolved in diluents, such as water, or saline; (b) capsules, sachets or tablets, each containing a predetermined amount of the active ingredient (fenfluramine), as solids or granules; (c) suspensions in an appropriate liquid; and (d) suitable emulsions. Tablet forms can include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible excipients. Lozenge forms can include the active ingredient in a flavor, usually sucrose and acacia or tragacanth, as well as pastilles including the active ingredient in an inert base, such as gelatin and glycerin, or sucrose and acacia, emulsions, gels, and the like containing, in addition to the active ingredient, such excipients as are described herein.

The subject formulations can be made into aerosol formulations to be administered via inhalation. These aerosol formulations can be placed into pressurized acceptable propellants, such as dichlorodifluoromethane, propane, nitrogen, and the like. They may also be formulated as pharmaceuticals for non-pressured preparations such as for use in a nebulizer or an atomizer.

In some embodiments, formulations suitable for parenteral administration include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

Formulations suitable for topical administration may be presented as creams, gels, pastes, or foams, containing, in addition to the active ingredient, such carriers as are appropriate. In some embodiments the topical formulation contains one or more components selected from a structuring agent, a thickener or gelling agent, and an emollient or lubricant. Frequently employed structuring agents include long chain alcohols, such as stearyl alcohol, and glyceryl ethers or esters and oligo(ethylene oxide) ethers or esters thereof. Thickeners and gelling agents include, for example, polymers of acrylic or methacrylic acid and esters thereof, polyacrylamides, and naturally occurring thickeners such as agar, carrageenan, gelatin, and guar gum. Examples of emollients include triglyceride esters, fatty acid esters and amides, waxes such as beeswax, spermaceti, or carnauba wax, phospholipids such as lecithin, and sterols and fatty acid esters thereof. The topical formulations may further include other components, e.g., astringents, fragrances, pigments, skin penetration enhancing agents, sunscreens (e.g., sunblocking agents), etc.

For an oral pharmaceutical formulation, suitable excipients include pharmaceutical grades of carriers such as mannitol, lactose, glucose, sucrose, starch, cellulose, gelatin, magnesium stearate, sodium saccharine, and/or magnesium carbonate. For use in oral liquid formulations, the composition may be prepared as a solution, suspension, emulsion, or syrup, being supplied either in solid or liquid form suitable for hydration in an aqueous carrier, such as, for example, aqueous saline, aqueous dextrose, glycerol, or ethanol, preferably water or normal saline. If desired, the composition may also contain minor amounts of non-toxic auxiliary substances such as wetting agents, emulsifying agents, or buffers.

By way of illustration, the fenfluramine composition can be admixed with conventional pharmaceutically acceptable carriers and excipients (i.e., vehicles) and used in the form of aqueous solutions, tablets, capsules, elixirs, suspensions, syrups, wafers, and the like. Such pharmaceutical compositions contain, in certain embodiments, from about 0.1% to about 90% by weight of the active compound, and more generally from about 1% to about 30% by weight of the active compound. The pharmaceutical compositions may contain common carriers and excipients, such as corn starch or gelatin, lactose, dextrose, sucrose, microcrystalline cellulose, kaolin, mannitol, dicalcium phosphate, sodium chloride, and alginic acid. Disintegrators commonly used in the formulations of this invention include croscarmellose, microcrystalline cellulose, corn starch, sodium starch glycolate and alginic acid.

Particular formulations of the present disclosure are in a liquid form. The liquid may be a solution or suspension and may be an oral solution or syrup which is included in a bottle with a pipette which is graduated in terms of milligram amounts which will be obtained in a given volume of solution. The liquid solution makes it possible to adjust the solution for small children which can be administered anywhere from 0.5 mg to 15 mg and any amount between in half milligram increments and thus administered in 0.5, 1.0, 1.5, 2.0 mg, etc.

A liquid composition will generally consist of a suspension or solution of the compound or pharmaceutically acceptable salt in a suitable liquid carrier(s), for example, ethanol, glycerine, sorbitol, non-aqueous solvent such as polyethylene glycol, oils or water, with a suspending agent, preservative, surfactant, wetting agent, flavoring or coloring agent. Alternatively, a liquid formulation can be prepared from a reconstitutable powder.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric. By "average" is meant the arithmetic mean. Standard abbreviations may be used, e.g., s or sec, second(s); min, minute(s); h or hr, hour(s); aa, amino acid(s); i.m., intramuscular(ly); i.p., intraperitoneal (ly); s.c., subcutaneous(ly); and the like.

General Synthetic Procedures

Many general references providing commonly known chemical synthetic schemes and conditions useful for synthesizing the disclosed compounds are available (see, e.g., Smith and March, March's Advanced Organic Chemistry: Reactions, Mechanisms, and Structure, Fifth Edition, Wiley-Interscience, 2001; or Vogel, A Textbook of Practical Organic Chemistry, Including Qualitative Organic Analysis, Fourth Edition, New York: Longman, 1978).

Compounds as described herein can be purified by any purification protocol known in the art, including chromatography, such as HPLC, preparative thin layer chromatography, flash column chromatography and ion exchange chromatography. Any suitable stationary phase can be used, including normal and reversed phases as well as ionic resins. In certain embodiments, the disclosed compounds are purified via silica gel and/or alumina chromatography. See, e.g., Introduction to Modern Liquid Chromatography, 2nd Edition, ed. L. R. Snyder and J. J. Kirkland, John Wiley and Sons, 1979; and Thin Layer Chromatography, ed E. Stahl, Springer-Verlag, New York, 1969.

During any of the processes for preparation of the subject compounds, it may be necessary and/or desirable to protect sensitive or reactive groups on any of the molecules concerned. This may be achieved by means of conventional protecting groups as described in standard works, such as J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie", Houben-Weyl, $4^{th}$ edition, Vol. 15/1, Georg Thieme Verlag, Stuttgart 1974, in H.-D. Jakubke and H. Jescheit, "Aminosauren, Peptide, Protein", Verlag Chemie, Weinheim, Deerfield Beach, and Basel 1982, and/or in Jochen Lehmann, "Chemie der Kohlenhydrate: Monosaccharide and Derivate", Georg Thieme Verlag, Stuttgart 1974. The protecting groups may be removed at a convenient subsequent stage using methods known from the art.

The subject compounds can be synthesized via a variety of different synthetic routes using commercially available starting materials and/or starting materials prepared by conventional synthetic methods. A variety of examples of synthetic routes that can be used to synthesize the compounds disclosed herein are described in the schemes below.

Example 1

1. Fenfluramine Nomenclature & Structure

Chemical Abstract Service (CAS) Registry Number (RN): 404-82-0 (HCl Salt), 458-24-2 (Parent Free Base)

Chemical Name: N-ethyl-α-methyl-3-(trifluoromethyl)-benzeneethanamine hydrochloride (1:1). Other Names: Fenfluramine HCl, DL-Fenfluramine, (±)-Fenfluramine Structure of hydrochloride salt:

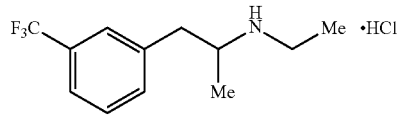 [SMILES: Cl ; CCNC(C)Cc1cccc(C(F)(F)F)c1]

Stereochemistry: Fenfluramine HCl has one chiral center and is being developed as the racemate and contains dexfenfluramine and levofenfluramine Molecular Formula of hydrochloride salt: C12H16F3N.HCl Molecular Mass/Weight: 267.72 g/mol 2. General Properties Table 1 summarizes the chemical and physical properties of Fenfluramine HCl.

TABLE 1

| General Properties of Fenfluramine HCl Drug Substance | |
|---|---|
| Property | Result |
| Appearance (color, physical form) | White to off-white powder |
| DSC (melting point)[a] | 170° C. (melt/sublimation) |

TABLE 1-continued

General Properties of Fenfluramine HCl Drug Substance

| | | | |
|---|---|---|---|
| TGA | Onset 147° C. | | |
| | 0.03% at 150° C. | | |
| | 91% at 220° C. (evaporation) | | |
| pKa (water) | 10.15-10.38 | | |

| | | Solubility (mg/mL) | |
|---|---|---|---|
| | Resultant pH | 25° C. | 37° C. |
| Solubility (Aqueous) | pH 6.69 (water) | 54.13 | 71.22 |
| | pH 1.73 buffer | 25.34 | 53.68 |
| | pH 3.43 buffer | 29.50 | 61.97 |
| | pH 6.41 buffer | 37.42 | 95.60 |
| | 0.9% NaCl (water) | 22.98 | — |

| | Solvent | Solubility 25° C. (mg/mL) |
|---|---|---|
| Solubility (Organic Solvents) | Ethanol | 150 |
| | Dichloromethane | 30-35 |
| | Ethyl Acetate, Tetrahydrofuran, Toluene, Acetonitrile | 1-5 mg |

| | |
|---|---|
| UV Absorption | Maxima: 210, 265 nm |
| Solution pH (water) | 6.69 |
| Hygroscopicity (Dynamic Vapor Sorption (DVS) | @30% RH: ~0.05% |
| | @60% RH: ~0.07% |
| | @90% RH: ~0.20%$^{a)}$ |
| Polymorphism | Fenfluramine HCl has been consistently isolated as a single crystalline Form 1 as determined by DSC and x-ray powder diffraction (XRPD) |
| Solvation/Hydration | Fenfluramine HCl is isolated as a nonhydrated, nonsolvated solid |
| Solution Stability | 8 weeks @ pH 6.7 phosphate buffer medium at 40° C. and 60° C. using concentrations of 0.5, 2.5 and 5.0 mg/ml. All conditions, no new impurities >0.1% by HPLC. |
| Solid Stability | 8 weeks @ 40° C., 60° C. and 80° C. 7 days at 150° C. All conditions, no new impurities >0.1% by HPLC. |

3. Synthesis of Fenfluramine Drug Substance

Scheme 3.1 shows a 2-step route of synthesis used to manufacture initial clinical supplies of Fenfluramine HCl from ketone (2). The batch size is 4 kg performed in laboratory glassware (kilo lab). No chromatography is required and the process steps are amenable to scale-up. In process 1 there is one isolated intermediate Fenfluramine Free Base (1) starting from commercially supplied 1-(3-(trifluoromethyl)phenyl) acetone (Ketone 2). All steps are conducted under cGMPs starting from Ketone (2).

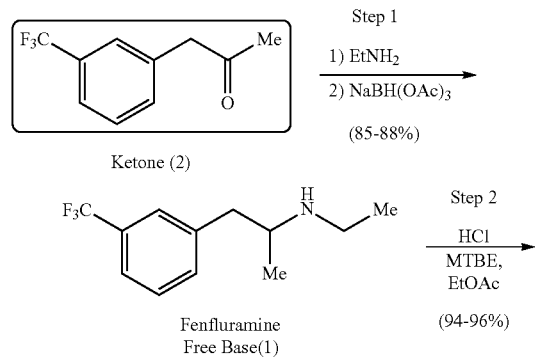

Scheme 3.1 Fenfluramine HCl Synthesiss Flow Scheme (Route 1)

-continued

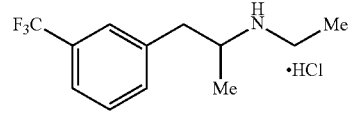

Fenfluramine HCl

MTBE = Metyl-tert-Butyl Ether, EtOAc = Ethyl Acetate.

Scheme 3.2 shows a 4-step route of synthesis to Fenfluramine HCl that can be used for commercial supply. Route 2 utilizes the same 2-step process used by Route 1 to convert Ketone (2) to Fenfluramine HCl with the exception that Ketone (2) is synthesized under cGMP conditions starting from 3-(Trifluoromethyl)-phenyl acetic acid (Acid 4). Bisulfate Complex (3) is an isolatable solid and can be purified before decomplexation to Ketone (2). In-situ intermediates which are oils are shown in brackets. Batch sizes of 10 Kg are performed. Commercial batch sizes of 20 kg are performed in fixed pilot plant equipment. Steps 1-2 of Scheme 3.2 to manufacture Ketone (2) have been demonstrated on a 100 g scale to provide high purity ketone (2) of >99.8% (GC & HPLC). Conversion of Ketone (2) to Fenfluramine using either Route 1 or 2 has provided similar purity profiles.

Scheme 3.2 Fenfluramine HCl Synthesis Flow Scheme (Route 2)

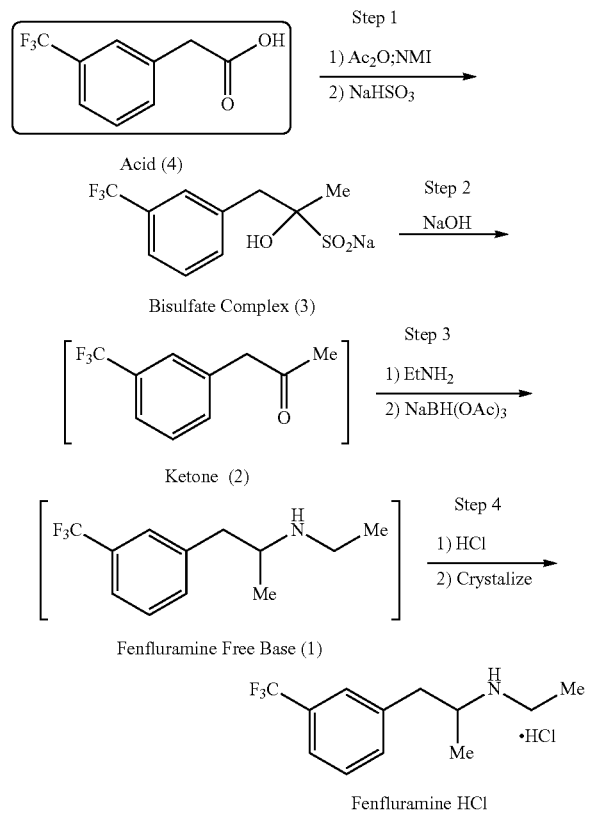

Starting materials are designated by enclosed boxes. Bracketed and non bracketed compounds respectively indicate proposed in-situ and isolated intermediates. NMI=N-Methyl Imidazole.

4.1. Narrative Description (Route 1)

Step 1: Reductive Amination (Preparation of Fenfluramine Free Base 1)

A solution of ethylamine, water, methanol, and 1-(3-(trifluoromethyl)phenyl) acetone (Ketone 2) was treated with sodium triacetoxyborohydride and stirred for 16 h at 25° C. at which time HPLC analysis (IPC-1; In Process Control No. 1) showed the reaction to be complete and sodium hydroxide solution was added until pH>10. Toluene was added and the phases separated, and the aqueous phase (IPC-2) and organic phase (IPC-3) are checked for remaining Fenfluramine and Fenfluramine alcohol and the organic phase was reduced. Purified water was added and the pH adjusted to <2 using conc. HCl and the phases were separated. The aqueous phase was washed with toluene and the toluene phase (IPC-4) and the aqueous phase (IPC-5) was checked for Fenfluramine and Fenfluramine alcohol content. The aqueous phase containing product is pH adjusted to >10 using sodium hydroxide solution. The basic aqueous phase was extracted with MTBE until removal of Fenfluramine from the aqueous phase was observed by HPLC (<0.5 mg/ml) (IPC-6). The organic phase was dried over sodium sulfate and filtered. The filtrate was concentrated in vacuo to give the intermediate product Fenfluramine Free Base 1 as a pale yellow oil tested per specifications described herein which showed by NMR the material to contain 2.93% toluene giving an active yield of 88.3% with a purity of 98.23% by HPLC (0.67% Fenfluramine alcohol).

Step 2: Salt Formation (Preparation of Fenfluramine HCl)

To a flask was charged ethanol and acetyl chloride. The solution was stirred slowly overnight before ethyl acetate was added. The HCl in ethyl acetate solution formed was polish filtered into a clean carboy and retained for later use. To a vessel was added Fenfluramine free base 1 and MTBE. The Fenfluramine solution in MTBE was collected in two carboys before the vessel was cleaned and checked for particulate residue. The Fenfluramine solution was polish filtered into a vessel and cooled and HCl in ethyl acetate solution was added giving a final pH of 6-7. The batch was stirred for 1 h and filtered. The product was dried under vacuum at 40° C. The product (96.52% yield) was tested per IPC-7 had a purity of 99.75% by HPLC and GC headspace analysis showed MTBE (800 ppm) and EtOAc (150 ppm) to be present. The product was then tested per specifications shown herein.

4.2. Narrative Description (Route 2)

Step 1: Preparation of Ketone Bisulfite Adduct

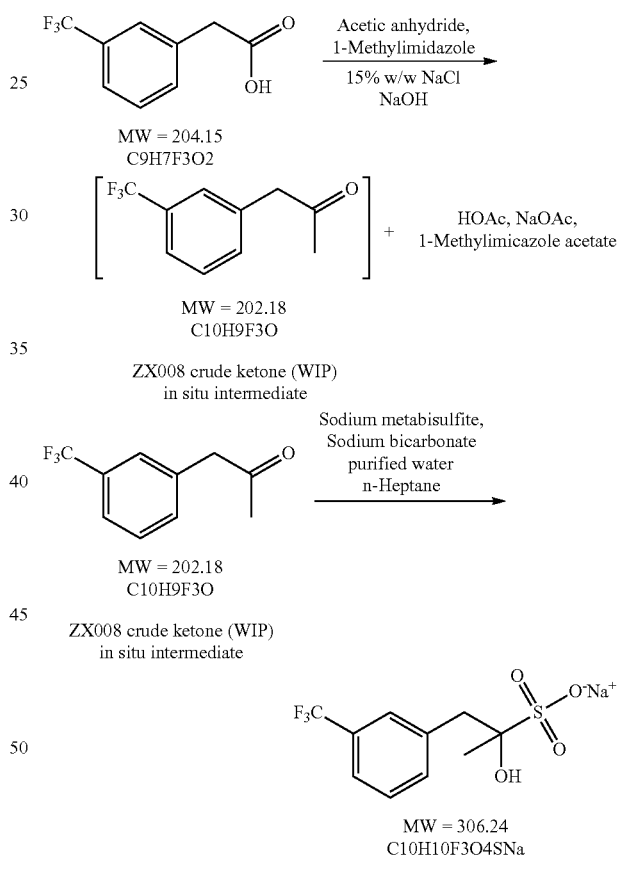

Procedure: Charge acetic anhydride, (2.8 vol, 3.0 wt, 5.0 eq.) to a vessel and commence stirring. Cool the solution to −5 to 5° C., targeting −4° C. Charge 1-methylimidazole, (0.2 vol, 0.21 wt, 0.5 eq.) to the mixture at −5 to 5° C. Caution: very exothermic. If necessary, adjust the temperature to 0 to 5° C. Charge ZX008 acid, (1.00 wt, 1.0 eq.) to the mixture at 0 to 5° C. Caution: exothermic. Stir the mixture at 0 to 5° C. until ≤2.1% area ZX008 acid by HPLC analysis, typically 7 to 9 hours. Charge 15% w/w sodium chloride solution (2.0 vol) to the mixture at 0 to 5° C., 60 to 90 minutes. Caution:

very exothermic which will be slightly delayed. Warm the mixture to 18 to 23° C. over 45 to 60 minutes and continue stirring for a further 30 to 45 minutes at 18 to 23° C. Charge TBME, (5.0 vol, 3.7 wt) to the mixture and stir for 10 to 15 minutes at 18 to 23° C. Separate the aqueous layer and retain the organic layer. Back-extract the aqueous layer with TBME, (2×3.0 vol, 2×2.2 wt) at 18 to 23° C. retaining each organic layer. Adjust the pH of the combined organic layer to pH 6.5 to 9.0, targeting 7.0 by charging 20% w/w sodium hydroxide solution (5.3 to 8.3 vol) at 18 to 23° C. Caution: exothermic. Separate the aqueous layer and retain the organic layer. Wash the organic layer with 4% w/w sodium hydrogen carbonate solution (2×3.0 vol) at 18 to 23° C. Determine the residual ZX008 acid content in the organic layer by HPLC analysis, pass criterion ≤0.10% area ZX008 acid. Wash the organic layer with purified water, (2×3.0 vol) at 18 to 23° C. Concentrate the organic layer under reduced pressure to ca. 2 vol at 40 to 45° C., targeting 43° C.

Determine the w/w assay of ZX008 ketone (WIP) in the mixture by 1H-NMR analysis for information only and calculate the contained yield of ZX008 ketone (WIP) in the mixture. Note: This step can be removed from the process since the process is robust and consistently delivers 80 to 90% th yield. The achieved yield was factored into the charges of the subsequent steps.

Charge n-heptane, (4.0 vol, 2.7 wt) to the mixture at 40 to 45° C., targeting 43° C. Concentrate the mixture to ca. 2 vol at 40 to 45° C., targeting 43° C. Determine the TBME content in the mixture by 1H-NMR analysis, (pass criterion ≤5.0% w/w TBME vs. ZX008 ketone). Charge n-heptane, (2.4 vol, 1.6 wt) at 40 to 45° C., targeting 43° C., vessel A. To vessel B, charge sodium metabisulfite, (0.82 wt, 0.88 eq.) at 18 to 23° C. To vessel B, charge a solution of sodium hydrogen carbonate, (0.16 wt, 0.4 eq.) in purified water, code RM0120 (2.0 vol) at 18 to 23° C. followed by a line rinse with purified water, code RM0120 (0.4 vol) at 18 to 23° C. Caution: gas evolution. Heat the contents of vessel B to 40 to 45° C., targeting 43° C. Charge the contents from vessel A to vessel B followed by a line rinse with n-heptane, (0.8 vol, 0.5 wt) at 40 to 45° C., targeting 43° C. Stir the mixture for 1 to 1.5 hours at 40 to 45° C., targeting 43° C. Charge n-heptane, code RM0174 (3.2 vol, 2.2 wt) to the mixture with the temperature being allowed to cool to 18 to 45° C. at the end of the addition. Cool the mixture to 18 to 23° C. at approximately constant rate over 45 to 60 minutes. Stir the mixture at 18 to 23° C. for 1.5 to 2 hours.

Sample the mixture to determine the residual ZX008 ketone content by 1H-NMR analysis, (pass criterion ≤10.0% mol, target 5.0% mol ZX008 ketone vs. ZX008 ketone bisulfite adduct). Filter the mixture and slurry wash the filter-cake with n-heptane, (2×2.0 vol, 2×1.4 wt) at 18 to 23° C. Dry the solid at up to 23° C. until the water content is ≤10.0% w/w water by KF analysis according to AKX reagent. At least 16 hours. Determine the w/w assay of the isolated ZX008 ketone bisulfite adduct by 1H-NMR analysis and calculate the contained yield of ZX008 ketone bisulfite adduct.

Yields and Profiles: The yield for the stage 1 Demonstration batch is summarized Table below. Input: 1700.0 g uncorr., acid, 99.50% area (QC, HPLC), 2-isomer not detected, 4-isomer 0.02% area, RRT1.58 (previously not observed) 0.48% area as per the preparative method. The analytical data is summarized in Table 1A below.

TABLE 1A

Table for isolated yields for step 1 Demonstration batch

| Reference number | Input | Corr. Output | Corr. Yield (% th)** | % w/w (¹H-NMR)* | % area (HPLC, QC) | Comments |
|---|---|---|---|---|---|---|
| Batch A1 | 1700.0 g | 1500.1 g | 89.1 | 45.0 | —.— | Crude ketone as TBME sol. |
| Batch A2 | 1500.1 g | 1716.1 | 77.8 | 76.0 | 98.15 | Bisulfite adduct only |
|  |  |  | 67.3 |  |  | Overall product |

Step 2: Preparation of Ketone

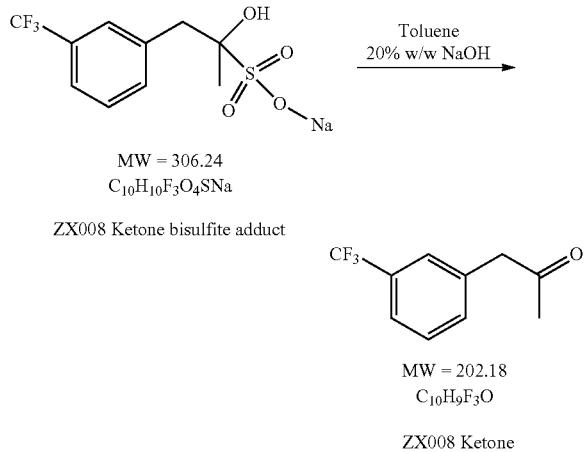

MW = 306.24
C₁₀H₁₀F₃O₄SNa

ZX008 Ketone bisulfite adduct

MW = 202.18
C₁₀H₉F₃O

ZX008 Ketone

Procedure: Charge toluene, (5.0 vol, 4.3 wt), and purified water, (5.0 vol) to the vessel and commence stirring. If necessary, adjust the temperature to 18 to 23° C. and charge ZX008 ketone bisulfite adduct, (1.00 wt corrected for % w/w assay) to the mixture at 18 to 23° C. Charge 20% w/w sodium hydroxide solution to the mixture at 18 to 23° C. adjusting the pH of the mixture to pH 8.0 to 12.0, targeting 9.0 (0.5 to 1.0 vol).

Separate the lower aqueous layer and retain the top organic layer. Wash the organic layer with purified water, (3.0 vol) at 18 to 23° C. Concentrate the organic layer under reduced pressure to ca. 2 vol at 45 to 50° C., targeting 48° C. Charge methanol, (5.0 vol, 4.0 wt) to the mixture at 45 to 50° C., targeting 48° C. Re-concentrate the mixture under reduced pressure to ca. 2 vol at 45 to 50° C., targeting 48° C. Repeat steps 7 and 8 once before continuing with step 9. Cool the mixture to 18 to 23° C. Clarify the mixture into a tared, suitably-sized drum followed by a methanol (1.0 vol, 0.8 wt) line rinse at 18 to 23° C. Determine the w/w assay of ZX008 ketone (WIP) in the mixture by 1H-NMR analysis and calculate the contained yield of ZX008 ketone (WIP) in the mixture. Determine the toluene content in the mixture by 1H-NMR analysis.

Yields and Profiles: The yield for the step 2 Demonstration batch is summarized in Table 1B below. Input: 1200.0 g corr. Ketone bisulfite adduct, 76.0% w/w assay (NMR, using DMB as internal standard in $d_6$-DMSO), (1.00 eq, 1.00 wt corr. for w/w assay) for input calculation.

TABLE 1B

Table for isolated yields for step 2 Demonstration batch

| Corr. Input | Corr. Output | Corr. Yield (% th) | % w/w ($^1$H-NMR)* | % area (HPLC, QC) | Comments |
|---|---|---|---|---|---|
| 1200.0 g | 858.15 g | 108.3 | 25.5 | 99.31 | Purified ketone |

Step 3: Preparation of Fenfluramine.HCl crude

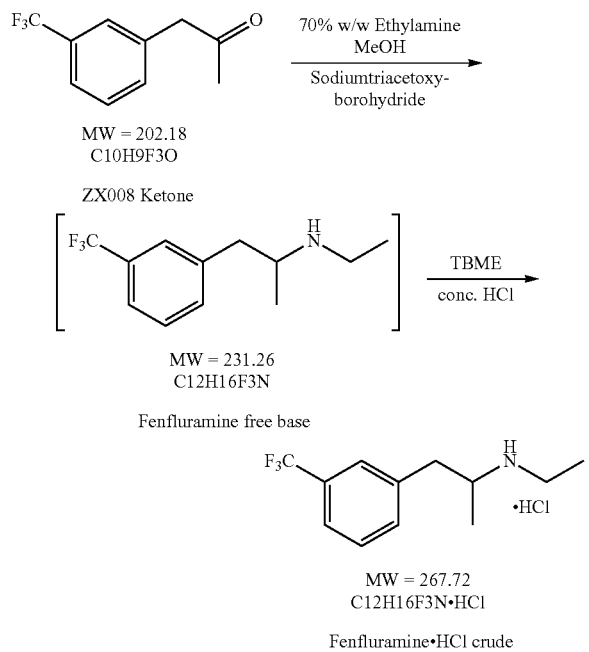

Procedure: Charge the ZX008 ketone (corr. for assay, 1.00 wt, 1.00 eq. isolated as solution in MeOH in stage 2) to a vessel. Charge methanol, code RM0036 (5.0 vol, 4.0 wt) to the mixture at 18 to 23° C. Cool the solution to 0 to 5° C. Charge 70 wt % aqueous ethylamine solution (1.3 vol, 1.6 wt, 4.0 eq) to the mixture at 0 to 10° C., over 15 to 30 minutes, followed by a line rinse with methanol (1.0 vol, 0.8 wt). Warm the mixture to 15 to 20° C. and stir the mixture for a further 60 to 70 minutes at 15 to 20° C. Adjust the mixture to 15 to 18° C. if required, targeting 15° C. Charge sodium triacetoxyborohydride (2.4 wt, 2.25 eq.) to the mixture in approximately 10 portions, keeping the mixture at 15 to 20° C., targeting 17° C. Addition time 1.5 to 2 hours. Caution: Exothermic. Stir the mixture at 15 to 20° C. until complete by HPLC analysis, pass criterion ≤3.0% area ZX008 ketone, typically 2 to 3 hours. Adjust the pH of the mixture to pH>12 by charging 20% w/w aqueous sodium hydroxide solution (5.0 to 6.0 vol) to the mixture at 15 to 40° C. Addition time 10 to 30 minutes. Caution: Exothermic. If necessary, adjust the temperature to 18 to 23° C. Extract the mixture with toluene (3×3.0 vol, 3×2.6 wt) at 18 to 23° C., retaining and combining the top organic layer after each extraction. Wash the combined organic layer with purified water, (1.0 vol) at 18 to 23° C. Heat the mixture to 40 to 50° C., targeting 48° C. Concentrate the mixture under reduced pressure at constant volume maintaining ca. 5 vol by charging the organic layer at approximately the same rate as the distillation rate at 40 to 50° C., targeting 48° C. Cool the mixture to 18 to 23° C. Charge purified water (10.0 vol) to the mixture at 18 to 23° C. Adjust the pH of the mixture to 0.1≤pH≤1.5 at 18 to 23° C. by charging concentrated hydrochloric acid, 0.5 vol. Do not delay from this step until neutralization.

Separate the layers at 18 to 23° C. retaining the bottom aqueous layer. Wash the aqueous layer with toluene, (3.0 vol, 2.6 wt) at 18 to 23° C. retaining the aqueous layer. Adjust the pH of the aqueous layer to pH>12 by charging 20% w/w sodium hydroxide solution at 18 to 23° C. 0.8 to 0.9 vol. Caution: Exothermic. Charge TBME, code RM0002 (2.0 vol, 1.5 wt) to the basic aqueous layer. Separate the layers at 18 to 23° C. retaining the top organic layer. Back-extract the aqueous layer with TBME (2×2.0 vol, 2×1.5 wt) at 18 to 23° C. retaining the organic layers. Wash the combined organic layer with purified water, (2×1.0 vol) at 18 to 23° C. Concentrate the combined organic layers under reduced pressure at 40 to 50° C., targeting 48° C. to ca. 3 vol. Determine the residual toluene content of the mixture by 1H-NMR analysis. Sample for determination of residual water content by KF analysis, AKX reagent. Charge TBME (8.7 vol, 6.4 wt) to the mixture at 40 to 50° C. Cool the solution to 0 to 5° C., targeting 2° C. Charge concentrated hydrochloric acid (0.54 vol, 0.46 wt) maintaining the temperature <15° C. Caution: Exothermic. Line rinse with TBME (1.0 vol, 0.7 wt). If necessary, adjust the temperature to 0 to 10° C. and stir the mixture at 0 to 10° C. for a further 2 to 3 hours. Filter the mixture and wash the filter-cake with TBME (2×4.4 vol, 2×3.3 wt) at 0 to 10° C. Dry the solid at up to 40° C. until the TBME content is ≤0.5% w/w TBME by 1H-NMR analysis. 4 to 8 hours.

Figure 2:
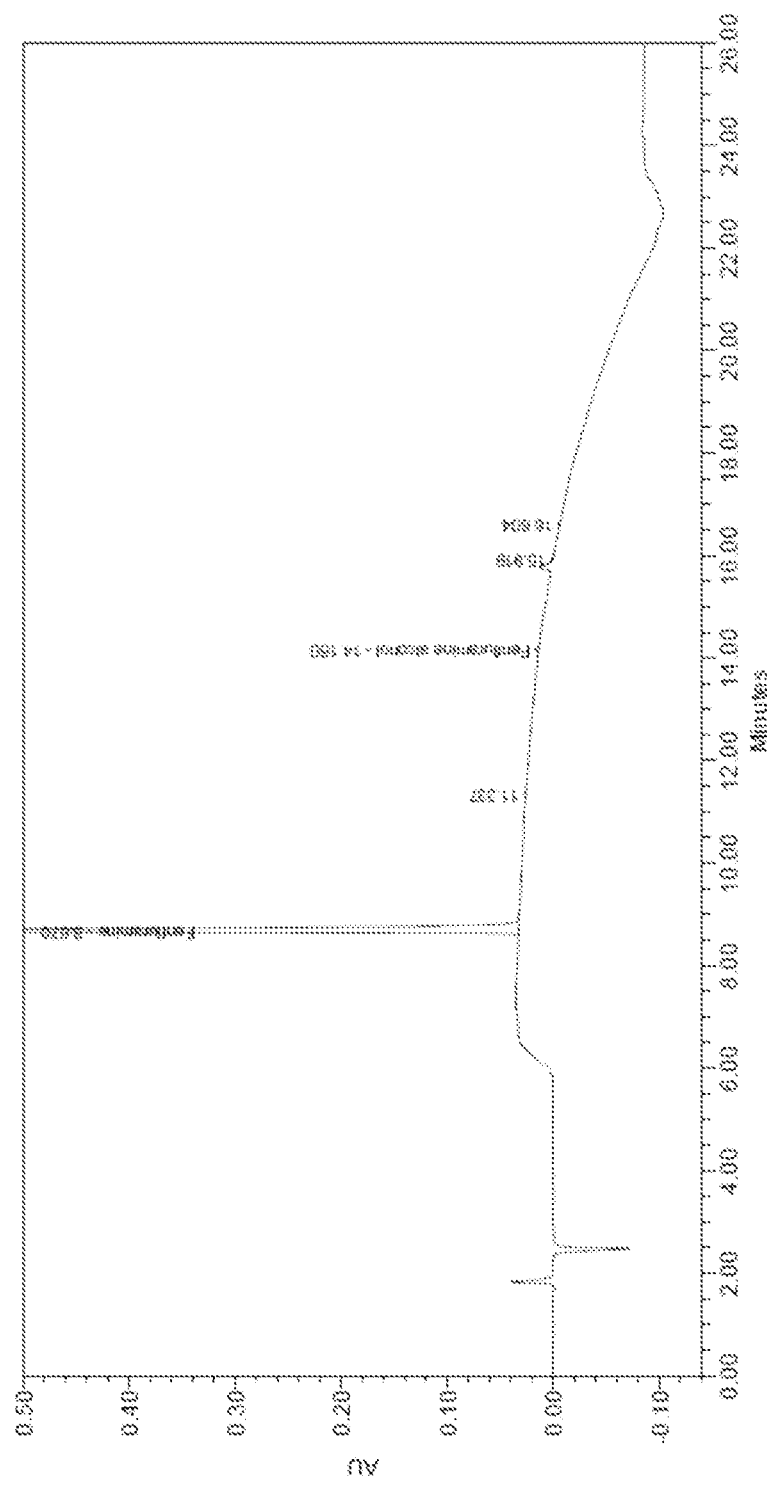
FIG. 2 illustrates an exemplary HPLC chromatogram of a crude preparation of fenfluramine hydrochloride (210 nm UV absorbance).

Yields and Profiles: The yield for the step 3 Demonstration batch is summarized in Table 1C below. Input: 856.8 g corr. Ketone, 44.2% w/w assay (NMR, using TCNB as internal standard in CDCl$_3$), (1.00 eq, 1.00 wt corr. for w/w assay) for input calculation. FIG. 2 and Table 1D shows an exemplary HPLC chromatogram of a crude preparation of fenfluramine hydrochloride (210 nm UV absorbance).

TABLE 1C

Table for isolated yields for step 3 Demonstration batch

| Reference number | Corr. Input | Corr. Output | Corr. Yield (% th) | % w/w ($^1$H-NMR)* | % area (HPLC, QC) | Comments |
|---|---|---|---|---|---|---|
| Batch A1 | 856.8 g | 836.31 g | 85.3 | 44.2 | 99.15 | Fenfluramine free base (in situ intermediate) |
| Batch A2 | | 880.7 | 84.0 based on ketone bisulfite adduct (77.6 based on purified ketone) | 99.5 | 100.00 | Fenfluramine•HCl crude (step 3 and 4.1) |

TABLE 1D

Purity of crude fenfluramine hydrochloride by HPLC (see FIG. 2)
Processed Channel Descr. DAD AU Ch 1 Sample 210, Bw 4
Peak Results

|  | Name | RT | RelRT | Area | Height | USP Tailing | USP Resolution | USP Plate Count | EP s/n | % Area |
|---|---|---|---|---|---|---|---|---|---|---|
| 1 | NorFenfluramine | 7.46 | | | | | | | | |
| 2 | 2-Fenfluramine | 7.68 | | | | | | | | |
| 3 | Fenfluramine | 8.67 | 1.000 | 3789064 | 778178 | 1.7 | | 78796 | 2549.8 | 99.15 |
| 4 | 4-Fenfluramine | 8.95 | | | | | | | | |
| 5 | | 11.34 | 1.308 | 6073 | 1449 | 1.2 | 23.5 | 215529 | 3.8 | 0.16 |
| 6 | ZX008 acid | 12.93 | | | | | | | | |
| 7 | Fenfluramine alcohol | 14.16 | 1.633 | 15266 | 2972 | 1.3 | 24.8 | 215040 | 8.7 | 0.40 |
| 3 | ZX008 ketone | 14.63 | | | | | | | | |
| 9 | Fenfluramine acetamide | 15.55 | | | | | | | | |
| 10 | TOLUENE | 15.75 | | | | | | | | |
| 11 | | 15.92 | 1.836 | 4110 | 1122 | | | | 2.7 | 0.11 |
| 12 | | 16.60 | 1.915 | 6861 | 1630 | 1.5 | | 451209 | 4.3 | 0.18 |
| Sum | | | | 3821374 | | | | | | 100.00 |

Step 4.2: Crystallization of fenfluramine hydrochloride

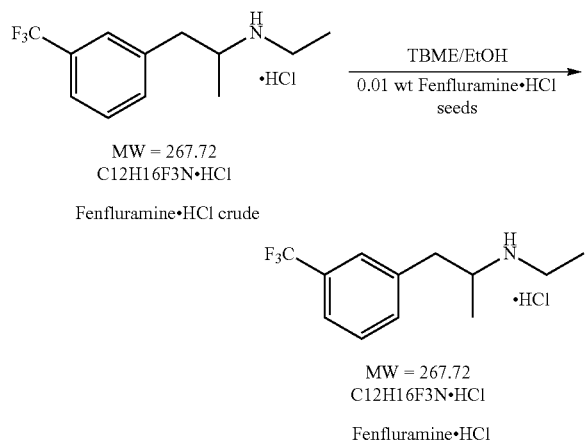

Procedure: Charge Fenfluramine.HCl (crude) (1.00 wt, 1.0 eq.) and TBME (10.0 vol, 7.4 wt) to the vessel and commence stirring. Heat the suspension to reflux (50 to 58° C.). Charge ethanol (5.0 vol, 3.9 wt) maintaining the temperature at 50 to 58° C. Addition time 20 minutes. Stir at 50 to 58° C. for 5 to 10 minutes and check for dissolution. Stir the solution at 50 to 58° C. for 5 to 10 minutes, targeting 54 to 58° C. Clarify the reaction mixture through a 0.1 μm in-line filter at 54 to 58° C., followed by a line rinse with TBME (1 vol, 0.7 wt). Cool the solution to 48 to 50° C. Charge Fenfluramine.HCl, code FP0188 (0.01 wt). Check for crystallization. Allow the suspension to cool to 15 to 20° C., target 17° C. over 5 to 5.5 hours at an approximately constant rate. Stir the mixture at 15 to 20° C., target 17° C. for 2 to 3 hours. Filter the mixture and wash the filter-cake with clarified TBME (2×3.0 vol, 2×2.2 wt) at 5 to 15° C. Dry the solid at up to 40° C. until the TBME content is ≤0.5% w/w TBME and the ethanol content is <0.5% w/w EtOH by 1H-NMR analysis. 4 to 8 hours. Determine the w/w assay of the isolated Fenfluramine.HCl by 1H-NMR analysis.

Figure 3:
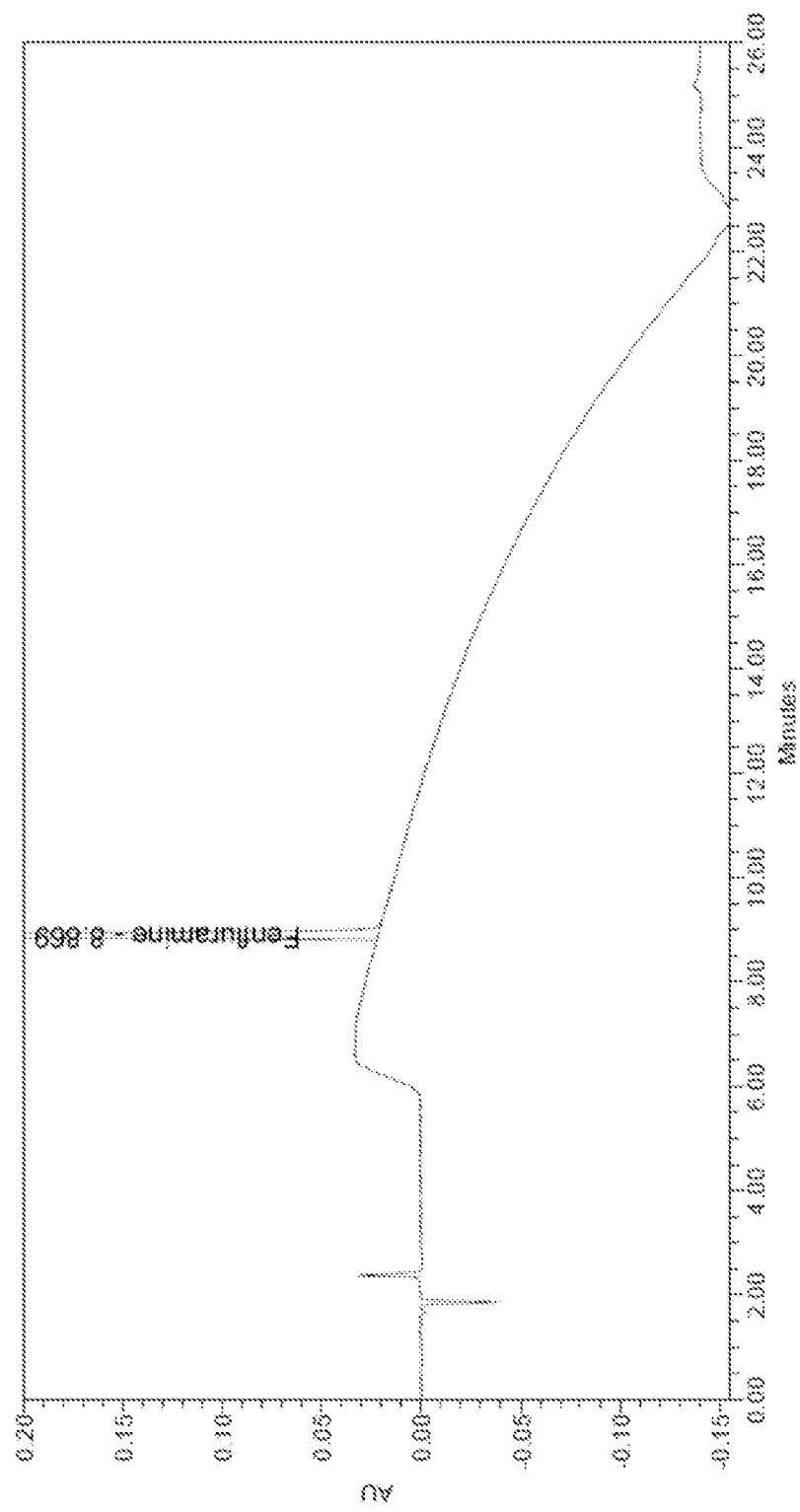
FIG. 3 illustrates an exemplary HPLC chromatogram of a crystallized fenfluramine hydrochloride composition (210 nm UV absorbance).

Yields and Profiles: The yield for the stage 4 Demonstration batch is summarized in Table 1E below. Input: 750.0 g uncorr. Fenfluramine HCl crude (1.00 eq, 1.00 wt uncorr.) for input calculation. FIG. 3 shows an exemplary HPLC chromatogram of a crystallized fenfluramine hydrochloride sample (210 nm UV absorbance).

TABLE 1E

Table for isolated yields for stage 4 Demonstration batch

| Uncorr. Input | Uncorr. Output | Uncorr. Yield (% th) | HPLC (% area, QC) | Comments |
|---|---|---|---|---|
| 750.0 g | 608.0 | 81.1 | 100.00* | Fenfluramine•HCl |

5. In-Process Controls

Table 2 summarizes the in-process controls (IPCs) by IPC number as cited in the narrative procedures above used for Process 1.

TABLE 2

In-Process Controls Performed during Process 1

| IPC No. | Synthesis Step | Sample | Critical Process Description | Method | Acceptance Criteria |
|---|---|---|---|---|---|
| 1 | 1 | Reaction Mixture | Reaction Completion | HPLC | NMT 3.0% Ketone (1) |
| 2 | 1 | Extraction Aqueous Phase | Purity | HPLC | Report percent Fenfluramine Free Base and Fenfluramine Alcohol |
| 3 | 1 | Extraction Organic Phase | Purity | HPLC | Report percent Fenfluramine Free Base and Fenfluramine Alcohol |

TABLE 2-continued

In-Process Controls Performed during Process 1

| IPC No. | Synthesis Step | Sample | Critical Process Description | Method | Acceptance Criteria |
|---|---|---|---|---|---|
| 4 | 1 | Extraction Organic Phase | Purity | HPLC | Report percent Fenfluramine Free Base and Fenfluramine Alcohol |
| 5 | 1 | Extraction Aqueous Phase | Purity | HPLC | NLT 98.0% Fenfluramine HCl LT 1.0% Fenfluramine Alcohol |
| 6 | 1 | Extraction Aqueous Phase | Purity | HPLC | Report percent result of Fenfluramine HCl Fenfluramine Alcohol |
| 7 | 2 | Reaction Mixture | Purity | $^1$H-NMR | Residual Solvents by $^1$H-NMR Ethanol NMT 0.50% w/w Ethyl Acetate NMT 0.50% w/w Methanol NMT 0.50% w/w Toluene NMT 0.50% w/w MTBE NMT 0.50% w/w |

6. Starting Materials

This section provides information and specification controls for the starting materials used to produce clinical supplies of fenfluramine per the routes shown herein.

TABLE 3

Starting Materials via the Route 1

| Chemical Name [CAS. No.] | Code Name | Structure | Source | Step |
|---|---|---|---|---|
| 1-(3-(Trifluoromethyl)-phenylacetone [21906-39-8] | Ketone (1) | F$_3$C-[phenyl]-C(=O)-Me | Fluoro-chem | 1 |
| Ethyl Amine (70% in water) [75-04-7] | Ethyl Amine | EtNH2 | Alfa Aesar | 1 |

TABLE 4

Starting Materials via Route 2

| Chemical Name [CAS. No.] | Code Name | Structure | Source | Step |
|---|---|---|---|---|
| 3-(Trifluoromethyl)-phenylacetic acid [351-35-9] | Acid (1a) | F$_3$C-[phenyl]-CH$_2$-C(=O)OH | To be determined | 1 |
| Acetic Anhydride [108-24-7] | Acetic Anhydride | Me-C(=O)-O-C(=O)-Me | Various | 1 |
| Ethyl Amine (70% in water) [75-04-7] | Ethyl Amine | EtNH2 | Various | 3 |

Table 5 provides a list of the intermediates for the Route 2 synthesis. Both routes share the same intermediate Fenfluramine Free Base (1). Fenfluramine Free Base (1) was treated as an isolated intermediate in the Route 1 process however the Route 2 process uses fixed equipment where both Ketone (2) and Fenfluramine Free Base 1, both non-isolatable oils, are telescoped as a solution and controlled as in-situ intermediates. The Bisulfate Complex (3) is isolated as a solid thus is amenable to treatment as an isolated intermediate and released as such. Crude Fenfluramine HCl can be isolated as an intermediate before recrystallization.

A Specification and Testing Strategy for Intermediates is used. Additional tests and acceptance criteria are be added based upon review of data from the primary stability batches and process validation critical parameter studies. Analytical reference standards are used in full characterization of each intermediate. HPLC methods to determine assay and impurities are the same as the drug substance release method and are validated for Accuracy, Precision: Repeatability, Intermediate Precision, Selectivity/Specificity, Detection limit, Quantitation limit, Linearity, Range, and Robustness.

TABLE 5

In-Situ and Isolated Intermediates

| Chemical Name [CAS No] | Code Name | Step No. | Control | Structure |
|---|---|---|---|---|
| Bisulfate Complex of Ketone 1 | Bisulfate Complex (3) | Step 1 | Isolated (Solid) | 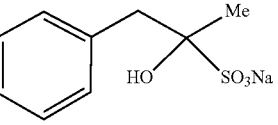 |
| 1-(3-(Trifluoromethyl)-phenylacetone [21906-39-8] | Ketone (2) | Step 2 | In-Situ (oil) | 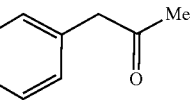 |
| Fenfluramine Free Base [458-24-2] | Fenfluramine Free Base (1) | Step 3 | In-Situ (oil) | 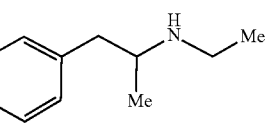 |
| Fenfluramine HCl [404-82-0] | Crude Fenfluramine HCl | Step 4 | Isolated (Solid) | 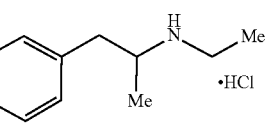 |

7. Characterization

Physiochemical Characteristics of Drug Substance.

Fenfluramine HCl is developed as a single polymorph Form 1. A polymorphism and pre-formulation study has been conducted. Under a wide range of solvents and conditions crystalline material is produced of the same polymorph Form 1 based on a well-defined XRPD pattern and a consistent reproducible endotherm by DSC analysis. A summary of the chemophysical properties of Fenfluramine HCl from this study is provided below. Tabulated data includes example diffractograms, DSCs, and micrographs.

The input Fenfluramine HCl (from precipitative isolation) was characterized to provide reference data and also to determine if the salt was of the same form as that identified from previous salt formations. The XRPD pattern of the salt reveals a crystalline solid that visually matches the reflection patterns obtained from formal crystallization of Fenfluramine HCl and has been arbitrarily termed Form 1. Comparison of the μATR-FTIR data for the salt from various batches gave profiles that had a 99.95% match.

Thermal data analysis matched previous data obtained with only one major endotherm on the DSC thermograph peaking at 172.3° C. that matches the beginning of potential decomposition shown in a TGA thermograph. This also matches the reported melting point quoted for the reference standard.

Isolation of the amorphous form has been shown to be difficult, with attempts using three common methods (rapid solvent evaporation, anti-solvent precipitation and lyophilization) all yielding highly crystalline solids that very closely share the same XRPD pattern of the input Form 1.

Stability analysis of the salt after one week at 40° C./0% RH, three weeks at 40° C./75% RH, and under photostability conditions revealed that the input Form 1 has been maintained with no new impurities observed at 0.1% threshold.

Results from DSC heat cycling analysis of Fenfluramine HCl are comparable to results generated when the material was held at 170° C. No crystallization event was noted and the amorphous was not generated but rather Form 1 was returned.

Holding Fenfluramine HCl at approximately 170° C. for several hours causes a melt and evaporation event to take place with recombination and cooling to provide a white solid. Analysis of the white solid by XRPD, DSC and $^1$H NMR indicates no change in chemical or physical form, purity, or dissociation.

Forced degradation studies carried out have proven Fenfluramine HCl to be stable under a range of conditions. Thermal modulation of Fenfluramine HCl repeatedly yielded the input Form 1.

8. Impurities

Impurities in a drug substance can be organic impurities (process impurities or drug substance-related degradants), inorganic impurities (salt residues or metals) and residual solvents; some of these impurities must be evaluated as to whether or not they are genotoxic agents. These impurities are taken into consideration and controlled in Fenfluramine HCl preparation by using either compendia or validated analytical methods per the specifications or by separate "for information only" testing. The following sections address the actual and potential impurities in Fenfluramine HCl.

Actual Impurities and the Qualification of Synthesis Batch

No impurities reported in cGMP drug substance batches intended for use in humans have exceeded the ICHQ3A qualification thresholds of 0.15% (Table 8). All impurities >0.1% are identified and handled as described in ICH Q3A unless they are genotoxic impurities.

Process Impurities

Table 6 lists the known potential impurities arising from the route of synthesis. All of these impurities are controlled to below ICHQ3A qualification threshold of 0.15% by either process changes and/or control of starting material input purities.

TABLE 6

Fenfluramine HCl Known Potential Process Impurities (Route 1)

| Name [Cas. No.] | Source | PLC (RRT) | Observed in Development Batches ≥0.10%[1] | Observed in cGMP Batches ≥0.10%[1] |
|---|---|---|---|---|
| Ketone (2) [351-35-9] | Starting Material or Intermediate | RRT 0.89 | No | No |
| Fenfluramine Alcohol [621-45-4] | By-product | RRT 1.60 | Yes | No |
| Norfenfluramine [1886-26-6] | By-product | RRT 1.67 | Yes | Yes |
| 2-Fenfluramine [172953-70-7] | Starting Material (isomer) | RRT 0.89 | No | No |
| 4-Fenfluramine [1683-15-4] | Starting Material (isomer) | RRT 1.02 | Yes | Yes |
| N-(3-(trifluoromethyl)-benzyl)ethanamine [90754-95-3] | By-product | RRT 0.53-0.57 | Yes | Yes |

[1]ICH Q3A Identification threshold. The Reporting threshold (LOQ) for the HPLC method is 0.05%.

Degradation Impurities

No change in impurity profile is observed upon long-term storage based on forced degradation studies under the ICH Q1A(R2) conditions of heat (solid, solution), acid, base, oxidizing, and ICH Q1B photostability conditions (solid, solution). Fenfluramine HCL is stable for 7 days as a solid at 150° C. (99.90 parent area %), as a solution in water-acetonitrile at 70° C. (99.73 parent area %), as a solution in acid, base, or photosensitizing conditions at ambient. Only oxidizing conditions (peroxide conditions) produced degradation of Fenfluramine HCl to 94.42% after 1 day producing several new related substances at ~1% each consistent by LC-MS with +16 oxidation by-products Organic Volatiles/Residual Solvents Table 11 in the Batch Analysis section summarizes the solvents used in the process and the resulting amounts found in drug substance. All solvents used in the GMP steps are controlled at ICH Q3A limits using a suitably qualified Head-Space (HS) GC method.

Inorganic Impurities

Heavy Metals conform to either USP <231> or ICP method USP <233> as well as ICH Q3D.

Genotoxic Impurities

The ICH guidelines Q3A and Q3B are not sufficient to provide guidance on impurities that are DNA-reactive. The European Medicines Agency (EMA) guideline (2006) "Guideline on the Limits of Genotoxic Impurities" (EMA 2006) and the ICH Guideline M7 (2014) "Assessment and Control of DNA Reactive (Mutagenic) Impurities in Pharmaceuticals to Limit Potential Carcinogenic Risk" (ICH Guideline M7) are taken into consideration in controlling for potential genotoxic impurities. The diazonium route to prepare ketone (2) described in FIG. 5 has a disadvantage due to the potential formation of genotoxic intermediates shown as boxed compounds (e.g., N-hydroxyaryl, N-nitrosamine and Nitro compound). Muller et al. (Regulatory Toxicology and Pharmacology 44 (2006) 198-211) list potential functional alert groups that can be genotoxic. Safety guidances and regulations indicate that analysis of a process and identification of potential genotoxic agents, and control of such impurities at sub 10 parts per million levels is critical for safety. Often removal of such impurities and/or demonstrating their absence is costly and time consuming and sometimes difficult to achieve technically. For these reasons, selecting synthetic routes that circumvent the potential for such toxic intermediates is important. Because of the potential problems with the diazo route discussed above, as well as potential safety issues using diazo (shock-sensitive) intermediates, as well as the lower purity profiles with this route, this route is less preferred than the preferred route to ketone (2) starting from Nitrile (5). This route produces no potential genotoxic agents and leads to high purity Ketone (2) after isolation by distillation or via the bisulfite salt adduct-hydrolysis sequence.

Additionally, attempts to remove isomer by-products present in commercial supplies of Aniline were unsuccessful whereas crystallization the Acid (4) resulting from hydrolysis of the nitrile (5) provides crystalline Acid (4) which can be purified to remove isomers early in synthesis. Removing impurities and/or isomers early in a synthesis is preferred if it is known such impurities track to final product, as the need to crystalize a final product at the end of a synthesis is more costly in losses and impacts cost of goods more greatly than removing early in synthesis before raw materials are invested along the process.

TABLE 7

Potential Impurities in Fenfluramine Synthesis

| No. | Compound | Synthesis Route | | CAS. No. |
|---|---|---|---|---|
| | | Route 1 | Route 2 | |
| 1 | 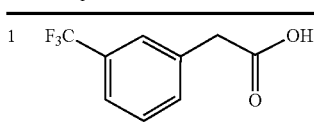 | No | Starting Material | [351-35-9] |

TABLE 7-continued

Potential Impurities in Fenfluramine Synthesis

| No. | Compound | Synthesis Route Route 1 | Route 2 | CAS. No. |
|---|---|---|---|---|
| 2 | F₃C-C₆H₄-CH₂-C(=O)-Me | Starting Material | Intermediate | [21906-39-8] |
| 4 | | No | Intermediate | Not Available |
| 5 | | Potential Impurity | Potential Impurity | [621-45-4] |
| 6 | F₃C-C₆H₄-CH₂-CH(Me)-NH₂ | Potential Impurity | Potential Impurity | [1886-26-6] |
| 7 | 2-CF₃-C₆H₄-CH₂-CH(Me)-NH-Et | Potential Impurity | Potential Impurity | [172953-70-7] |
| 8 | 4-F₃C-C₆H₄-CH₂-CH(Me)-NH-Et | Potential Impurity | Potential Impurity | [1683-15-4] |
| 9 | 3-F₃C-C₆H₄-CH₂-NH-Et | Potential Impurity | Potential Impurity | [90754-95-3] |

TABLE 8

Batch Analyses of Fenfluramine HCl Drug Substance

| Test | | Batch 1 | Batch 2 | Batch 3 | Batch 4 |
|---|---|---|---|---|---|
| Appearance* | | White solid | White solid | White solid | White solid |
| Identification: FTIR* | | a | a | Conforms | Conforms |
| Identification: ¹H-NMR | | Conforms | Conforms | Conforms | Conforms |
| Identification: ¹³C-NMR | | Conforms | Conforms | Conforms | Conforms |
| Identification: MS | | Conforms | Conforms | Conforms | Conforms |
| Purity (HPLC area %) | | 99.57 | 99.77 | b | b |
| Assay (w/w %)* Anhydrous Basis (HPLC) | | 99.49 | 100.37 | 100.79 | 100.13 |
| Impurities (HPLC area %) | 2-Fenfluramine | ND | ND | ND | ND |
| | 4-Fenfluramine) | 0.16 | 0.15 | 0.11 | 0.12 |
| | Fenfluramine Alcohol | ND | ND | ND | ND |
| | 1-((3-trifluoromethyl) phenyl) acetone | ND | ND | ND | ND |
| | Acetamide | 0.27 | ND | ND | ND |
| | N-(3-(trifluoromethyl)-benzyl)ethanamine (RRT 0.53-0.57) | ND | 0.08 | 0.07 | 0.13 |
| | Total | 0.43 | 0.23 | 0.19 | 0.25 |
| Residual Solvents (GC): ppm | Methanol | ND | ND | ND | ND |
| | Ethanol | ND | ND | ND | ND |
| | MTBE | 597 | 844 | 472 | 800 |
| | Ethyl Acetate | 115 | 164 | 79 | 150 |
| | Toluene | 4 | 7 | ND | ND |
| Residue on Ignition (w/w %) | | 0.01 | 0.02 | 0.04 | ND |
| Heavy Metals (as Pb) | | <10 ppm | <10 ppm | b | b |
| Heavy Metals ICP | As | a | a | <0.1 | <0.1 |

TABLE 8-continued

Batch Analyses of Fenfluramine HCl Drug Substance

|  | Test | Batch 1 | Batch 2 | Batch 3 | Batch 4 |
|---|---|---|---|---|---|
| (ppm) | Cd | a | a | 0.1 | 0.1 |
|  | Hg | a | a | <0.1 | <0.1 |
|  | Pb | a | a | 0.2 | <0.4 |
|  | Co | a | a | <0.1 | 0.1 |
|  | Mo | a | a | <0.1 | <0.1 |
|  | Se | a | a | <0.1 | <0.1 |
|  | V | a | a | <0.1 | <0.1 |
| Water Determination* (Karl Fischer) |  | 0.21 | 0.08 | 0.02 | 0.03 |
| Chloride content by titration |  | 13.19 | 13.09 | 12.92 | 12.93 |
| XRPD* |  | Form 1 | Form 1 | Form 1 | Form 1 |
| Differential Scanning Calorimetry (DSC)* | Onset | 169.42° C. | 169.23° C. | 169.85° C. | 168.70° C. |
|  | Peak | 172.82° C. | 171.55° C. | 172.22° C. | 171.97° C. |
| Particle Size Malvern (μm) | % Volume mean (D) | a | 11 | 11 | 19 |
|  | D10 | a | 1 | 1 | 1 |
|  | D50 | a | 5 | 7 | 9 |
|  | D90 | a | 17 | 26 | 32 |
| Microbial Limits Tests* USP <61> | Total aerobic microbial Count | a | a | LT 100 CFU/g | LT 100 CFU/g |
|  | Total yeast and molds count | a | a | LT 100 CFU/g | LT 100 CFU/g |
| USP <62> | Absence of Pathogens | a | a | Absent | Absent |

[a] These tests were added to the specifications recently thus only recent lots have been tested using this test.
[b] These tests have been dropped from the specifications thus only historical lots have been tested using this test.

Example 3

Method for Hydrolysis of Nitrile (5) to Acid

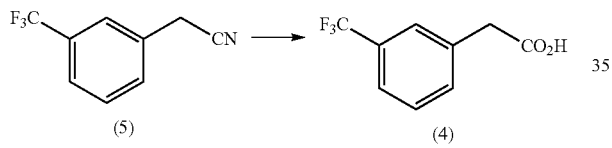

TABLE 9

| Step | Operation |
|---|---|
| 1. | Charge 3-(trifluoromethyl)phenyl acetonitrile (1.0 eq., 1.00 wt) and purified water (5.0 vol) to a vessel and commence stirring. |
| 2. | Dissolve sodium hydroxide (1.1 wt, 5.0 eq.) in purified water (4.0 vol) at up to 40° C. in a suitable make-up vessel. Caution very exothermic. |
| 3. | Charge the aqueous sodium hydroxide solution to the mixture from step 1 at up to 40° C. followed by a line rinse with purified water, code RM0120 (1.0 vol) at up to 40° C. |
| 4. | Heat the mixture to 75 to 85° C., target 80° C. over 1 to 2 hours. |
| 5. | Heat the mixture at 80° C. until ≤0.1% area nitrile by HPLC analysis, expected 4 to 6 hours. |
| 6. | Cool the mixture to 18 to 23° C. |
| 7. | Adjust the pH of the mixture to pH ≤2 by charging 6M HCl (expected 7.0 vol) to the mixture at 18 to 23° C. Caution exothermic. |
| 8. | Stir the mixture for 15 to 30 minutes at 18 to 23° C. |
| 9. | Filter and wash the filter-cake with purified water (2x5.0 vol) at 18 to 23° C. |
| 10. | Slurry wash the filter-cake with n-heptane, code RM (2xvol) at 0 to 5° C. |
| 11. | Dry the isolated solid at up to 45° C. until the water content is ≤0.2% w/w by KF analysis according to MET/AN/0163, AKX-reagent. |
| 12. | Crystallization of crude stage 1 acid (1.00 wt for input calculation) |
| 13. | Charge the crude stage 1 acid (1.00 wt), ethyl acetate (0.75 vol) and n-heptane (10.5 vol) to a vessel and commence stirring. |
| 14. | Heat the mixture to 50° C. to achieve dissolution. |
| 15. | Cool the mixture to 5° C. and age at 5° C. for at least 30 mins. |
| 16. | Filter and wash the filter-cake with n-heptane (2x5.0 vol). |
| 17. | Dry the isolated solid at up to 45° C. until the residual solvent content by $^1$H-NMR analysis is ≤.0% w/w EtOAc and ≤.0% w/w n-heptane. |

Expected yield: 60 to 90% th uncorr. 68 to 103% w/w
Expected purity: 93.00 to 99% area by HPLC

Example 4

Evaluation of Minor Components Formed During Dakin-West Reaction in Preparation of Ketone (2)

The impurities formed during the Dakin-West chemistry and their subsequent removal using the distillation or via isolation of the product ketone as the bisulfite salt are described. The two major impurities found are shown below.

tion procedure during reaction workup provides an improvement in purity of the resulting composition as it serves to remove any unreacted acid. Crude Ketone (2) made by the Diazo route showed similar improvements in purity when treated with bisulfite and isolated.

TABLE 10

Analytical purity data for crude Ketone (2) isolated from Dakin-West reaction before and after bisulfite purification. RRT is relative retention time (min) in chromatogram.

| | | | | | RRT | | | | | | | | |
|---|---|---|---|---|---|---|---|---|---|---|---|---|---|
| Entry | 0.85 | 0.93 Aniline | 0.95 | 0.99 | 1.00 Ketone | 1.004 | 1.009 Nitrile | 1.02 | 1.06 Acid | 1.10 | 1.15 | 1.34 | 1.38 |
| 1 | 1.38 | 1.76 | 0.04 | 0.49 | 61.66 | nd | 0.29 | 0.29 | 0.26 | 1.98 | 0.66 | 4.64 | 0.14 |
| 2 | 0.82 | nd | nd | nd | 95.53 | 0.31 | 0.14 | nd | 0.23 | 0.01 | 0.10 | 0.43 | 0.27 |
| 3 | nd | nd | nd | nd | 77.82 | nd | nd | nd | nd | 3.12 | 0.01 | 7.76 | 6.16 |
| 4 | nd | nd | nd | nd | 98.82 | nd | 0.63 | nd | nd | nd | 0.02 | 0.30 | 0.22 |
| 5 | 0.08 | nd | nd | 0.05 | 72.02 | nd | 0.02 | nd | nd | 7.11 | 0.04 | 3.58 | 10.33 |
| 6 | nd | nd | nd | nd | 99.49 | nd | 0.02 | nd | nd | nd | 0.02 | 0.11 | 0.24 |
| 7 | 0.15 | 0.23 | nd | nd | 98.35 | nd | nd | nd | nd | nd | nd | nd | 0.24 |
| 8 | nd | nd | nd | nd | 99.84 | nd | nd | nd | nd | nd | nd | nd | nd |

Entry 1 (Crude ketone from Route 1); Entry 2 (Ketone Route 1 post bisulfite release); Entry 3 (Crude ketone using crude acid); Entry 4 (Ketone using crude acid Post bisulfite); Entry 5 (Crude ketone using cryst. acid); Entry 6 (Crude ketone using cryst. acid post bisulfite); Entry 7 (Crude ketone using cryst. acid); Entry 8 (Fluorochem ketone); Entry 9 (Fluorochem ketone post bisulfite).

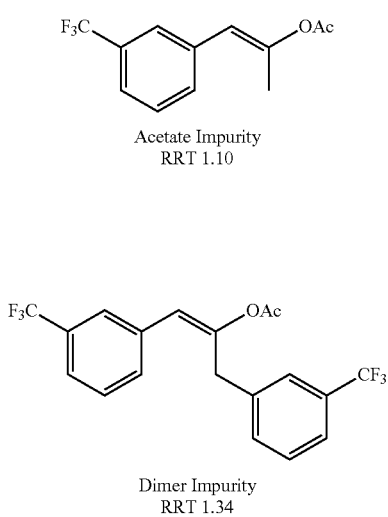

Acetate Impurity
RRT 1.10

Dimer Impurity
RRT 1.34

Table 10 shows a table of analytical data for crude Ketone (2) isolated from Dakin-West reaction before and after bisulfite purification. In entry 1 crude Ketone isolated directly from the Dakin-West step (pre-bisulfite treatment) is 61.66% purity (e.g. about 62%) and contains 1.98% (e.g., about 2%) and 4.64% (e.g., about 5%) respectively of impurities having RRTs 1.20 and 1.34, which are proposed to be the acetate and dimer impurities (e.g., depicted above), respectively. In entry 2 which is post bisulfite treatment these are other impurities are removed leading to an overall purity of 95.55% (e.g., about 96%). Other entries shown in Table 10 provide other examples of this impurity enhancement by bisulfite treatment of crude Dakin-West ketone. The last two entries use pure Fluorchem ketone as input to the salt formation step and re-isolation of ketone thus illustrating that the salt formation and re-isolation does not produce any impurities itself. Additionally use of bicarbonate extrac-

Example 5

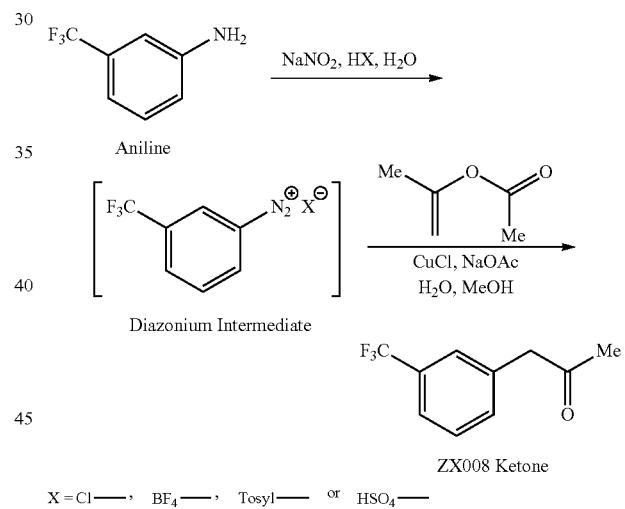

Additional Method for Preparation of 1-(3-Trifluoromethyl) phenyl-propan-2-one 35 mL of water and 45 g of 37% (w/w) aqueous hydrochloric acid are put in a flask equipped with stirrer and dropping funnel. 24.25 Grams (0.151 moles) of m-trifluoromethylaniline are added after having cooled to 10 degree C. with an ice bath and then, at 5 degree C., an aqueous solution containing 12.43 g (0.180 moles) of sodium nitrite in 150 ml of water is slowly added. The reaction mixture is stirred for 30 minutes and then is poured during 30 minutes into a mixture made by 90 ml of water, 1.35 g (0.014 moles) of cuprous chloride, 2.30 g (0.013 moles) of cupric chloride dihydrate, 50 ml of acetone, 40.8 g (0.300 moles) of sodium acetate trihydrate and 23 g (0.230 moles) of isopropenyl acetate while keeping the reaction temperature at 30 degree C. After further 30 minutes of stirring, the reaction mixture is brought to 20 degree C., 50 ml of methylene chloride are added and the two layers are separated.

The aqueous layer is discarded while the organic layer is concentrated under vacuum until an oil is obtained which is treated with 35 g of sodium metabisulfite, 70 ml of water and 150 ml of heptane under stirring at room temperature for 12 hours. The suspension is filtered, the bisulfite complex is washed on the filter with 50 ml of heptane and then suspended in a two-phase mixture made by 100 ml of methylene chloride and 150 ml of a 10% (w/v) aqueous solution of sodium hydroxide. The layers are separated after one hour of stirring at room temperature, the aqueous phase is discarded while the organic layer is washed with water and evaporated under vacuum to give pure ketone.

Notwithstanding the appended claims, the disclosure set forth herein is also defined by the following clauses:

Clause 1. A method of preparing a fenfluramine active pharmaceutical ingredient, the method comprising:
(a) hydrolyzing a 2-(3-(trifluoromethyl)phenyl)acetonitrile composition to produce a 2-(3-(trifluoromethyl)phenyl) acetic acid composition;
(b) reacting the 2-(3-(trifluoromethyl)phenyl)acetic acid composition with acetic anhydride and a catalyst to produce a 1-(3-(trifluoromethyl)phenyl)propan-2-one composition; and
(c) reductively aminating the 1-(3-(trifluoromethyl)phenyl)propan-2-one composition with ethylamine using a borohydride reducing agent to produce a fenfluramine composition.

Clause 2. The method of clause 1, wherein the 2-(3-(trifluoromethyl)phenyl) acetonitrile composition comprises at least 0.2% by weight of trifluoromethyl-phenyl regioisomers.

Clause 3. The method of any one of clauses 1 and 2, wherein the 2-(3-(trifluoromethyl)phenyl)acetonitrile composition is prepared from trifluoromethylbenzene.

Clause 4. The method of any one of clauses 1-3, further comprising, prior to step (b), purifying the 2-(3-(trifluoromethyl)phenyl)acetic acid composition to produce a composition substantially devoid of one or more trifluoromethyl-phenyl regioisomers and substantially devoid of trifluoromethylbenzaldehyde and benzaldehyde.

Clause 5. The method of clause 4, wherein the purifying comprises crystallization of 2-(3-(trifluoromethyl)phenyl) acetic acid from the composition.

Clause 6. The method of any one of clauses 1-5, wherein step (b) comprises purification of the 1-(3-(trifluoromethyl)phenyl)propan-2-one composition via a ketone bisulfite adduct.

Clause 7. The method of any one of clauses 1-6, wherein step (b) comprises selectively reacting 2-(3-(trifluoromethyl)phenyl)acetic acid in the presence of unreacted 2-(2-(trifluoromethyl)phenyl)acetic acid.

Clause 8. The method of any one of clauses 1-7, wherein step (b) further comprises removing unreacted 2-(2-(trifluoromethyl)phenyl)acetic acid regioisomer from the 1-(3-(trifluoromethyl)phenyl)propan-2-one composition.

Clause 9. The method of any one of clauses 1-8, wherein the fenfluramine composition is crude and substantially devoid of: trifluoromethyl-phenyl regioisomers of fenfluramine or a salt thereof; metal catalysts; Class I and/or Class II solvents (ICH Q3C) (e.g., Benzene, Carbon tetrachloride, 1,2-Dichloroethane, 1,1-Dichloroethene and/or 1,1,1-Trichloroethane); and a reduced alcohol side product.

Clause 10. The method of any one of clauses 1-9, wherein the fenfluramine composition is crude and has less than 1% by weight in total of trifluoromethyl-phenyl regioisomers of fenfluramine or a salt thereof.

Clause 11. The method of any one of clauses 1-10, wherein the borohydride reducing agent is sodium triacetoxyborohydride.

Clause 12. The method of any one of clauses 1-11, wherein the fenfluramine composition is crude and has less than 10% by weight of a reduced alcohol side product.

Clause 13. The method of any one of clauses 1-12, further comprising crystallizing fenfluramine or a salt thereof from the fenfluramine composition.

Clause 14. The method of clause 1, wherein step (a) is performed under aqueous acidic conditions.

Clause 15. The method of clause 14, wherein the yield of step (a) is 80% or more.

Clause 16. The method of clause 1, wherein step (b) is performed under conditions that include contacting the 2-(3-(trifluoromethyl)phenyl)acetic acid composition with about 0.5 equivalents of 1-methylimidazole and about 5 equivalents or more of acetic anhydride in an optional solvent.

Clause 17. The method of clause 16, wherein the yield of step (b) is 80% or more.

Clause 18. The method of clause 1, wherein step (c) is performed under conditions that comprise contacting the 1-(3-(trifluoromethyl)phenyl)propan-2-one composition with a solution of 70% by weight of ethylamine in water and about 2.25 equivalents or more of triacetoxyborohydride in methanol solvent.

Clause 19. The method of clause 18, wherein the yield of step (c) is 80% or more.

Clause 20. The method of clause 1, wherein the fenfluramine composition has following profile: at least 80% by weight of fenfluramine or a salt thereof; less than 1% by weight of 2-fenfluramine or a salt thereof; less than 1% by weight of 4-fenfluramine or a salt thereof; and less than 10% by weight of fenfluramine reduced alcohol side product.

Clause 21. The method of any one of clauses 1-20, further comprising converting fenfluramine in the fenfluramine composition to a pharmaceutically acceptable salt of fenfluramine.

Clause 22. The method of clause 21, further comprising crystallizing the pharmaceutically acceptable salt of fenfluramine from the fenfluramine composition.

Clause 23. The method of clause 22, wherein the pharmaceutically acceptable salt of fenfluramine has following purity profile: at least 90% or more of the pharmaceutically acceptable salt of fenfluramine; less than 1% by weight of 2-fenfluramine; less than 5% by weight of 4-fenfluramine; and less than 5% by weight of fenfluramine reduced alcohol side product.

Clause 24. The method of any one of clauses 20-22, wherein the pharmaceutically acceptable salt of fenfluramine is fenfluramine hydrochloride.

Clause 25. The method of any one of clauses 1-20, further comprising purifying fenfluramine free base from the fenfluramine composition.

Clause 26. The method of any one of clauses 1-25, further comprising performing a chiral separation of a racemic fenfluramine composition to produce a non-racemic fenfluramine composition comprising a predominant stereoisomer of fenfluramine.

Clause 27. The method of clause 26, wherein the predominant stereoisomer of fenfluramine is (S)—N-Ethyl-1-[3-(trifluoromethyl)phenyl]-propan-2-amine Clause 28. The method of clause 26, wherein the predominant stereoisomer of fenfluramine is (R)—N-Ethyl-1-[3-(trifluoromethyl)phenyl]-propan-2-amine.

Clause 29. A fenfluramine composition produced according to the method of any one of clauses 1-28.

Clause 30. A fenfluramine active pharmaceutical ingredient comprising a pharmaceutically acceptable salt of fenfluramine and having less than 0.2% by weight in total of trifluoromethyl regioisomers.

Clause 31. The fenfluramine active pharmaceutical ingredient of clause 30, having the following profile: at least 90% or by weight of a pharmaceutically acceptable salt of fenfluramine; less than 0.2% by weight of 2-fenfluramine; less than 0.2% by weight of 4-fenfluramine; and less than 1% by weight of fenfluramine alcohol.

Clause 32. The fenfluramine active pharmaceutical ingredient of any one of clauses 30-31, wherein heavy metal components are substantially or completely eliminated from the composition.

Clause 33. The fenfluramine active pharmaceutical ingredient of any one of clauses 30-31, wherein Class 1 and/or Class 2 solvents are substantially or completely eliminated from the composition (e.g., the fenfluramine active pharmaceutical ingredient of any one of clauses 30-31, is substantially devoid of Class 1 and/or Class 2 solvents).

Clause 34. The fenfluramine active pharmaceutical ingredient of any one of clauses 30-33, wherein fenfluramine alcohol is completely eliminated from the composition.

Clause 35. The fenfluramine active pharmaceutical ingredient of any one of clauses 30-34, wherein benzaldehyde and trifluorobenzaldehyde are substantially or completely eliminated from the composition.

Clause 36. The fenfluramine active pharmaceutical ingredient of any one of clauses 30-35, wherein the composition is unpurified.

Clause 37. A pharmaceutical composition, comprising the fenfluramine active pharmaceutical ingredient of any one of clauses 30-36 and a pharmaceutically acceptable excipient.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

That which is claimed is:

1. A method of treating epilepsy, comprising administering to a patient a therapeutically effective amount of a formulation comprising a fenfluramine active pharmaceutical ingredient produced by a process comprising the steps of:
    (a) hydrolyzing a 2-(3-(trifluoromethyl)phenyl)acetonitrile composition to produce a 2-(3-(trifluoromethyl)phenyl)acetic acid composition;
    (b) purifying the 2-(3-(trifluoromethyl)phenyl)acetic acid composition via crystallization to produce a purified 2-(3-(trifluoromethyl)phenyl)acetic acid having less than 0.2% by weight in total of trifluoromethyl-phenyl regioisomers;
    (c) reacting the purified 2-(3-(trifluoromethyl)phenyl)acetic acid composition with acetic anhydride and a catalyst to produce a 1-(3-(trifluoromethyl)phenyl)propan-2-one composition; and
    (d) reductively aminating the 1-(3-(trifluoromethyl)phenyl)propan-2-one composition with ethylamine using a borohydride reducing agent to produce a fenfluramine active pharmaceutical ingredient comprising at least one trifluoromethyl-phenyl regioisomer of fenfluramine, wherein the at least one trifluoromethyl-phenyl regioisomer of fenfluramine is present in some amount;
    wherein the fenfluramine active pharmaceutical ingredient has the following profile:
        at least 80% by weight of fenfluramine or a salt thereof
        at least 0.01% by weight of 2-fenfluramine or a salt thereof;
        at least 0.01% by weight of 4-fenfluramine or a salt thereof; and
        less than 10% by weight of fenfluramine reduced alcohol side product.

2. The method of claim 1, wherein the 2-(3-(trifluoromethyl)phenyl) acetonitrile composition is prepared from trifluoromethylbenzene.

3. The method of claim 1, wherein the fenfluramine active pharmaceutical ingredient is produced by a process where step (c) comprises purification of the 1-(3-(trifluoromethyl)phenyl)propan-2-one composition via a ketone bisulfite adduct.

4. The method of claim 1, wherein the fenfluramine active pharmaceutical ingredient is substantially devoid of;
    metal catalysts;
    solvents selected from acetonitrile, benzene and substituted benzenes, carbon tetrachloride, chloroform, cyclohexane, 1,2-dichloroethane, 1,1-dichloroethane, 1,2-dimethoxyethane, DMF, 1,4-dioxane, methanol, methylbutyl ketone, N-methylpyrrolidinone, pyridine, toluene, 1,1,1-trichloroethane, 1,1,2-trichloroethene, and xylene; and
    has less than 5% by weight of reduced alcohol side product.

5. The method of claim 1, wherein the fenfluramine active pharmaceutical ingredient is produced by a process where step (c) is performed under conditions that comprise contacting the 2-(3-(trifluoromethyl)phenyl)acetic acid composition with about 0.5 equivalents of 1-methylimidazole and about 5 equivalents or more of acetic anhydride in an optional solvent.

6. The method of claim 1, wherein the fenfluramine active pharmaceutical ingredient is produced by a process where step (d) is performed under conditions that comprise contacting the 1-(3-(trifluoromethyl)phenyl)propan-2-one composition with a solution of 70% by weight of ethylamine in water and about 2.25 equivalents or more of triacetoxyborohydride in methanol solvent.

7. The method of claim 1, wherein the fenfluramine active pharmaceutical ingredient is produced by a process that further comprises the step of purifying fenfluramine free base.

8. The method of claim 1, wherein the fenfluramine active pharmaceutical ingredient is produced by a process that further comprises the step of performing a chiral separation of a racemic fenfluramine composition to produce a non-racemic fenfluramine composition comprising a predominant stereoisomer of fenfluramine.

9. The method of claim 1, wherein the fenfluramine active pharmaceutical ingredient is produced by a process where the purified 2-(3-(trifluoromethyl)phenyl)acetic acid composition of step (b) has less than 0.1% by weight 4-trifluoromethyl-phenyl regioisomer.

10. The method of claim 1, wherein the fenfluramine active pharmaceutical ingredient is produced by a process where the purified 2-(3-(trifluoromethyl)phenyl)acetic acid composition of step (b) has less than 0.1% by weight 2-trifluoromethyl-phenyl regioisomer.

11. A method of treating epilepsy, comprising administering to a patient a therapeutically effective amount of a formulation comprising a fenfluramine active pharmaceutical ingredient produced by a process comprising the steps of:
  (a) hydrolyzing a 2-(3-(trifluoromethyl)phenyl)acetonitrile composition to produce a 2-(3-(trifluoromethyl)phenyl)acetic acid composition;
  (b) purifying the 2-(3-(trifluoromethyl)phenyl)acetic acid composition via crystallization to produce a purified 2-(3-(trifluoromethyl)phenyl)acetic acid having less than 0.2% by weight in total of trifluoromethyl-phenyl regioisomers;
  (c) reacting the purified 2-(3-(trifluoromethyl)phenyl)acetic acid composition with acetic anhydride and a catalyst to produce a 1-(3-(trifluoromethyl)phenyl)propan-2-one composition; and
  (d) reductively aminating the 1-(3-(trifluoromethyl)phenyl)propan-2-one composition with ethylamine using a borohydride reducing agent to produce a fenfluramine active pharmaceutical ingredient comprising at least one trifluoromethyl-phenyl regioisomer of fenfluramine, wherein the at least one trifluoromethyl-phenyl regioisomer of fenfluramine is present in some amount;
  wherein the fenfluramine active pharmaceutical ingredient comprises at least 0.01% by weight of 4-fenfluramine or a salt thereof.

12. The method of claim 11, wherein the fenfluramine active pharmaceutical ingredient comprises at least 0.01% by weight of 2-fenfluramine or a salt thereof.

13. A method of treating epilepsy, comprising administering to a patient a therapeutically effective amount of a formulation comprising fenfluramine and at least one trifluoromethyl-phenyl regioisomer of fenfluramine, wherein the at least one trifluoromethyl-phenyl regioisomer of fenfluramine is present in an amount of at least 0.01% by weight and less than 0.2% by weight in total of trifluoromethyl-phenyl regioisomers of fenfluramine.

14. The method of claim 13, wherein the fenfluramine is fenfluramine HCL.

15. The method of claim 13, wherein the patient suffers from Dravet Syndrome.

16. The method of claim 14, wherein the patient suffers from Dravet Syndrome.

* * * * *

UNITED STATES PATENT AND TRADEMARK OFFICE
CERTIFICATE OF CORRECTION

PATENT NO. : 11,634,377 B2
APPLICATION NO. : 17/159367
DATED : April 25, 2023
INVENTOR(S) : Londesbrough et al.

It is certified that error appears in the above-identified patent and that said Letters Patent is hereby corrected as shown below:

In the Specification

In Column 11, Lines 8-14, delete " 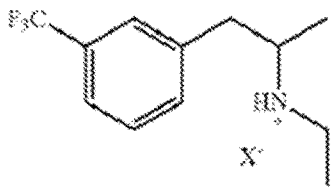 " and insert 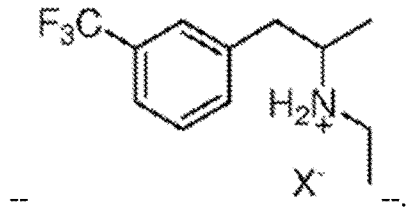 --.

In Column 25, Line 52, delete "Synthesiss" and insert -- Synthesis --.

In Column 26, Line 46, delete "Metyl-" and insert -- Methyl- --.

In Column 28, Line 31, delete "1-Methylimicazole" and insert -- 1-Methylimidazole --.

In Column 39, Line 37, delete "by-products" and insert -- by-products. --.

In Column 41, Line 6, below " 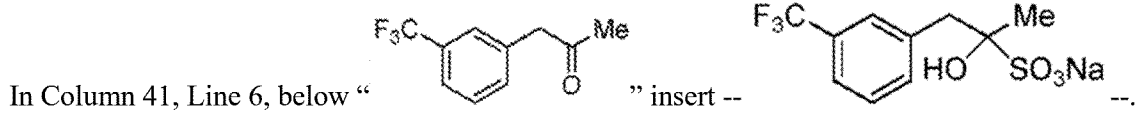 " insert -- --.

Signed and Sealed this
Seventeenth Day of October, 2023

Katherine Kelly Vidal
*Director of the United States Patent and Trademark Office*

CERTIFICATE OF CORRECTION (continued)

In Column 41, Line 7, above " 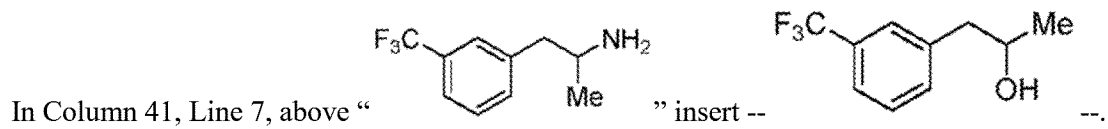 " insert -- --.

In Column 48, Line 64, delete "2-amine" and insert -- 2-amine. --.